(12) United States Patent
Langham et al.

(10) Patent No.: US 6,518,283 B1
(45) Date of Patent: Feb. 11, 2003

(54) SQUARIC ACID DERIVATIVES

(75) Inventors: Barry John Langham, Reading (GB); Rikki Peter Alexander, High Wycombe (GB); John Clifford Head, Maidenhead (GB); Janeen Marsha Linsley, High Wycombe (GB); John Robert Porter, Chinnor (GB); Sarah Catherine Archibald, Maidenhead (GB); Graham John Warrellow, Northwood (GB)

(73) Assignee: Celltech R&D Limited, Slough (GB)

( * ) Notice: Subject to any disclaimer, the term of this patent is extended or adjusted under 35 U.S.C. 154(b) by 0 days.

(21) Appl. No.: 09/579,317

(22) Filed: May 25, 2000

(30) Foreign Application Priority Data

May 28, 1999 (GB) .............................................. 9912640
Feb. 8, 2000 (GB) .............................................. 0002858

(51) Int. Cl.$^7$ ..................... A61K 31/445; C07D 239/72; C07D 211/32; C07C 49/613
(52) U.S. Cl. ...................... 514/317; 514/300; 514/259; 514/678; 544/283; 546/190; 546/191; 546/122; 546/123; 568/381
(58) Field of Search .............................. 514/300, 317, 514/259, 678; 544/283; 546/190, 191, 122, 123; 568/381

(56) References Cited

U.S. PATENT DOCUMENTS

| | | | |
|---|---|---|---|
| 4,470,973 A | 9/1984 | Natarajan et al. | 424/177 |
| 4,554,273 A | 11/1985 | Bayssat et al. | 514/221 |
| 4,987,132 A | 1/1991 | Mase et al. | 514/252 |
| 5,164,372 A | 11/1992 | Matsuo et al. | 514/19 |
| 5,227,490 A | 7/1993 | Hartman et al. | 514/317 |
| 5,260,277 A | 11/1993 | McKenzie | 544/18 |
| 5,296,486 A | 3/1994 | Lazer et al. | 514/333 |
| 5,399,585 A | 3/1995 | Alig et al. | 514/438 |
| 5,510,346 A | 4/1996 | Martin et al. | 514/221 |
| 5,698,691 A | 12/1997 | Yukimasa et al. | 540/490 |
| 5,773,646 A | 6/1998 | Michael et al. | 562/439 |
| 6,093,696 A | 7/2000 | Head et al. | 514/19 |
| 6,166,050 A | 12/2000 | Lombardo et al. | 514/352.18 |

FOREIGN PATENT DOCUMENTS

| | | |
|---|---|---|
| DE | 23 16 881 A | 10/1973 |
| DE | 28 37 264 A1 | 3/1979 |
| DE | 196 54 483 A | 1/1998 |
| EP | 0 031 104 A1 | 7/1981 |
| EP | 0 048 763 A1 | 4/1982 |
| EP | 0 144 230 A | 6/1985 |
| EP | 0 288 176 A | 10/1988 |
| EP | 0 322 068 A1 | 6/1989 |
| EP | 0 394 989 A2 | 10/1990 |
| EP | 0 498 268 A2 | 8/1992 |
| EP | 0 596 406 A1 | 5/1994 |
| EP | 0 710 657 A1 | 5/1996 |
| EP | 0 710 659 A1 | 5/1996 |
| EP | 0 842 943 A2 | 5/1998 |
| EP | 0 842 945 A2 | 5/1998 |
| JP | 56 090045 | 7/1981 |
| JP | 03 135962 | 6/1991 |
| WO | WO 86/02353 | 4/1986 |
| WO | WO 93/00095 | 1/1993 |
| WO | WO 93/08174 | 4/1993 |
| WO | WO 93/09795 | 5/1993 |
| WO | WO 94/15954 | 7/1994 |
| WO | WO 94/15955 | 7/1994 |
| WO | WO 94/29285 | 12/1994 |
| WO | WO 95/13811 | 5/1995 |

(List continued on next page.)

OTHER PUBLICATIONS

Hammadi, A., et al., "Diastereoselective hydrogenation of monodehydro enkephalins controlled by chiral rhodium catalysts," *Tetrahedron: Asymmetry,* 1992, 3(10), XP002106601, 1247–1262.

Nunami, K., et al., "A Novel Synthesis of methyl 1,5–disubstituted imidazole–4–carboxylates using 3–bromo–2–isocyanoacrylates," *J. Org. Chem.,* 1994, 59, XP002106602, 7635–7642.

Shimohigashi, Y., et al., "Dehydro–enkephalins," *Int. J. Peptide Protein Res.,* 1983, 21, XP002106600, 202–208.

(List continued on next page.)

*Primary Examiner*—Mukund J. Shah
*Assistant Examiner*—Tamthom N. Truong
(74) *Attorney, Agent, or Firm*—Woodcock Washburn LLP

(57) ABSTRACT

Squaric acid Derivatives of formula (1) are described:

(1)

wherein
$R^1$ is an integrin binding group;
$R^2$ is a hydrogen atom or a $C_{1-6}$alkyl group;
$L^1$ is a covalent bond or a linker atom or group;
n is zero or the integer 1;
$Alk^1$ is an optionally substituted aliphatic chain;
$R^3$ is a hydrogen atom or an optionally substituted heteroaliphatic, cycloaliphatic, heterocycloaliphatic, polycycloaliphatic, polyheterocycloaliphatic, aromatic or heteroaromatic group: and the salts, solvates, hydrates and N-oxides thereof.

The compounds are able to inhibit the binding of integrins to their ligands and are of use in the prophylaxis and treatment of immune of inflammatory disorders, or disorders involving the inappropriate growth or migration of cells.

22 Claims, No Drawings

FOREIGN PATENT DOCUMENTS

| | | |
|---|---|---|
| WO | WO 95/15973 | 6/1995 |
| WO | WO 95/19356 | 7/1995 |
| WO | WO 95/35314 | 12/1995 |
| WO | WO 96/01644 | 1/1996 |
| WO | WO 96/22966 | 8/1996 |
| WO | WO 96/26190 | 8/1996 |
| WO | WO 97/03094 | 1/1997 |
| WO | WO 97/08145 | 3/1997 |
| WO | WO 97/12866 | 4/1997 |
| WO | WO 97/23480 | 7/1997 |
| WO | WO 97/24124 | 7/1997 |
| WO | WO 97/31907 | 9/1997 |
| WO | WO 97/36858 | 10/1997 |
| WO | WO 97/36859 | 10/1997 |
| WO | WO 97/36861 | 10/1997 |
| WO | WO 97/36862 | 10/1997 |
| WO | WO 97/44333 | 11/1997 |
| WO | WO 97/47618 | 12/1997 |
| WO | WO 98/00395 | 1/1998 |
| WO | WO 98/04247 | 2/1998 |
| WO | WO 98/04913 | 2/1998 |
| WO | WO 98/18460 | 5/1998 |
| WO | WO 98/25892 | 6/1998 |
| WO | WO 98/31359 | 7/1998 |
| WO | WO 98/42662 | 10/1998 |
| WO | WO 98/53814 | 12/1998 |
| WO | WO 98/53817 | 12/1998 |
| WO | WO 98/53818 | 12/1998 |
| WO | WO 98/54207 | 12/1998 |
| WO | WO 98/58902 | 12/1998 |
| WO | WO 99/06390 | 2/1999 |
| WO | WO 99/06431 | 2/1999 |
| WO | WO 99/06432 | 2/1999 |
| WO | WO 99/06433 | 2/1999 |
| WO | WO 99/06434 | 2/1999 |
| WO | WO 99/06435 | 2/1999 |
| WO | WO 99/06436 | 2/1999 |
| WO | WO 99/06437 | 2/1999 |
| WO | WO 99/10312 | 3/1999 |
| WO | WO 99/10313 | 3/1999 |
| WO | WO 99/20272 | 4/1999 |
| WO | WO 99/26921 | 6/1999 |
| WO | WO 99/26922 | 6/1999 |
| WO | WO 99/26945 | 6/1999 |
| WO | WO 99/30709 | 6/1999 |
| WO | WO 99/31061 | 6/1999 |
| WO | WO 99/31099 | 6/1999 |
| WO | WO 99/32457 | 7/1999 |
| WO | WO 99/35163 | 7/1999 |
| WO | WO 99/36393 | 7/1999 |
| WO | WO 99/37618 | 7/1999 |
| WO | WO 99/43642 | 9/1999 |
| WO | WO 99/44994 | 9/1999 |
| WO | WO 99/48879 | 9/1999 |
| WO | WO 99/52879 | 10/1999 |
| WO | WO 99/52896 | 10/1999 |
| WO | WO 99/52898 | 10/1999 |
| WO | WO 99/60015 | 11/1999 |
| WO | WO 99/61465 | 12/1999 |
| WO | WO 99/64395 | 12/1999 |
| WO | WO 99/67230 | 12/1999 |
| WO | WO 00/00486 | 1/2000 |
| WO | WO 00/01383 | 1/2000 |
| WO | WO 00/06169 | 2/2000 |
| WO | WO 00/07544 | 2/2000 |
| WO | WO 00/17197 | 3/2000 |
| WO | WO 00/20396 | 4/2000 |
| WO | WO 00/31067 | 6/2000 |
| WO | WO 00/35855 | 6/2000 |
| WO | WO 00/73260 | 12/2000 |

OTHER PUBLICATIONS

Strange, P.G., et al., "Studies of enzyme–mediated reactions. Part II. Stereochemistry of the elimination of ammonia form L–tyrosine catalysed by the enzyme from maize," *J. Chem. Soc., Perkin I,* 1972, 18, XP002106603, 2364–2372.

WPI/Derwent No. XP002106604, Japanese Patent No. JP 60 190749 (Mitsui Toatsu Chem. Inc.), Sep. 28, 1985, 1 page, Abstract only.

Rico, J.G. et al., "A highly stereoslective michael addition to an α, β–unsaturated ester as the crucial step in the synthesis of a novel β–amino acid–containing fibrinogen receptor antagonist", *J. Org. Chem,* 1993, vol. 58, pp. 7948–7951.

Zablocki, J.A. et al., "Potent in vitro and in vivo inhibitors of platelet aggregation based upon the Arg–Gly–Asp sequences of fibrinogen", *J. Med. Chem.,* 1995, vol. 38, pp. 2378–2394.

Clausen, K., et al., "Studies on amino acids and peptides. II. Synthesis of protected endothiodipeptides," *J. Chem. Scr.,* 1982, 20(1–2), 14–18, doc. No. 97:163474 (abstract only, 1 page).

Frank, R., et al., "Extremely mild reagent for Boc deprotection," *J. Chem. Commun. (Cambridge),* 1996, 22, 2509–2510, doc. No. 126:104395 (abstract only, 3 pages).

Kobayashi, A., et al., "Syntheses of 2–dialkylamino–4, 4–disubstituted 5 (4H)–thiazolones," *J. Yakugaku Zasshi,* 1970, 90(11), 1377–1380, doc. No. 74–31713 (abstract only, 3 pages).

Koenig, H.B., et al., ".beta.–Lactam antibiotics," *Ger. Offen.,* 41 pages, doc. No. 83:97267 (abstract only, 5 pages), 1975.

Masuda, T., *Jpn. Kodai Tokkyo Koho,* 22 pages, doc. No. 115:280022 (abstract only, 1 page), 1991.

Pfeifer, T., et al., "Specific fragmentation of thioxo peptides facilitates the assignment of the thioxylated amino acid," *J. Mass Spectrom,* 1997, 32(10), 1064–1071, doc. No. 127:331738 (abstract only 2 pages).

Sawa, N., et al., "Preparation of 4(5)–thiocarbamoylimidazole compounds," *Jpn. Kokai Tokkyo Koho,* 33 pages, doc. No. 115–183296 (abstract only, 2 pages), 1991.

Schutkowski, M., et al., "Inhibition of peptidyl–prolyl cis/trans isomerase activity by substrate analog structures: thioxo tetrapeptide–4–nitroanilides," *Biochemistry,* 1995, 34(40), 13016–13026, doc. No. 123:221511 (abstract only, 4 pages).

"Cephalosporins," *Jpn. Kokai Tokkyo Koho,* 40 pages, doc. No. 99:5433 (abstract only, 2 pages), 1983.

Tsunematsu, H. et al., "Hydrolysis of phenylthiazolones of p–guanidinophenylalanine and arginine by trypsin and related enzymes," *J. Biochem.,* 1983, 94(4), 1119–1125.

Ukai, Y. et al., "A novel synthetic inhibitor of endopeptidase–24.15," *Chemical Abstracts,* 1997, 127(2).

Vanderslice, P. et al., "A Cyclic Hexapeptide is a Potent Antagonist of α4 Integrins," *J. Immunol.,* 1997, 158, 1710–1718.

Venturella, V.S. et al., "Substituted 1,3–Dihydro–4H–furo [3,4–d]–1,3–benzodiazepin–3–ones: Synthesis and Scope of the Method," *J. Heterocyclic Chem.,* 1969, 6(5), 671–679.

Yanagisawa, H. et al., WO 97/37970, "Preparation of phenylalkylcarboxylic acid derivatives lowering blood sugar level," *Chemical Abstracts,* 1997, Abstract 127:307307.

Yang, X., "A predominant role of integrin α4 in the spontaneous development of autoimmune diabetes in nonobese diabetic mice," *Proc. Natl. Acad. Sci. USA,* 1994, 91, 12604–12608.

Yednock, T.A., "Prevention of experimental autoimmune encephalomyelitis by antibodies against α4β1 integrin," Nature, 1992, 356, 63–66.

Whitlock, B.J. et al., "Structure and synthesis of lathyrine," J. Org. Chem. 1965, 30, 115–118.

Wojciechowaska, H. et al., "Preparation of 2,4–dinitrophenyl derivatives of tyrosine," Chemical Abstracts, 1968, 68(25), Abstract No. 114926r.

WPI/Derwent No. XP–002076854, Japanese Patent No. JP 56 04 193 895 A (Ajinomoto, K.K.), Jul. 13, 1992, DW9234, 1 Page. Abstract Only.

WPI/Derwent No. XP–002076855, Japanese Patent No. JP 56 049 373 A (Dainippon Pharm Co Ltd), May 2, 1981, DW8125, 1 Page, Abstract Only.

Osburn, L. et al., "Direct Expression Cloning of Vascular Cell Adhesion Molecule 1, a Cytokine–Induced Endothelial Protein that Binds to Lymphocytes," Cell, 1989, 59, 1203–1211.

Podolsky, D.K. et al., "Attenuation of Colitis in the Cotton–top Tamarin by Anti–α4 integrin Monoclonal Antibody," J. Clin. Invest., 1993, 92, 372–380.

Sakamoto, T., et al., "Condensed heteroaromatic ring systems. III. [1,2]synthesis of naphthyridine derivatives by cyclization of ethynylpyridinecarboxamides," Chem. Pharm. Bull. 1985, 33(2), 626–633.

Schultz, Von O.–E. et al., "Analogos of nucleic acid based as antimetabolites," Arzneimittel Forschung. Drug Res., 1967, 17(8), 1060–1064 (English summary included).

Shroff, H.N., et al., "Small peptide inhibitors of α4β7 mediated MadCAM–1 adhesion to lymphocytes," Barge. Med. Chem. Setts., 1996, 6(21), 2495–2500.

Sonnenberg, A., "Integrins and their ligands," Curr. Topics Microbiol. Immunol., 1993, 184, 7–3.

Springer, T.A., "Adhesion receptors of the immune system," Nature, 1990, 346, 425–434.

Springer, T.A., "Traffic Signals for Lymphocyte Recirculation and Leukocyte Emigration: The Multistep Paradigm," Cell, 1994, 76, 301–314.

Srivatsa, S.S., et al., "Selective αvβ3 integrin blockade potently limits neointimal hyperplasia and lumen stenosis following deep coronary arterial stent injury: evidence for the functional importance of integrin αvβ3 and osteopontin expression during neointima formation," Elsevier Science B.V., 1997, 36, 408–428.

Stupack, D.G., et al., "Induction of $\alpha_v\beta_3$ integrin–mediated attachment to extracellular matrix in $\beta_1$ integrin (CD29)–negative B cell lines," Experi. Cell Research, 1992, 203, 443–448.

Tan R., et al., "Synthesis of 2, 6–naphthyridine and some of its derivatives," Tetrahedron Letters, 1965, 31, 2737–2744.

Tous, G., et al., "O'–(Epoxyalkyl) tyrosines and (Epoxyalkyl) phenylalanine as irreversible inactivators of serine proteases: synthesis and inhibition mechanism," J. of Medicinal Chemistry, 1990, 33(6), 1620–1634.

Li, Z. et al., "Effect of an anti–Mo1 MAb on ozone–induced airway inflammation and airway hyperresponsiveness in dogs," Am. J. Physiol., 1992, 263(6 Pt 1), L723–726.

Marlin, S.D. et al., "LFA–1 Immunodeficiency Disease," J. Exp. Med., 1986, 164, 855–867.

Masahiko, N., Japanese Patent No. 57–080370 published May 19, 1982, "Alpha–Methylcinnamic Acid Derivative, its Preparation and Antilipemic Agent Containing The Same," Patent Abstracts of Japan, 1982.

McDowell, R.S. et al., "From Peptide to Non–Peptide. 2. The de Novo Design of Potent, Non–Peptidal Inhibitors of Platelet Aggregation Based on a Benzodiazepinedione Scaffold," J. Am. Chem. Soc., 1994, 116, 5077–5083.

Miller, W.H. et al., "Structure–Activity Relationships in 3–Oxo–1,4–Benzodiazepine–2–Acetic Acid GPIIb/IIIa Antagonists. The 2–Benzazepine Series," Bioorg. Med. Chem. Lett., 1996, 6(21), 2481–2486.

Mitjans, F., et al., "An anti–αv–integrin antibody that blocks integrin function inhibits the development of a human melanoma in nude mice," J. Cell Science, 1995, 108, 2825–2838.

Molina, P., et al., "Iminophosphorane–mediated annelation of a pyridine ring into a preformed pyridine one: synthesis of naphthyridine, pyrido [1,2–c] pyrimidine and pyrido [1,2–c] quinazoline derivatives," Tetrahedron, 1992, 48(22), 4601–4616.

Nagasawa, H.T. et al., "β–Substituted Cysteines as Sequestering Agents for Ethanol–Derived Acetaldehyde in Vivo," J. Med. Chem., 1987, 30, 1373–1378.

Noike, Y., "Synthesis of Quinolizine Derivatives. VI. Synthesis of 3–Aminoquinolizines. (1). Synthesis of dl–3–Amino–, dl–3–epi–Amino–, and dl–3–epi–Dimethylaminoquinolizidines," Yakugaku Zasshi, 1959, 79(12), 1514–1518 (English summary included).

Numata, A., et al., "General synthetic method for naphthyridines and their N–oxides containing isoquinolinic nitrogen," Synthesis, 1999, 2, 306–311.

Ohki, S. et al., "Synthesis of quinolizine derivatives. V. Studies on Diastereoisomer of Ethyl 3–Quinolizidinecarboxylate," Chem. Pharm. Bull., 1959, 7(6), 708–712.

Osborne, L., "Leukocyte Adhesion to Endothelium in Inflammation," Cell, 1990, 62, 3–6.

Hammes, H., et al., "Subcutaneous injection of a cyclic peptide antagonist of vitronectin receptor–type integrins inhibits retinal neovascularization," Nature Medicine, 1996, 2, 529–533.

Harris, R.L.N. et al., Aust. J. Chem., "Potential wool growth inhibitors. 2(1H)–Pyridone analogs of mimosine," 1977, 30(3), 649–655.

Hartke, K. et al., "Dithio and thiono esters. Part 61. Synthesis of α–amino dithioesters and endothiodipeptides,", J. Prakt. Chem., 1996, 338(3), 251–256.

Holzmann, B., et al., "Peyer's patch–specific lymphocyte homing receptors consist of a VLA–4–like α VLA–4–like α chain associated with either of two integrin β chains, one of which is novel," EMBO J., 1989, 8(6), 1735–1741.

Humphries, M.J. et al., "Mechanisms of VCAM–1 and fibronectin binding to integrin $\alpha_4\beta_1$: implications for integrin function and rational drug design," Ciba Foundation Symposium, 1995, 189, 177–194.

Issekutz, T.B., "Inhibition of lymphocyte Endothelial Adhesion and In Vivo Lymphocyte Migration to Cutaneous Inflammation by TA–3, a New Monoclonal Antibody to Rat LFA–1," J. Immunol., 1992, 149(10), 3394–3402.

Jaynes, B.H. et al., "Synthesis and In Vivo Antibacterial Activity of Hygromycin a Analogs Modified at the $C_4$' Aryl Position," Bioorg. Med. Chem. Letts., 1993, 3(8), 1531–1536.

Jepson, J.B. et al., "Reactions of α–Thioacylamino–acids. Their conversion into Thiazolones and Derivatives Therof," J. Chem. Soc., 1955, 1791–1797.

Kalvin, D.M., et al., "/stbtgesus if (4R)–D,L–[4–$^2$H]– and (4S)–D,L–[4–$^2$H]homoserine lactones," *J. Org. Chem.*, 1985, 50, 2259–2263.

Keenan, R.M. et al., "Discovery of Potent Nonpeptide Vitronectin Receptor (av$\beta_3$) Antagonists," *J. Med. Chem.*, 1997, 40(15), 2289–2292.

Koivunen, E., et al., "Selection of peptides binding to the $\alpha_5\beta_1$ integrin from phage display library," *J. Biological Chemistry*, 1993, 268(27), 20205–20210.

Lei, H. et al., "Efficient Synthesis of a Phosphinate Bis–Amino Acid and Its Use in the Construction of Amphiphilic Peptides," *J. Org. Chem.*, 1994, 59, 4206–4210.

Buckle, D.R., et al., "Non Thiazolidinedione Antihyperglycaemic Agents. 1: $\alpha$–Heteroatom Substituted $\beta$–Phenylpropanoic Acids," *Bioorg. Med. Chem. Lett.*, 1996, 6(17), 2121–2126.

Cardarelli, P.M. et al., "Cyclic RGD Peptide Inhibits $\alpha 4\beta 7$ Interaction with Connecting Segment 1 and Vascular Cell Adhesion Molecule," *J. Biol. Chem.*, 1994, 269(28), 18668–18673.

*Chemical Abstracts*, "N–[4–Thiazolidinyl)carbonyl]amino acid derivatives," 1981, 95(19), Abstract No. 169173f.

Comprehensive Organic Functional Group Transformations, Katritzky, A.R., et al. (Eds.), Pergamon, 1995.

Corey, E.J. et al., "A Synthetic Method for Formyl→Ethynyl Conversion (RCHO→RC≡CH or RC≡CR')," *Tetrahedron Lett.*, 1972, 36, 3769–3772.

Cornforth, J.W., "Oxazoles and Oxazolones," *Chem. Penicillin*, Princeton Book Review, 1949, pp. 688–799, and 800.

Davies, St.G., et al., "Asymmetric synthesis of R–$\beta$–amino butanoic acid and S–$\beta$–tyrosine: homochiral lithium amide equivalents for Michael additions to $\alpha,\beta$–unsaturated esters," *Tetra. Asymmetry*, 1991, 2(3), 183–186.

Encyclopedia of Reagents for Organic Synthesis, *John Wiley and Sons* (eds.), 1995.

Ferguson, T.A. et al., "Two integrin–binding peptides abrogate T cell–mediated immune responses in vivo," *Proc. Natl. Acad. Sci. USA*, 1991, 88, 8072–8076.

Fu, H. et al., "Preliminary study on synthesis and antitumor activity in vitro of derivatives of timonacic," *Chemicals Abstracts*, 1988, 108(17), Abstract No. 150358k.

Giacomello, et al., "Synthesis of 2,6–naphthyridine," *Tetra. Letters*, 1965, 16, 1117–1121.

Green, T.W., "Protective Groups in Organic Synthesis," *John Wiley and Sons* (eds.), 1991.

Abraham, W. M. et al., "$\alpha_4$–Integrins Mediate Antigen–Induced Late Bronchial Responses and Prolonged Airway Hyperresponsiveness in Sheep," *J. Clin. Invest.*, 1994, 93, 776–787.

Alhaique, F., et al., "Cyclisation of dinitriles by sodium alkoxides a new synthesis of naphthyridines," *Tetrahedron Letters*, 1975, 3, 17.

Ames, D.E., et al., "Condensation of $\beta$–dicarbonyl compounds with halogenopyridinecarb–oxylic acids. A convenient synthesis of some naphthyridine derivatives," *J.C.S. Perkisn I*, 1972, 705–710.

Azzouny, A.E., et al., "Synthesis of some N–substituted salicylamides structurally related to certain antimicrobials," *Pharmazie*, 1977, 32(6), 318–323 (abstract).

Bach et al., "Anomalous optical rotation and circular dichroism of N–thioacylated.alpha.–amino acids and deriva," *Acta Chem. Scand.*, 1966, 20(10), 2781–2794.

Badshah, A., et al., "Catalytic reduction of azlactones in alkaline media. Synthesis of amino acids," *J. of Organic Chemistry*, 1972, 37(18), 2916–2918.

Barrett, G.C., "Circular dichroism of N–thiobenzoyl–1–$\alpha$–amino acids. III. Their circular dichroism through the near–ultraviolet wavelength range," *J. Chem. Soc.*, 1967, Section C, 1–5.

Berlin, C. et al., "$\alpha 4\beta 7$ Integrin Mediates Lymphocyte Binding to the Mucosal Vascular Addressin MAdCAM–1," *Cell*, 1993, 74, 185–195.

Binns, R.M. et al., "The Role of E–Selectin in Lymphocyte and Polymorphonuclear Cell Recruitment into Cutaneous Delayed Hypersensitivity Reactions in Sensitized Pigs," *J. Immunol.*, 1996, 157, 4094–4099.

Briskin, M.J. et al., "Structural Requirements for Mucosal Vascular Addressin Binding to Its Lymphocyte Receptor $\alpha_4\beta_7$," *J. Immunol.*, 1996, 156, 719–726.

Brooks, Peter C., et al., "Antiintegrin $\alpha v\beta 3$ blocks human breast cancer growth and angiogenesis in human skin," *j. Clin. Invest.*, 1995, 96, 1815–1822.

Lobb, R.R., et al., "Small molecule antagonists of alpha4 integrins: novel drugs for asthma," *Exp. Opin. Invest. Drugs*, 1999, XP000885957, 8(7), 935–945.

Samanen, J., et al., "Vascular indications for integrin alpha V antagonists," *Current Pharm. Design.*, 1997, 3, 545–584.

Šavrda, J., "CIS–TRANS isomerism of N–ACYL derivatives of proline and its analogues, linear peptides with CIS peptide bonds," *Proc. 14$^{th}$ European Peptide Symposium*, Loffet, A. (ed.), 1976, 653–656.

SQUARIC ACID DERIVATIVES

This invention relates to a series of squaric acid derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T A. Nature, 346, 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus the integrin termed $\alpha 4\beta 1$ consists of the integrin alpha 4 chain associated with the integrin beta 1 chain, but is also widely referred to as Very Late Antigen 4 or VLA4.

Some integrin chains are capable of pairing with more than one partner. For example, the $\alpha_v$ chain has been reported to pair with the beta 1 chain, the beta 3 chain, the beta 5 chain, the beta 6 chain and the beta 8 chain to give molecules which bind to different sets of ligands and which are referred to respectively as the integrins aver $\alpha_v\beta_1$, $\alpha_v\beta_3$, $\alpha_v\beta_5$, $\alpha_v\beta_6$, and $\alpha_v\beta_8$. Not all of the potential pairings of integrin alpha and beta chains have yet been observed in nature and the integrin family has been subdivided into a number of subgroups based on the pairings that have been recognised [Sonnenberg, A ibid].

The importance of integrin function in normal physiological responses is highlighted by two human deficiency diseases in which integrin function is defective. Thus in the disease termed Leukocyte Adhesion Deficiency (LAD) there is a defect in one of the families of integrins expressed [on leukocytes. Patients suffereing from this disease have a reduced ability to recruit leukocytes to inflammatory sites and suffer recurrent infections which in extreme cases may be fatal. In the case of patients suffering from the disease termed Glanzman's thrombasthenia (a defect in a member of the beta 3 integer famly) there is a defect in blood clotting.

The potential to modify integrin function in such a way as to beneficially modulate cell adhesion has been extensively investigated in animal models using specific monoclonal antibodies and peptides that block various functions of these molecules [e.g. Issekutz, T. B. J. Immunol. 3394, (1992); Li, Z. et al Am. J. Physiol. 263, L723, (1992); Mitjans et al J. Cell Sci. 108, 2825 (1995), Brooks P. C. et al J. Clin. Invest. 96, 1815 (1995), Binns, R. M. et al J. Immunol. 157,4094, (1996), Hammes, H-P, et al Nature Medicine 2, 529 (1996), Srivata, S. et al Cardiovascular Res. 36, 408 (1997)]. A number of monoclonal antibodies which block integrin function are currently being investigated for their therapeutic potential in human disease.

Inhibition of integrin-mediated cell interaction can be expected to be beneficial in a number of disease states, and in addition to the monoclonal antibodies and peptides just mentioned there has been great interest in selective low molecular weight inhibitors of integrin function. Thus, for example selective $\alpha_4$ integrin inhibitors have been described in International patent Specifications Nos. WO96/22966, WO97/03094, WO 98/04247, WO98/04913, WO98/53814, WO98/53817, WO98/53818, WO98/54207, WO98/58902, WO99/06390, WO99/064310–6437, WO99/10312, WO99/10313, WO99/67230, WO 99/26922, WO99/60015, WO99/26921, WO9936393, WO99/52898 and WO99/64395. Numerous selective $\alpha_v$ integrin inhibitors have also been described, for example in International Patent Specifications Nos. WO97/08145, WO97/23480, WO97/36858, WO97136859, WO97/36861, WO97136862, WO97/44333, WO97/47618, WO98/31359, WO98/25892, WO98/18460, WO99/44994, WO99/30709, WO99/31061, WO 99/26945, WO99/52896, WO99/52879, WO99/32457, WO99/31099, WO00/07544, WO00/00486, WO00/06169, WO00/17197 and WO00/01383.

While it is clearly possible to obtain selective integrin inhibitors, their usefulnesses in medicine may be limited due to poor pharmacokinetic properties. Thus, for example, in our hands, integrin inhibitors falling within the general structural types featured in the above-mentioned patent specifications are not particularly attractive for development as medicines since they can be cleared rapidly from the body. In order to overcome this problem we have made use of a squaric acid framework which can be readily adapted to provide potent and selective integrin inhibitors using recognised integrin binding groups (for example as described herein and in the patent specifications listed above), which advantageously possess good pharmacokinetic properties, especially low plasma clearance.

Thus according to one aspect of the invention we provide a compound of formula (1)

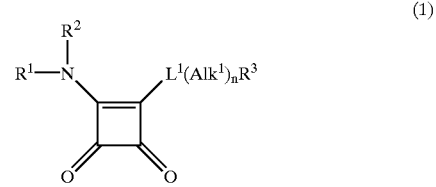

wherein $R^1$ is an integrin binding group;

$R^2$ is a hydrogen atom or a $C_{1-6}$alkyl group;

$L^1$ is a covalent bond or a linker atom or group;

n is zero or the integer 1;

$Alk^1$ is an optionally substituted aliphatic chain;

$R^3$ is a hydrogen atom or an optionally substituted heteroaliphatic, cycloaliphatic, heterocycloaliphatic, polycycloaliphatic, polyheterocycloaliphatic, aromatic or heteroaromatic group: and the salts, solvates, hydrates and N-oxides thereof.

It will be appreciated that compounds of formula (1) may have one or more chiral centres, and exist as enantiomers or diastereomers. The invention is to be understood to extend to all such enantiomers, diastereomers and mixtures thereof, including racemates. Formula (1) and the formulae hereinafter are intended to represent all individual isomers and mixtures thereof, unless stated or shown otherwise.

In the compounds according to the invention, integrin-binding groups represented by $R^1$ include for example those which are able to bind $\alpha_4$- or $\alpha_v$-integrins. Particular examples of such integrins include $\alpha_4\beta_1$, $\alpha_4\beta_7$ and $\alpha_v\beta_3$ integrins.

In general, the term integrin-binding group is used herein in relation to $R^1$ to mean any group which when part of the compound of formula (1) is able to interact with an integrin to modulate cell adhesion in vivo and achieve a therapeutic response. Typically the $R^1$ group may bind to the integrin in such a way that it modulates the interaction of the integrin with its ligand. Thus for example the $R^1$ group may inhibit binding of the ligand and decrease cell adhesion. Such a response enables appropriate $R^1$ groups to be readily identified using small scale routine in vitro screening assays to determine the degree of inhibition of integrin-ligand binding in the presence of a compound of formula (1). Examples of such screening assays are widely reported in the literature, for example in the papers and International patent specifications described above, and in the Examples hereinafter.

Thus in general $R^1$ may be any group which when present in a compound of formula (1) is able to bind to an integrin such that the compound of formula (1) inhibits the binding of the integrin with its ligand with an $IC_{50}$ of 10 $\mu M$ or below, particularly 1 $\mu M$ or below, especially 500 nM or below, e.g. in the range 0.001–500 nM.

Particular $R^1$ groups in compounds of the invention include those of formula $Ar^1L^2Ar^2Alk$- wherein $Ar^1$ is an optionally substituted aromatic or heteroaromatic group, $L^2$ is a linker atom or group, $Ar^2$ is an optionally substituted phenylene or nitrogen-containing six-membered heteroarylene group and Alk is a chain:

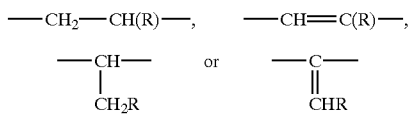

where R is a carboxylic acid ($—CO_2H$) or a derivative or biostere thereof.

$R^1$ groups of this type are particularly useful for binding $\alpha_4$ integrins and compounds of formula (1) incorporating the $Ar^1L^2Ar^2Alk$- function can be expected to inhibit $\alpha_4$ integrins such as $\alpha_4\beta_1$ and/or $\alpha_4\beta_7$ at concentrations at which they generally have no or minimal inhibitory action on integrins of other a subgroups. Such compounds are of use in medicine, for example in the prophylaxis and treatment of immune or inflammatory disorders as described hereinafter.

Optionally substituted aromatic groups represented by $Ar^1$ when present in the group $R^1$ include for example optionally substituted monocyclic or bicyclic fused ring $C_{6-12}$ aromatic groups, such as phenyl, 1- or 2-naphthyl, 1- or 2-tetrahydronaphthyl, indanyl or indenyl groups.

Optionally substituted heteroaromatic groups represented by the group $Ar^1$ when present in the group $R^1$ include for example optionally substituted $C_{1-9}$ heteroaromatic groups containing for example one, two, three or four heteroatoms selected from oxygen, sulphur or nitrogen atoms. In general, the heteroaromatic groups may be for example monocyclic or bicyclic fused ring heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example eight- to thirteen-membered fused-ring heteroaromatic groups containing one, two or more heteroatoms selected from oxygen, sulphur or nitrogen atoms.

Particular examples of heteroaromatic groups of these types include pyrrolyl, furyl, thienyl, imidazolyl, N—$C_{1-16}$alkylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, [2,3-dihydro]benzothienyl, benzothienyl, benzotriazolyl, indolyl, isoindolyl, benzimidazolyl, imidazo[1,2-a]pyridyl, benzothiazolyl, benzoxazolyl, benzopyranyl, [3,4-dihydro] benzopyranyl, quinazolinyl, quinoxalinyl, naphthyridinyl, especially 2,6-naphthyridinyl, pyrido[3,4-b]pyridyl, pyrido [3,2-b]pyridyl, pyrido[4,3-b]-pyridyl, quinolinyl, isoquinolinyl, tetrazolyl, 5,6,7,8-tetrahydroquinolinyl, 5,6,7,8-tetrahydroisoquinolinyl, and imidyl, e.g. succinimidyl, phthalimidyl, or naphthalimidyl such as 1,8-naphthalimidyl.

Each aromatic or heteroaromatic group represented by the group $Ar^1$ may be optionally substituted on any available carbon or, when present, nitrogen atom. One, two, three or more of the same or different substituents may be present and each substituent may be selected for example from an atom or group —$L^3(Alk^2)_tL^4(R^4)_u$ in which $L^3$ and $L^4$, which may be the same or different, is each a covalent bond or a linker atom or group, t is zero or the integer 1, u is an integer 1, 2 or 3, $Alk^2$ is an aliphatic or heteroaliphatic chain and $R^4$ is a hydrogen or halogen atom or a group selected from optionally substituted $C_{1-6}$alkyl or $C_{3-8}$ cycloalkyl, —$OR^5$ [where $R^5$ is a hydrogen atom, an optionally substituted $C_{1-6}$alkyl or $C_{3-8}$ cycloalkyl group], —$SR^5$, —$NR^5R^6$ [where $R^6$ is as just defined for $R^5$ and may be the same or different], —$NO_2$, —CN, —$CO_2R^5$, —$SO_3H$, —$SOR^5$, —$SO_2R^5$, —$SO^3R^5$, —$OCO_2R^5$, —$CONR^5R^6$, —$OCONR^5R^6$, —$CSNR^5R^6$, —$COR^5$, —$OCOR^5$, —$N(R^5)COR^6$, —$N(R^5)CSR^6$, —$SO_2N(R^5)(R^6)$, —$N(R^5)SO_2R^6$, $N(R^5)CON(R^6)(R^7)$ [where $R^7$ is a hydrogen atom, an optionally substituted $C_{1-6}$alkyl or $C_{3-8}$cycloalkyl group], —$N(R^5)CSN(R^6)(R^7)$ or —$N(R^5)SO_2N(R^6)(R^7)$, provided that when t is zero and each of $L^3$ and $L^4$ is a covalent bond then u is the integer 1 and $R^4$ is other than a hydrogen atom.

When $L^3$ and/or $L^4$ is present in these substituents as a linker atom or group it may be any divalent linking atom or group. Particular examples include —O— or —S— atoms or —C(O)—, —C(O)O—, —OC(O)—, —C(S)—, —S(O)—, —S(O)$_2$—, —N($R^8$)— [where $R^8$ is a hydrogen atom or an optionally substituted $C_{1-6}$alkyl group], —N($R^8$) O—, —N($R^8$)N—, —CON($R^8$)—, —OC(O)N($R^8$)—, —CSN($R^8$)—, —N($R^8$)CO—, —N($R^8$)C(O)O—, —N($R^8$) CS—, —S(O)$_2$N($R^8$)—, —N($R^8$)S(O)$_2$—, —N($R^8$)CON ($R^8$)—, —N($R^8$)CSN($R^8$)—, or —N($R^8$)SO$_2$N($R^8$)— groups. Where the linker group contains two $R^8$ substituents, these may be the same or different.

When $R^4$, $R^5$, $R^6$, $R^7$ and/or $R^8$ is present as a $C_{1-6}$alkyl group it may be a straight or branched $C_{1-6}$alkyl group, e.g. a $C_{1-3}$alkyl group such as a methyl or ethyl group. $C_{3-8}$cycloalkyl groups represented by $R^4$, $R^5$, $R^6$, $R^7$ and/or $R^8$ include $C_{3-6}$cycloalkyl groups e.g. cyclopropyl, cyclobutyl, cyclopentyl and cyclohexyl groups. Optional substituents which may be present on such alkyl and cycloalkyl groups include for example one, two or three substituents which may be the same or different selected from halogen atoms, for example fluorine, chlorine, bromine or iodine atoms, or hydroxy or $C_{1-6}$alkoxy e.g. methoxy or ethoxy groups.

When the groups $R^5$ and $R^6$ or $R^6$ and $R^7$ are both $C_{1-6}$alkyl groups these groups may be joined, together with the N atom to which they are attached, to form a heterocyclic ring. Such heterocyclic rings may be optionally interrupted by a further heteroatom selected from —O—, —S— or —N($R^5$)—. Particular examples of such heterocyclic rings include piperidinyl, morpholinyl, thiomorpholinyl, pyrrolidinyl, imidazolidinyl and piperazinyl rings.

When $Alk^2$ is present as an aliphatic or heteroaliphatic chain it may be for example any divalent chain corresponding to the below-mentioned aliphatic or heteroaliphatic group described for $Alk^1$ or $R^3$ respectively.

Halogen atoms represented by $R^4$ in the optional $Ar^1$ substituents include fluorine, chlorine, bromine, or iodine atoms.

Examples of the substituents represented by $-L^3(Alk^2)_tL^4(R^4)_u$ when present in $Ar^1$ groups in compounds of the invention include atoms or groups $-L^3Alk^2L^4R^4$, $-L^3Alk^2R^4$, $-L^3R^4$, $-R^4$ and $-Alk^2R^4$ wherein $L^3$, $Alk^2$, $L^4$ and $R^4$ are as defined above. Particular examples of such substituents include $-L^3CH_2L^4R^4$, $-L^3CH(CH_3)L^4R^4$, $-L^3CH(CH_2)_2L^4R^4$, $-L^3CH(CH_3)R^4$, $-L^3(CH_2)_2R^4$, $-CH_2R^4$, $-CH(CH_3)R^4$, $-(CH_2)_2R^4$ and $-R^4$ groups.

Thus $Ar^1$ in compounds of the invention may be optionally substituted for example by one, two, three or more halogen atoms, e.g. fluorine, chlorine, bromine or iodine atoms, and/or $C_{1-6}$alkyl, e.g. methyl, ethyl, n-propyl, ipropyl, n-butyl or t-butyl, $C_{3-8}$cycloalkyl, e.g. cyclopropyl, cyclobutyl, cyclopentyl or cyclohexyl, $C_{1-6}$hydroxyalkyl, e.g. hydroxymethyl, hydroxyethyl or $-C(OH)(CF_3)_2$, carboxy$C_{1-6}$alkyl, e.g. carboxyethyl, $C_{1-6}$alkylthio e.g. methylthio or ethylthio, carboxy$C_{1-6}$alkylthio, e.g. carboxymethylthio, 2-carboxyethylthio or 3-carboxypropylthio, $C_{1-6}$alkoxy, e.g. methoxy or ethoxy, hydroxy$C_{1-6}$alkoxy, e.g. 2-hydroxyethoxy, halo$C_{1-6}$alkyl, e.g. $-CF_3$, $-CHF_2$, $CH_2F$, halo$C_{1-6}$alkoxy, e.g. $-OCF_3$, $-OCHF_2$, $-OCH_2F$, $C_{1-6}$alkylamino, e.g. methylamino or ethylamino, amino ($-NH_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$ dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, isopropylaminoethoxy, or dimethylaminopropoxy, nitro, cyano, amidino, hydroxyl ($-OH$), formyl [HC(O)—], carboxyl ($-CO_2H$), $-CO_2Alk^3$ [where $Alk^3$ is as defined below for $Alk^7$], $C_{1-6}$alkanoyl e.g. acetyl, thiol ($-SH$), thio$C_{1-6}$alkyl, e.g. thiomethyl or thioethyl, sulphonyl ($-SO_3H$), $-SO_3Alk^3$, $C_{1-6}$alkylsulphinyl, e.g. methylsulphinyl, $C_{1-6}$alkylsulphonyl, e.g. methylsulphonyl, aminosulphonyl ($-SO_2NH_2$), $C_{1-6}$alkylaminosulphonyl, e.g. methylaminosulphonyl or ethylaminosulphonyl, $C_{1-6}$dialkylaminosulphonyl, e.g. dimethylaminosulphonyl or diethylaminosulphonyl, phenylaminosulphonyl, carboxamido ($-CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylamino$C_{1-6}$alkylaminocarbonyl, e.g. diethylaminoethylaminocarbonyl, aminocarbonylamino, $C_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl$C_{1-6}$alkylamino, e.g. ethylaminothiocarbonylmethylamino, $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino ($-NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, $C_{1-6}$alkoxycarbonylamino, e.g. methoxycarbonylamino, ethoxycarbonylamino or t-butoxycarbonylamino groups.

$L^2$ when present as part of the group $R^1$ in compounds of the invention may be a linker atom or group $L^{2a}$ or a linker -$Alk^a(L^{2a})_y$—, where $Alk^a$ is an optionally substituted aliphatic or heteroaliphatic chain as previously defined for $Alk^2$, and $L^{2a}$ is a linker atom or group as described above for $L^3$ and $L^4$ and y is zero or the integer 1.

Optionally substituted nitrogen-containing six-membered heteroarylene groups represented by $Ar^2$ when present as part of the group $R^1$ include optionally substituted pyridiyl, pyrimidindiyl, pyridazindiyl, pyrazindiyl and triazindiyl groups. Each group may be attached to the remainder of the molecule through any available ring carbon atoms.

The phenylene and nitrogen-containing heteroarylene groups represented by $Ar^2$ may be optionally substituted by one or two substituents selected from the atoms or groups $-L^3(Alk^2)_tL^4(R^4)_u$ described herein. Where two of these atoms or groups are present they may be the same or different.

When the group R is present in $R^1$ in compounds of the invention as a derivative of a carboxylic acid it may be for example a carboxylic acid ester or amide. Particular esters and amides include $-CO_2Alk^7$ and $-CONR^5R^6$ groups as defined herein. When R is a biostere of a carboxylic acid it may be for example a tetrazole or other acid such as phosphonic acid, phosphinic acid, sulphonic acid, sulphinic acid or boronic acid or an acylsulphonamide group.

When the group $R^2$ is present in compounds of the invention as a $C_{1-6}$alkyl group it may be for example a straight or branched $C_{1-6}$alkyl group, e.g. a $C_{1-3}$alkyl group such as a methyl or ethyl group.

The linker atom or group represented by $L^1$ in compounds of formula (1) may be any linker atom or group as described above for the linker atom or group $L^3$.

When the group $Alk^1$ is present in compounds of formula (1) as an optionally substituted aliphatic chain it may be an optionally substituted $C_{1-10}$ aliphatic chain. Particular examples include optionally substituted straight or branched chain $C_{1-6}$ alkylene, $C_{2-6}$ alkenylene, or $C_{2-6}$ alkynylene chains.

Particular examples of aliphatic chains represented by $Alk^1$ include optionally substituted $-CH_2-$, $-(CH_2)_2-$, $-CH(CH_3)CH_2-$, $-(CH_2)_2CH_2-$, $-(CH_2)_3CH_2-$, $-CH(CH_3)(CH_2)_2-$, $-CH_2CH(CH_3)CH_2-$, $-C(CH_3)_2CH_2-$ $-CH_2C(CH_3)_2CH_2-$,$-(CH_2)_2C(CH_3)_2$ $CH_2-$, $-(CH_2)_4CH_2-$, $-(CH_2, -CHCH-$, $-CHCHCH_2-$, $-CH_2-CHCH-$, $-CHCHCH_2CH_2-$, $-CH_2CHCHCH_2-$, $-(CH_2)_2CHCH-$, $-CC-$, $-CCCH_2-$, $-CH_2CC-$, $-CCCH_2CH_2-$, $-CH_2CCCH_2-$ or $-(CH_2)_2CCH-$ groups.

Heteroaliphatic groups represented by the group $R^3$ in the compounds of formula (1) include the aliphatic chains just described for $Alk^1$ but with each containing a terminal hydrogen atom and additionally containing one, two, three or four heteroatoms or heteroatom-containing groups. Particular heteroatoms or groups include atoms or groups $L^5$ where $L^5$ is as defined above for $L^3$ when $L^3$ is a linker atom or group. Each $L^5$ atom or group may interrupt the aliphatic group, or may be positioned at its terminal carbon atom to connect the group to an adjoining atom or group.

Particular examples include optionally substituted —$L^5CH_3$, —$CH_2L^5CH_3$, —$L^5CH_2CH_3$, —$CH_2L^5CH_2CH_3$, —$(CH_2)_2L^5CH_3$, —$(CH_2)_3L^5CH_3$, and —$(CH_2)_2L^5CH_2CH_3$ groups.

The optional substituents which may be present on aliphatic or heteroaliphatic chains represented by $Alk^1$ and $R^3$ respectively include one, two, three or more substituents where each substituent may be the same or different and is selected from halogen atoms, e.g. fluorine, chlorine, bromine or iodine atoms, or —OH, —$CO_2H$, —$CO_2R^9$, where $R^9$ is an optionally substituted straight or branched $C_{1-6}$alkyl group as defined above for $R^4$, —$CONHR^9$, —$CON(R^a)_2$, —$COCH_3$, $C_{1-6}$alkoxy, e.g. methoxy or ethoxy, thiol, —$S(O)R^9$, —$S(O)2R^9$, $C_{1-6}$alkylthio e.g. methylthio or ethylthio, amino or substituted amino groups. Substituted amino groups include —$NHR^9$ and —$N(R^9)_2$ groups. Where two $R^9$ groups are present in any of the above substituents these may be the same or different.

Optionally substituted cycloaliphatic groups represented by the group $R^3$ in compounds of the invention include optionally substituted $C_{3-10}$ cycloaliphatic groups. Particular examples include optionally substituted $C_{3-10}$ cycloalkyl, e.g. $C_{3-7}$ cycloalkyl or $C_{3-10}$ cycloalkenyl, e.g $C_{3-7}$ cycloalkenyl groups.

Optionally substituted heterocycloaliphatic groups represented by the group $R^3$ include optionally substituted $C_{3-10}$heterocycloaliphatic groups. Particular examples include optionally substituted $C_{3-10}$heterocycloalkyl, e.g. $C_{3-7}$ heterocycloalkyl, or $C_{3-10}$heterocycloalkenyl, e.g. $C_{3-7}$ hetercycloalkenyl groups, each of said groups containing one, two, three or four heteroatoms or heteroatom-containing groups $L^5$ as defined above. Optionally substituted polycycloaliphatic groups represented by the group $R^3$ include optionally substituted $C_{7-10}$ bi- or tricycloalkyl or $C_{7-10}$bi- or tricycloalkenyl groups. Optionally substituted polyheterocycloaliphatic groups represented by the group $R^3$ include the optionally substituted polycycloalkyl groups just described, but with each group additionally containing one, two, three or four $L^5$ atoms or groups.

Particular examples of cycloaliphatic, polycycloaliphatic, heterocycloaliphatic and polyheterocycloaliphatic groups represented by the group $R^3$ include optionally substituted cyclopropyl, cyclobutyl, cyclopentyl, cyclohexyl, cycloheptyl, 2-cyclobuten-1-yl, 2-cyclopenten-1-yl, 3-cyclopenten-1-yl, adamantyl, norbornyl, norbornenyl, tetrahydrofuranyl, pyrroline, e.g. 2- or 3-pyrrolinyl, pyrrolidinyl, pyrrolidinone, oxazolidinyl, oxazolidinone, dioxolanyl, e.g. 1,3-dioxolanyl, imidazolinyl, e.g. 2-imidazolinyl, imidazolidinyl, pyrazolinyl, e.g. 2-pyrazolinyl, pyrazolidinyl, pyranyl, e.g. 2- or 4-pyranyl, piperidinyl, piperidinone, 1,4-dioxanyl, morpholinyl, morpholinone, 1,4-dithianyl, thiomorpholinyl, piperazinyl, 1,3,5-trithianyl, oxazinyl, e.g. 2H-1,3-, 6H-1,3-, 6H-1,2-, 2H-1,2- or 4H-1,4-oxazinyl, 1,2,5-oxathiazinyl, isoxazinyl, e.g. o- or p-isoxazinyl, oxathiazinyl, e.g. 1,2,5 or 1,2,6-oxathiazinyl, or 1,3,5,-oxadiazinyl groups.

The optional substituents which may be present on the cycloaliphatic, polycycloaliphatic, heterocycloaliphatic or polyheterocycloaliphatic groups represented by the group $R^3$ include one, two, three or more substituents each selected from halogen atoms, e.g. fluorine, chlorine, bromine or iodine atoms, or $C_{1-6}$alkyl, e.g. methyl or ethyl, halo$C_{1-6}$alkyl, e.g. halomethyl or haloethyl such as difluoromethyl or trifluoromethyl, optionally substituted by hydroxyl, e.g. —$C(OH)(CF_3)_2$, $C_{1-6}$alkoxy, e.g. methoxy or ethoxy, halo$C_{1-6}$alkoxy, e.g. halomethoxy or haloethoxy such as difluoromethoxy or trifluoromethoxy, thiol, $C_{1-6}$alkylthio e.g. methylthio or ethylthio, or -(Alk$^4$)$_v$R$^{10}$ groups in which Alk$^4$ is a straight or branched $C_{1-3}$alkylene chain, v is zero or an integer 1 and $R^{10}$ is a —OH, —SH, —$N(R^{11})_2$, (in which $R^{11}$ is an atom or group as defined herein for $R^8$)—CN, —$CO_2R^{11}$, —$NO_2$, —$CON(R^{11})_2$, —$CSN(R^{11})_2$, —$COR^{11}$, —$CSN(R^{11})_2$, —$N(R^{11})COR^{11}$, —$N(R^{11})CSR^{11}$, —$SO_2N(R^{11})_2$, —$N(R^{11})SO_2R^{11}$, —$N(R^{11})CON(R^{11})_2$, —$N(R^{11})CSN(R^{11})_2$, $N(R^{11})SO_2N(R^{11})_2$ or optionally substituted phenyl group. Where two $R^{11}$ atoms or groups are present in these substituents these may be the same or different. Optionally substituted phenyl groups include phenyl substituted by one, two or three of the $R^{13}$ groups described below.

Additionally, when the group $R^3$ is a heterocycloaliphatic group containing one or more nitrogen atoms each nitrogen atom may be optionally substituted by a group —$(L^6)_p$(Alk$^5$)$_q$R$^{12}$ in which $L^6$ is —C(O)—, —C(O)O—, —C(S)—, —S(O)2—, —CON(R$^{11}$)—, —CSN(R$^{11}$)— or SO$_2$N(R$^{11}$)—; p is zero or an integer 1; Alk$^5$ is an optionally substituted aliphatic or heteroaliphatic chain; q is zero or an integer 1; and $R^{12}$ is a hydrogen atom or an optionally substituted cycloaliphatic, heterocycloaliphatic, polycycloaliphatic, polyheterocycloaliphatic, aromatic or heteroaromatic group.

Optionally substituted aliphatic or heteroaliphatic chains represented by Alk$^5$ include those optionally substituted chains described above for Alk$^1$ and $R^3$ respectively.

Cycloaliphatic, heterocycloaliphatic, polycycloaliphatic or polyheterocycloaliphatic groups represented by $R^{12}$ include those groups just described for the group $R^3$. Optional substituents which may be present on these groups include those described above in relation to Alk$^1$ and $R^3$ aliphatic and heteroaliphatic chains.

When the group $R^3$ is an optionally substituted aromatic or heteroaromatic group it may be for example an aromatic or heteroaromatic group as described herein for the group $Ar^1$.

Optional substituents which may be present on the aromatic or heteroaromatic groups represented by the group $R^3$ include one, two, three or more substituents, each selected from an atom or group $R^{13}$ in which $R^{13}$ is $R^{13a}$ or -Alk$^6$(R$^{13a}$)$_m$, where $R^{13a}$ is a halogen atom, or an amino (—$NH_2$), substituted amino, nitro, cyano, amidino, hydroxyl (—OH), substituted hydroxyl, formyl, carboxyl (—$CO_2H$), esterified carboxyl, thiol (—SH), substituted thiol, —$COR^{14}$ [where $R^{14}$ is an -Alk$^6$(R$^{13a}$)$_m$, cycloaliphatic, heterocycloaliphatic, aryl or heteroaryl group], —$CSR^{14}$, —$SO_3H$, —$SOR^{14}$, —$SO_2R^{14}$, —$SO_3R^{14}$, —$SO_2NH_2$, —$SO_2NHR^{14}$ $SO_2N(R^{14})_2$, —$CONH_2$, —$CSNH_2$, —$CONHR^{14}$, —$CSNHR^{14}$, —$CON[R^{14}]_2$, —$CSN(R^{14})_2$, —$N(R^{11})SO_2R^{14}$, —$N(SO_2R^{14})_2$, —$NH(R^{11})SO_2NH_2$, —$N(R^{11})SO_2NHR^{14}$, —$N(R^{11})SO_2N(R^{14})_2$, —$N(R^{11})COR^{14}$, —$N(R^{11})CONH_2$, —$N(R^{11})CONHR^{14}$, —$N(R^{11})CON(R^{14})_2$, —$N(R^{11})CSNH_2$, —$N(R^{11})CSNHR^{14}$, —$N(R^{11})CSN(R^{14})_2$, —$N(R^{11})CSR^{14}$, —$N(R^{11})C(O)OR^{14}$, —$SO_2NHet^1$ (where —$NHet^1$ is an optionally substituted $C_{5-7}$cyclicamino group optionally containing one or more other —O— or —S— atoms or —$N(R^{11})$—, —C(O)—, —C(S)—, S(O) or —$S(O)_2$ groups], —$CONHet^1$, —$CSNHet^1$, —$N(R^{11})SO_2NHet^1$, —$N(R^{11})CONHet^1$, —N($R^{11}$)CSNHet$^1$, —SO$_2$N($R^{11}$)Het$^2$ [where Het$^2$ is an optionally substituted monocyclic C$_{5-7}$carbocyclic group optionally containing one or more —O— or —S— atoms or —N($R^{11}$)—, —C(O)— or —C(S)— groups], —Het$^2$, —CON($R^{11}$)Het$^2$, —CSN($R^{11}$)Het$^2$, —N($R^{11}$)CON($R^{11}$)Het$^2$, —N($R^{11}$)CSN($R^{11}$)Het$^2$, cycloaliphatic, heterocycloaliphatic, aryl or heteroaryl group; Alk$^6$ is a straight or branched C$_{1-6}$alkylene, C$_{2-6}$alkenylene or C$_{2-6}$alkynylene chain, optionally interrupted by one, two or three —O— or —S— atoms or —S(O)$_n$ [where n is an integer 1 or 2] or —N($R^{15}$)— groups [where $R^{15}$ is a hydrogen atom or C$_{1-6}$alkyl, e.g. methyl or ethyl group]; and m is zero or an integer 1, 2 or 3. It will be appreciated that when two $R^{11}$ or $R^{14}$ groups are present in one of the above substituents, the $R^{11}$ or $R^{14}$ groups may be the same or different.

When in the group -Alk$^6$($R^{13a}$)$_m$ m is an integer 1, 2 or 3, it is to be understood that the substituent or substituents $R^{13a}$ may be present on any suitable carbon atom in -Alk$^6$. Where more than one $R^{13a}$ substituent is present these may be the same or different and may be present on the same or different atom in -Alk$^6$. Clearly, when m is zero and no substituent $R^{13a}$ is present the alkylene, alkenylene or alkynylene chain represented by Alk$^6$ becomes an alkyl, alkenyl or alkynyl group.

When $R^{13a}$ is a substituted amino group it may be for example a group —NHR$^{14}$ [where $R^{14}$ is as defined above] or a group —N($R^{14}$)$_2$ wherein each $R^{14}$ group is the same or different.

When $R^{13a}$ is a halogen atom it may be for example a fluorine, chlorine, bromine, or iodine atom.

When $R^{13a}$ is a substituted hydroxyl or substituted thiol group it may be for example a group —OR$^{14}$ or a —SR$^{14}$ or —SC(=NH)NH$_2$ group respectively.

Esterified carboxyl groups represented by the group $R^{13a}$ include groups of formula —CO$_2$Alk$^7$ wherein Alk$^7$ is a straight or branched, optionally substituted C$_{1-8}$alkyl group such as a methyl, ethyl, n-propyl, i-propyl, n-butyl, i-butyl, s-butyl or t-butyl group; a C$_{1-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$aryloxyC$_{1-8}$alkyl group such as an optionally substituted phenyloxymethyl, phenyloxyethyl, 1-naphthyloxymethyl, or 2-naphthyloxymethyl group; an optionally substituted C$_{1-8}$alkanoyloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the Alk$^7$ group include $R^{13a}$ substituents described above.

When Alk$^6$ is present in or as a substituent it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N($R^9$)— groups.

Cycloaliphatic or heterocycloaliphatic groups represented by the groups $R^{13a}$ or $R^{14}$ include those optionally substituted C$_{3-10}$cycloaliphatic or C$_{3-10}$heterocycloaliphatic groups described above for $R^3$.

Aryl or heteroaryl groups represented by the groups $R^{13a}$ or $R^{14}$ include mono- or bicyclic optionally substituted C$_{6-12}$ aromatic or C$_{1-9}$ heteroaromatic groups as described above for the group Ar$^1$. The aromatic and heteroaromatic groups may be attached to the remainder of the compound of formula (1) by any carbon or hetero e.g. nitrogen atom as appropriate.

When —NHet$^1$ or —Het$^2$ forms part of a substituent $R^{13}$ each may be for example an optionally substituted pyrrolidinyl, pyrazolidinyl, piperazinyl, morpholinyl, thiomorpholinyl, piperidinyl or thiazolidinyl group. Additionally Het$^2$ may represent for example, an optionally substituted cyclopentyl or cyclohexyl group. Optional substituents which may be present on —NHet$^1$ or —Het$^2$ include those $R^7$ substituents described above.

Particularly useful atoms or groups represented by $R^{13}$ include fluorine, chlorine, bromine or iodine atoms, or C$_{1-6}$alkyl, e.g. methyl, ethyl, n-propyl, i-propyl, n-butyl or t-butyl, optionally substituted phenyl, pyridyl, pyrimidinyl, pyrrolyl, furyl, thiazolyl, thienyl, morpholinyl, thiomorpholinyl, piperazinyl, e.g. t-butyloxycarbonylpiperazinyl, pyrrolidinyl, dioxolanyl, dioxanyl, oxazolidinyl, thiazolidinyl, imidazolidinyl or piperidinyl, C$_{1-6}$hydroxyalkyl, e.g. hydroxymethyl or hydroxyethyl, carboxyC$_{1-6}$alkyl, e.g. carboxyethyl, C$_{1-6}$alkylthio e.g. methylthio or ethylthio, carboxyC$_{1-6}$alkylthio, e.g. carboxymethylthio, 2-carboxyethylthio or 3-carboxypropylthio, C$_{1-6}$alkoxy, e.g. methoxy or ethoxy, hydroxyC$_{1-6}$alkoxy, e.g. 2-hydroxyethoxy, optionally substituted phenoxy, pyridyloxy, thiazolyoxy, phenylthio or pyridylthio, C$_{4-7}$cycloalkyl, e.g. cyclobutyl, cyclopentyl, C$_{5-7}$cycloalkoxy, e.g. cyclopentyloxy, haloC$_{1-6}$alkyl, e.g. trifluoromethyl, haloC$_{1-6}$alkoxy, e.g. trifluoromethoxy, C$_{1-6}$alkylamino, e.g. methylamino, ethylamino or propylamino, C$_{6-12}$arylC$_{1-6}$alkylamino, e.g. benzylamino, 4-fluorobenzylamino or 4-hydroxyphenylethylamino, amino (—NH$_2$), aminoC$_{1-6}$alkyl, e.g. aminomethyl or aminoethyl, C$_{1-6}$dialkylamino, e.g. dimethylamino or diethylamino, aminoC$_{1-6}$alkylamino, e.g. aminoethylamino or aminopropylamino, optionally substituted Het$^1$NC$_{1-6}$alkylamino, e.g. 3-morpholinopropylamino, C$_{1-6}$alkylaminoC$_{1-6}$alkyl, e.g. ethylaminoethyl, C$_{1-6}$dialkylaminoC$_{1-6}$alkyl, e.g. diethylaminoethyl, aminoC$_{1-6}$alkoxy, e.g. aminoethoxy, C$_{1-6}$alkylamino C$_{1-6}$alkoxy, e.g. methylaminoethoxy, C$_{1-6}$dialkylamino C$_{1-6}$alkoxy, e.g. dimethylaminoethoxy, diethylaminoethoxy, diisopropylaminoethoxy, or dimethylaminopropoxy, hydroxyC$_{1-6}$alkylamino, e.g. 2-hydroxyethylamino, 3-hydroxypropylamino or 3-hydroxybutylamino, imido, such as phthalimido or naphthalimido, e.g. 1,8-naphthalimido, nitro, cyano, amidino, hydroxyl (—OH), formyl [HC(O)—], carboxyl (—CO$_2$H), —CO$_2$Alk$^7$ [where Alk$^7$ is as defined above], C$_{1-6}$ alkanoyl e.g. acetyl, propyryl or butyryl, optionally substituted benzoyl, thiol (—SH), thioC$_{1-6}$alkyl, e.g. thiomethyl or thioethyl, —SC(=NH) NH$_2$, sulphonyl (—SO$_3$H), —SO$_3$Alk$^7$, C$_{1-6}$alkylsulphinyl, e.g. methylsulphinyl, ethylsulphinyl or propylsulphinyl, C$_{1-6}$alkylsulphonyl, e.g. methylsulphonyl, ethylsulphonyl or propylsulphonyl, aminosulphonyl (—SO$_2$NH$_2$), C$_{1-6}$alkylaminosulphonyl, e.g. methylaminosulphonyl, ethylaminosulphonyl or propylaminosulphonyl C$_{1-6}$dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl, ethylaminocarbonyl or propylaminocarbonyl, C$_{1-6}$dialkylaminocarbonyl, e.g. dimethylaminocarbonyl or diethylaminocarbonyl, amino C$_{1-6}$alkylaminocarbonyl, e.g. aminoethylaminocarbonyl, C$_{1-6}$alkylaminoC$_{1-6}$alkylaminocarbonyl, e.g. methylaminoethylaminocarbonyl, C$_{1-6}$dialkylamino C$_{1-6}$alkylaminocarbonyl, e.g. diethylaminoethylaminocarbonyl, aminocarbonylamino, C$_{1-6}$alkylaminocarbonylamino, e.g. methylaminocarbonylamino or ethylaminocarbonylamino, $C_{1-6}$dialkylaminocarbonylamino, e.g. dimethylaminocarbonylamino or diethylaminocarbonylamino, $C_{1-6}$alkylaminocabonyl$C_{1-6}$alkylamino, e.g. methylaminocarbonylmethylamino, aminothiocarbonylamino, $C_{1-6}$alkylaminothiocarbonylamino, e.g. methylaminothiocarbonylamino or ethylaminothiocarbonylamino, $C_{1-6}$dialkylaminothiocarbonylamino, e.g. dimethylaminothiocarbonylamino or diethylaminothiocarbonylamino, $C_{1-6}$alkylaminothiocarbonyl $C_{1-6}$alkylamino, e.g. ethylaminothiocarbonylmethylamino, —CONHC(=NH)NH$_2$, $C_{1-6}$alkylsulphonylamino, e.g. methylsulphonylamino or ethylsulphonylamino, halo$C_{1-6}$alkylsulphonylamino, e.g. trifluoromethylsulphonylamino, $C_{1-6}$dialkylsulphonylamino, e.g. dimethylsulphonylamino or diethylsulphonylamino, optionally substituted phenylsulphonylamino, aminosulphonylamino (—NHSO$_2$NH$_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, optionally substituted morpholinesulphonylamino or morpholinesulphonyl$C_{1-6}$alkylamino, optionally substituted phenylaminosulphonylamino, $C_{1-6}$alkanoylamino, e.g. acetylamino, amino$_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino $C_{1-6}$alkyl, e.g. acetylaminomethyl, $C_{1-6}$alkanoylamino $C_{1-6}$alkylamino, e.g. acetamidoethylamino, $C_{1-6}$alkoxycarbonylamino, e.g. methoxycarbonylamino, ethoxycarbonylamino or t-butoxycarbonylamino or optionally substituted benzyloxy, pyridylmethoxy, thiazolylmethoxy, benzyloxycarbonylamino, benzyloxycarbonylamino$C_{1-6}$alkyl e.g. benzyloxycarbonylaminoethyl, thiobenzyl, pyridylmethylthio or thiazolylmethylthio groups.

Where desired, two $R^{13}$ substituents may be linked together to form a cyclic group such as a cyclic ether, e.g. a $C_{1-6}$alkylenedioxy group such as methylenedioxy or ethylenedioxy.

It will be appreciated that where two or more $R^{13}$ substituents are present, these need not necessarily be the same atoms and/or groups. In general, the substituent(s) may be present at any available ring position in the aromatic or heteroaromatic group represented by $R^3$.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isothionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In the compounds according to the invention the group $R^1$ is preferably an Ar$^1$L$^2$Ar$^2$Alk- group. In compounds of this type Ar$^1$ is preferably an optionally substituted phenyl, monocyclic heteroaromatic or bicyclic heteroaromatic group. Particularly useful monocyclic heteroaromatic groups are optionally substituted five- or six-membered heteroaromatic groups as described previously, especially five- or six-membered heteroaromatic groups containing one or two heteroatoms selected from oxygen, sulphur or nitrogen atoms. Nitrogen-containing groups are especially useful, particularly pyridyl or pyrimidinyl groups. Particularly useful substituents present on these Ar$^1$ groups include halogen atoms or optionally substituted alkyl, —OR$^5$, —SR$^5$, —NR$^5$R$^6$, —CO$_2$H, —CO$_2$CH$_3$, —NO$_2$ or —CN groups as described above in relation to the compounds of formula (1). Particularly useful bicyclic heteroaromatic groups represented by Ar$^1$ include optionally substituted ten-membered fused-ring heteroaromatic groups containing one or two heteroatoms, especially nitrogen atoms. Particular examples include optionally substituted naphthyridinyl, especially 2,6-naphthyridinyl, quinolinyl and isoquinolinyl, especially isoquinolin-1-yl groups. Particular optional substituents include those just described for monocyclic heteroaromatic groups.

A particularly useful group of compounds according to the invention has the formula (2a):

wherein —W= is —CH= or —N=;

$R^{16}$ and $R^{17}$, which may be the same or different is each a hydrogen atom or an atom or group —L$^3$(Alk$^2$)$_t$L$^4$ (R$^4$)$_u$ in which L$^3$, Alk$^2$, t, L$^4$ R$^4$ and u are as defined previously;

L$^1$, L$^2$, Ar$^2$, Alk, R$^2$, Alk$^1$, n and R$^3$ are as defined for formula (1);

and the salts, solvates, hydrates and N-oxides thereof.

—W= in compounds of formula (2a) is preferably —N=.

$R^{16}$ and $R^{17}$ in compounds of formula (2a) is each preferably as particularly described above for compounds of formula (1), other than a hydrogen atom. Particularly useful $R^{16}$ and $R^{17}$ substituents include halogen atoms, especially fluorine or chlorine atoms, or methyl, halomethyl, especially —CF$_3$, —CHF$_2$ or —CH$_2$F, methoxy or halomethoxy, especially —OCF$_3$, —OCHF$_2$ or —OCH$_2$F groups.

A further particularly useful group of compounds according to the invention has the formula (2b):

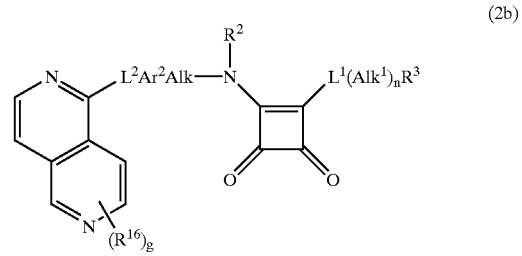

(2b)

wherein $R^{16}$, L$^1$, L$^2$, Ar$^2$, Alk, R$^2$, Alk$^1$, n and R$^3$ are as defined for formula (2a);

g is zero or the integer 1, 2, 3 or 4;

and the salts, solvates, hydrates and N-oxides thereof.

Each $R^{16}$ atom or group in compounds of formula (2b) may be independently selected from an atom or group —L$^3$(Alk$^2$)$_t$L$^3$(R$^4$)$_u$ in which L$^3$, Alk$^2$, t, L$^4$, R$^4$ and u are as previously defined. Particularly useful $R^{16}$ substituents when present in compounds of formula (2b) include halogen atoms, especially fluorine, chlorine or bromine atoms, or methyl, halomethyl, especially —$CF_3$, methoxy or halomethoxy, especially —$OCF_3$, —CN, —$CO_2$Me, —$NO_2$, amino (—$NH_2$), substituted amino (—$NR^5R^6$) and —$N(R^5)COCH_3$, especially —$NHCOCH_3$ groups.

In one preferred group of compounds of formula (2b) each $R^{16}$ is a hydrogen atom.

Another particularly useful group of compounds according to the invention has the formula (2c):

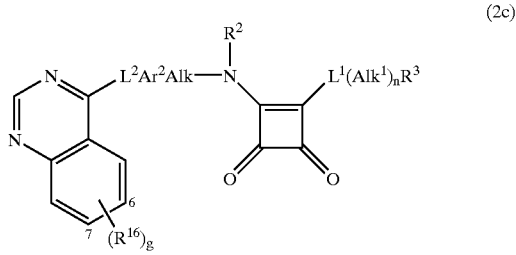

(2c)

wherein $R^{16}$, g, $L^1$, $L^2$, $Ar^2$, Alk, $R^2$, $Alk^1$, n and $R^3$ are as defined for formula (2b);

and the carbon atoms at positions 6 and 7 of the naphthyridine ring are indicated with the appropriate numerals, and the salts, solvates, hydrates and N-oxides thereof.

Each $R^{16}$ atom or group in compounds of formula (2c) may be independently selected for an atom or group —$L^3$ $(Alk^2)_tL^4(R^4)_u$ in which $L^3$, $Alk^2$, t, $L^4$, $R^4$ and u areas previously defined. Particularly useful $R^{16}$ substituents when present in compounds of formula (2c) include halogen atoms, especially fluorine or chlorine atoms, methyl, halomethyl, especially —$CF_3$, methoxy or halomethoxy, especially —$OCF_3$, —CN, —$CO_2$Me, —$NO_2$, amino (—$NH_2$), substituted amino (—$NR^5R^6$) and —$N(R^5)$ $COCH_3$, especially —$NHCOCH_3$ groups.

In one preferred group of compounds of formula (2c) g is the integer 1 and $R^{16}$ is a methoxy group, especially a methoxy group present at the 6-position. In another preferred group of formula (2c) g is the integer 2 and each $R^{16}$ group is a methoxy group, especially a methoxy group present at the 6- and 7-positions.

Alk in compounds of the invention is preferably:

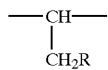

or, especially, —$CH_2CH(R)$—.

R in the compounds of formulae (1), (2a), (2b) and (2c) is preferably a —$CO_2H$ group.

In general in compounds of formulae (1), (2a), (2b) and (2c) $R^2$ is preferably a hydrogen atom.

In general in compounds of formula (2a) $L^2$ is preferably $L^{2a}$ where $L^{2a}$ is a —$CON(R^8)$— group, especially —CONH—.

In general in compounds of formulae (2b) and (2c) $L^2$ is preferably $L^{2a}$ where $L^{2a}$ is an —O— atom or —$N(R^8)$— group. An especially useful —$N(R^8)$— group is —NH—.

The group $Ar^2$ in compounds of formulae (1), (2a), (2b) and (2c) is preferably an optionally substituted phenylene group. Particularly useful groups include optionally substituted 1,4-phenylene groups.

In general in compounds of formulae (1), (2a), (2b) and (2c) when n is zero or the integer 1 the group $R^3$ may especially be a hydrogen atom or an optionally substituted heteroaliphatic, cycloaliphatic, heterocycloaliphatic, aromatic or heteroaromatic group as defined herein. Particularly useful groups of this type include optionally substituted $C_{2-6}$heteroalkyl, particularly $C_{1-3}$alkoxy$C_{1-3}$alkyl, especially methoxypropyl, optionally substituted $C_{3-7}$cycloalkyl, especially optionally substituted cyclopropyl, cyclobutyl, cyclopentyl, cyclopropyl or cyclohexyl, optionally substituted $C_{5-7}$heterocycloaliphatic, especially optionally substituted pyrrolidinyl, piperidinyl or thiazolidinyl, especially optionally substituted phenyl and optionally substituted $C_{5-7}$heteroaromatic, especially optionally substituted pyridyl, pyrimidinyl or triazinyl groups. Optional substituents on these groups include in particular $R^{13}$ atoms or groups where the group is an aromatic or heteroaromatic group and halogen atoms or $C_{1-6}$alkyl, especially methyl, halo$C_{1-6}$alkyl, especially trifluoromethyl, $C_{1-6}$alkoxy, especially methoxy, halo$C_{1-6}$alkoxy, especially trifluoromethoxy or —$(L^6)_p(Alk^5)_qR^{12}$ groups as described earlier where the group is a nitrogen-containing heterocycloaliphatic group such as a pyrrolidinyl, piperidinyl or thiazolidinyl group. Particularly useful —$(L^6)_p(Alk^5)_qR^{12}$ groups include those in which $L^6$ is a —CO— group. $Alk^5$ in these groups is preferably present (i.e. q is preferably an integer 1) and in particular is a —$CH_2$— chain.

Compounds of this type in which $R^{12}$ is a hydrogen atom or an optionally substituted aromatic or heteroaromatic group, especially an optionally substituted phenyl, pyridyl or imidazolyl group are particularly preferred.

In one preferred class of compounds of formulae (1), (2a), (2b) and (2c) $L^1$ is present as a —$N(R^8)$— group. Particularly useful —$N(R^8)$— groups include —NH—, —$N(CH_3)$—, —$N(CH_2CH_3)$— and —$N(CH_2CH_2CH_3)$— groups. In this class of compounds n is preferably the integer 1 and $Alk^1$ is preferably an optionally substituted straight or branched $C_{1-6}$alkylene chain. Particularly useful $Alk^1$ chains include —$CH_2$—, —$CH_2CH_2$—, —$CH_2CH_2CH_2$—, —CH $(CH_3)CH_2$— and —$C(CH_3)_2CH_2$—. $R^3$ in this class of compounds is preferably a hydrogen atom.

In another preferred class of compounds of formulae (1), (2a), (2b) and (2c) $L^1$ is a covalent bond, n is the integer 1 and $Alk^1$ is an optionally substituted straight or branched $C_{1-6}$alkylene chain. Particularly useful $Alk^1$ chains include optionally substituted —$CH_2$—, —$CH_2CH_2$—, —$CH_2CH_2CH_2$— and —$CH(CH_3)CH_2$— and especially —$C(CH_3)_2CH_2$— chains. $R^3$ in this class of compounds is preferably a hydrogen atom. A most especially useful optionally substituted $Alk^1R^3$ group is —$C(CH_3)_3$.

In another preferred class of compounds of formulae (1), (2a), (2b) and (2c), $L^1$ is a covalent bond, n is zero and $R^3$ is an optionally substituted $C_{5-7}$heterocycloaliphatic, especially an optionally substituted piperidinyl group. A most especially useful optionally substituted piperidinyl group is an optionally substituted piperidin-1-yl group.

Particularly useful compounds of the invention include:
(S)-3-[4-(3,5-Dichloro-4-pyridylcarboxamido)phenyl]-2-(2-propylamino-3,4-dioxocyclobut-1-enyl)amino] propanoic acid;
(S)-3-[4-(3,5-Dichloro-4-pyridylcarboxamido)phenyl]-2-(2-t-butyl-3,4-dioxocyclobut-1-enyl)amino]propanoic acid;
(S)-3-{4-[(6,7-Dimethoxy-4-quinazolinyl)amino]phenyl}-2-[(2-N,N-diethylamino-3,4-dioxocyclobut-1-enyl) amino]propanoic acid;
(S)-3-[4-([2,6-Naphthyridin-1-yl]amino)phenyl]-2-[(2-N,N-diethylamino-3,4-dioxocyclobut-1-enyl)amino]propanoic acid;

(S)-3-[4-([6,7-Dimethoxy-4-quinazolinyl)oxy]phenyl]-2-[(2-N,N-diethylamino-3,4-dioxocyclobut-1-enyl)amino]propanoic acid;

(S)-3-[4-([6,7-Methoxy-4-quinazolinyl]amino)phenyl]-2-[(2-N,N-diethylamino-3,4-dioxocyclobut-1-enyl)amino]propanoic acid;

(S)-3-[4-([2,6-Naphthyridin-1-yl]amino)phenyl]-2-[(2-N,N-dipropylamino-3,4-dioxocyclobut-1-enyl)amino]propanoic acid;

(S)-3-[4-([2,6-Naphthyridin-1-yl]oxy)phenyl]-2-[(2-N,N-diethylamino-3,4-dioxocyclobut-1-enyl)amino]propanoic acid;

(S)-3-[4-([2,6-Naphthyridin-1-yl]amino)phenyl]-2-[(2-piperidin-1-yl-3,4-dioxocyclobut-1-enyl)amino]propanoic acid;

(R)-3-{4-(3,5-Dichloro-4-pyridylcarboxamido)phenyl}-3-[(2-N,N-diethylamino-3,4-dioxocyclobut-1-enyl)amino]propanoic acid;

(S)-3-[4-([2,6-Naphthyridin-1-yl]oxy)phenyl]-2-[(2-N,N-dipropylamino-3,4-dioxocyclobut-1-enyl)amino]propanoic acid;

(S)-3-[4-([2,6-Naphthyridin-1-yl]amino)phenyl]-2-[(2-N-ethyl-N-isopropylamino-3,4-dioxocyclobut-1-enyl)amino]propanoic acid;

and the salts, solvates, hydrates and N-oxides thereof.

The compounds according to the invention are generally of use in modulating cell adhesion. Thus for example when $R^1$ in compounds of the invention is an $a_4$-integrin binding groups the compounds are of use in the prophylaxis and treatment of diseases or disorders involving inflammation in which the extravasation of leukocytes plays a role.

Diseases or disorders of this type include inflammatory arthritis such as rheumatoid arthritis vasculitis or polydermatomyositis, multiple sclerosis, allograft rejection, diabetes, inflammatory dermatoses such as psoriasis or dermatitis, asthma and inflammatory bowel disease.

In another example when $R^1$ is an $\alpha_V$-integrin binding group the compounds may be of use in the prophylaxis and treatment of diseases or disorders involving inappropriate growth or migration of cells. Particular diseases include inflammatory diseases, and diseases involving angiogenesis, bone resorption or cllular or matrix over-expression.

Particular uses to which these compounds of the invention may be put include the treatment or inhibition of tumour growth and metastasis; retinopathy; macular degeration psoriasis; rheumatoid arthritis, osteoporosis; bone resorption following or due to joint replacement, hypercalcemia or malignancy, Paget's disease, glucocorticoid treatment, immonilisation-induced osteopenia, hyperparathyroidism or peridontal disease, vascuar restenosis, atherosclerosis; inflammatory bowel disease; and psoriasis.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use. For particle mediated administration the compounds of formula (1) may be coated on particles such as microscopic gold particles.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols $Ar^1$, $Ar^2$, Alk, $R^1$, $R^2$, $R^3$, $L^1$, $L^2$, $Alk^1$ and n when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups. For convenience the processes described below all refer to a preparation of a compound of formula (1) but clearly the description applies equally to the preparation of compounds of formula (2).

Thus according to a further aspect of the invention, a compound of formula (1) in which R is a —$CO_2H$ group may be obtained by hydrolysis of an ester of formula (3):

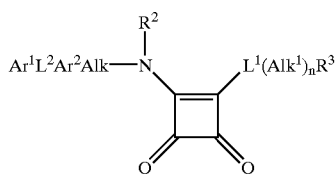

(3)

where Alk represents a group

—$CH_2CH(CO_2R^y)$—,    —$CH=CH(CO_2R^y)$—,

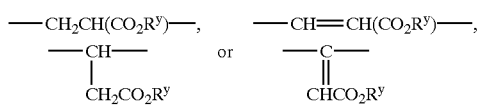

[where $R^y$ is an alkyl group for example a $C_{1-6}$alkyl group]

The hydrolysis may be performed using either an acid or a base depending on the nature of $R^y$, for example an organic acid such as trifluoroacetic acid or an inorganic base such as lithium, sodium or potassium hydroxide optionally in an aqueous organic solvent such as an amide e.g. a substituted amide such as dimethylformamide, an ether e.g. a cyclic ether such as tetrahydrofuran or dioxane or an alcohol e.g. methanol at a temperature from ambient to the reflux temperature. Where desired, mixtures of such solvents may be used.

According to a further aspect of the invention a compound of formula (1) may be prepared by displacement of a leaving group from a compound of formula (4):

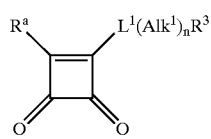

(4)

where $R^a$ is a leaving group, with an amine $R^1R^2NH$ or a salt thereof. Suitable leaving groups represented by $R^a$ include halogen atoms, especially chlorine and bromine atoms, or alkoxy, e.g. methoxy, ethoxy or isopropoxy, aryloxy, e.g. dinitrophenyloxy, or aralkoxy, e.g. benzyloxy, groups.

The reaction may be performed in an inert solvent or mixture of solvents, for example a substituted amide such as dimethylformamide, an alcohol such as ethanol and/or a halogenated hydrocarbon such as dichloromethane, at a temperature from 0° C. to the reflux temperature. Where necessary, for example when a salt of an amine $R^1R^2NH$ is used, an organic base such as diisopropylethylamine can be added.

Any carboxylic acid group present in the intermediate of formula (4) or the amine $R^1R^2NH$ may need to be protected during the displacement reaction, for example as an ethyl ester. The desired acid may then be obtained through subsequent hydrolysis, for example as particularly described above and generally described below.

It will be appreciated that the displacement reaction may also be performed on a compound of formula (5):

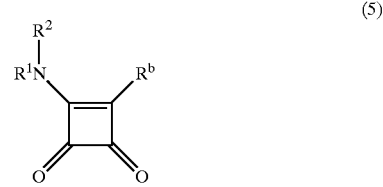

(5)

where $R^b$ is a leaving group as defined for $R^a$ using an intermediate $R^3(Alk^1)_nL^1H$ where —$L^1H$ is a functional group such as an amine (—$NH_2$) using the reaction conditions just described.

Where desired the displacement reaction may also be performed on an intermediate of formulae (4) or (5), $R^1R^2NH$ or $R^3(Alk^1)_nL^1H$ which is linked, for example via its $R^1$ or $R^3$ group, to a solid support, such as a polystyrene resin. After the reaction the desired compound of formula (1) may be displaced from the support by any convenient method, depending on the original linkage chosen.

Intermediates of formulae (4) and (5) are either readily available or may be prepared from an intermediate of formula (6):

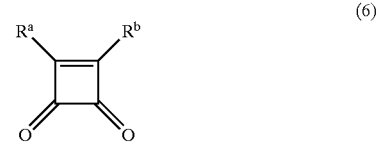

(6)

where $R^a$ and $R^b$ are as previously defined and an amine $R^1R^2NH$ or intermediate $(R^3(Alk^1)_nL^1H$ by displacement as just described for the preparation of compounds of formula (1).

Intermediates of formulae $R^1R^2NH$ and $R^3(Alk^1)_nL^1H$ may be obtained from simpler, known compounds by one or more standard synthetic methods employing substitution, oxidation, reduction or cleavage reactions. Particular substitution approaches include conventional alkylation, arylation, heteroarylation, acylation, thioacylation, halogenation, sulphonylation, nitration, formylation and coupling procedures. It will be appreciated that these methods may also be used to obtain or modify other compounds of formulae (1) and (2) where appropriate functional groups exist in these compounds.

Thus compounds of the invention and intermediates thereto may be prepared by alkylation, arylation or heteroarylation. For example, compounds containing a —$L^1H$ or —$L^2H$ group (where $L^1$ and $L^2$ is each a linker atom or group) may be treated with a coupling agent $R^3(Alk^1)_nX^1$ or $Ar^1X^1$ respectively in which $X^1$ is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluene-sulphonyloxy group.

The reaction may be carried out in the presence of a base such as a carbonate, e.g. caesium or potassium carbonate, an alkoxide, e.g. potassium t-butoxide, or a hydride, e.g.

sodium hydride, or an organic amine e.g. triethylamine or N,N-diisopropylethylamine or a cyclic amine, such as N-methylmorpholine or pyridine, in a dipolar aprotic solvent such as an amide, e.g. a substituted amide such as dimethylformamide or an ether, e.g. a cyclic ether such as tetrahydrofuran.

Intermediates of formula $Ar^1X^1$ and $R^3(Alk^1)_nX^1$ are generally known, readily available compounds or may be prepared from known compounds by standard substitution and other synthetic procedures, for example as described herein. Thus for example compounds of formula $Ar^1X^1$ in which, for example, $Ar^1$ represents a 2,6-naphthyridine group may be prepared from alcohols of formula $Ar^1OH$ by reaction with a halogenating agent, for example a phosphorous oxyhalide such as phosphorous oxychloride at an elevated temperature e.g. 110° C.

Intermediate alcohols of formula $Ar^1OH$ in which, for example, $Ar^1$ represents a 2,6-naphthyridine group may be prepared by methods well known to a person skilled in the art, e.g. by the method of Sakamoto,T. et al [Chem. Pharm. Bull. 33, 626–633, (1985)].

Alternatively alkylating agents of formula $Ar^1X^1$ in which, for example, $Ar^1$ represents a 2,6-naphthyridine group may be prepared by reaction of a 2,6-naphthyridine N-oxide or N,N'-dioxide with a halogenating agent, e.g. a phosphorous oxyhalide such as phosphorous oxychloride to give a 1-halo or 1,5-dihalo-2,6-napthyridine respectively. In the case of 1,5-dihalo-2,6-napthyridines each halogen atom may be substituted separately by a reagent such as $HL^2Ar^2AlkN(R^2)H$ or $HL^3(Alk^2)_rL^4(R^4)_u$ by the particular methods just described above.

2,6-Napthyridine N-oxides and N,N'-dioxides may be generated from the corresponding 2,6-napthyridines group by the general methods of synthesis of N-oxides described below or they may be synthesised by the methods of Numata, A. et al (Synthesis, 1999, 306–311).

Further alkylating agents of formula $Ar^1X^1$ in which, for example, $Ar^1$ represents a 2,6-naphthyridine, may be prepared by the methods of Giacomello G. et al (Tetrahedron Letters 1965, 1117–1121), Tan, R. and Taurins, A. (Tetrahedron Letters 1965, 2737–2744), Ames, D. E. and Dodds, W. D. (J. Chem. Soc. Perkin 1 1972, 705–710) and Alhaique, F. et al (Tetdrahedron Letters, 1975, 173–174).

In a further example intermediates of formula $R^1R^2NH$ may be obtained by reaction of a compound of formula $Ar^1L^2H$ with a compound of formula $X^1Ar^2AlkN(R^2)H$ under the reaction conditions just described Compounds of formula $Ar^1L^2H$ in which, for example $Ar^1$ represents a 2,6-naphthyridine and $L^2$ is a —$N(R^8)$— group, may be prepared from substituted 4-cyano-3-cyanomethylpyridines by the methods of Alhaique, F. et al (ibid and Gazz. Chim. Ital. 1975, 105, 1001–1009) or from 3-fomylpyridines by the methods of Molina, P. at al (Tetrahedron 1992, 48, 4601–4616).

In another example, compounds containing a —$L^1$H or —$L^2$H or group as defined above may be functionalised by acylation or thioacylation, for example by reaction with one of the alkylating agents just described but in which $X^1$ is replaced by a —C(O)$X^2$, C(S)$X^2$, —$N(R^8)COX^2$ or —$N(R^8)C(S)X^2$ group in which $X^2$ is a leaving atom or group as described for $X^1$. The reaction may be performed in the presence of a base, such as a hydride, e.g. sodium hydride or an amine, e.g. triethylamine or N-methylmorpholine, in a solvent such as a halogenated hydrocarbon, e.g. dichloromethane or carbon tetrachloride or an amide, e.g. dimethylformamide, at for example ambient temperature. Alternatively, the acylation may be carried out under the same conditions with an acid (for example one of the alkylating agents described above in which $X^1$ is replaced by a —$CO_2H$ group) in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively the acid may be reacted with a chloroformate, for example ethylchloroformate, prior to the desired acylation reaction.

In a further example compounds may be obtained by sulphonylation of a compound containing an —OH group by reaction with one of the above alkylating agents but in which $X^1$ is replaced by a —S(O)Hal or —$SO_2$Hal group in which Hal is a halogen atom such as chlorine atom] in the presence of a base, for example an inorganic base such as sodium hydride in a solvent such as an amide, e.g. a substituted amide such as dimethylformamide at for example ambient temperature.

In another example, compounds containing a —$L^1$H or —$L^2$H group as defined above may be coupled with one of the alkylation agents just described but in which $X^1$ is replaced by an —OH group in a solvent such as tetrahydrofuran in the presence of a phosphine, e.g. triphenylphosphine and an activator such as diethyl, diisopropyl- or dimethylazodicarboxylate.

In a further example, ester groups —$CO_2R^5$, —$CO_2Alk^3$ or —$CO_2Alk^7$ in the compounds may be converted to the corresponding acid [—$CO_2H$] by acid- or base-catalysed hydrolysis depending on the nature of the groups $R^5$, $Alk^3$ or $Alk^7$. Acid- or base-catalysed hydrolysis may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a further example, —$OR^5$ or —$OR^{14}$ groups [where $R^5$ or $R^{14}$ each represents an alkyl group such as methyl group] in compounds of formula (1) may be cleaved to the corresponding alcohol —OH by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding —$OCH_2R^{14}$ group (where $R^{14}$ is an aryl group) using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester [$CO_2Alk^5$ or $CO_2R^5$] or aldehyde [—CHO] by reduction, using for example a complex metal hydride such as lithium aluminium hydride or sodium borohydride in a solvent such as methanol.

In another example, alcohol —OH groups in the compounds may be converted to a corresponding —$OR^5$ or —$OR^{14}$ group by coupling with a reagent $R^5$OH or $R^{14}$OH in a solvent such as tetrahydrofuran in the presence of a phosphine, e.g. triphenylphosphine and an activator such as diethyl-, diisopropyl-, or dimethylazodicarboxylate.

Aminosulphonylamino [—$NHSO_2NHR^3$ or —$NHSO_2NHAr^1$] groups in the compounds may be obtained, in another example, by reaction of a corresponding amine [—$NH_2$] with a sulphamide $R^3NHSO_2NH_2$ or $Ar^1NHSO_2NH_2$ in the presence of an organic base such as pyridine at an elevated temperature, e.g. the reflux temperature.

In another example compounds containing a —$NHCSAr^1$, —$CSNHAr^1$, —$NHCSR^3$ or —$CSNHR^3$ may be prepared by treating a corrsponding compound containing a —NHCOAr$^a$, —CONHAr$^1$, —NHCOR$^3$ or —CONHR$^3$ group with a thiation reagent, such as Lawesson's Reagent, in an anhydrous solvent, for example a cyclic ether such as tetrahydrofuran, at an elevated temperature such as the reflux temperature.

In a further example amine (—NH$_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, where necessary in the presence of an acid such as acetic acid at around ambient temperature.

In a further example, amine [—NH$_2$] groups in compounds of formula (1) may be obtained by hydrolysis from a corresponding imide by reaction with hydrazine in a solvent such as an alcohol, e.g. ethanol at ambient temperature.

In another example, a nitro [—NO$_2$] group may be reduced to an amine [—NH$_2$], for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

Aromatic halogen substituents in the compounds may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyldisulphide as the electrophile.

In another example, sulphur atoms in the compounds, for example when present in a linker group L$^1$ or L$^2$ may be oxidised to the corresponding sulphoxide or sulphone using an oxidising agent such as a peroxy acid, e.g. 3-chloroperoxybenzoic acid, in an inert solvent such as a halogenated hydrocarbon, e.g. dichloromethane, at around ambient temperature.

In another example compounds of formula Ar$^1$X$^1$ (where X$^1$ is a halogen atom such as a chlorine, bromine or iodine atom) may be converted to such compounds as Ar$^1$CO$_2$R$^{20}$ (in which R$^{20}$ is an optionally substituted alkyl, aryl or heteroaryl group), Ar$^1$CHO, Ar$^1$CHCHR$^{20}$, Ar$^1$CCR$^{20}$, Ar$^1$N(R$^{20}$)H, Ar$^1$N(R$^{20}$)$_2$, for use in the synthesis of for example compounds of formula R$^1$R$^2$NH, using such well known and commonly used palladium mediated reaction conditions as are to be found in the general reference texts Encyclopedia of Reagents for Organic Synthesis, Editor-in Chief Paquette, L. A., John Wiley and Sons, 1995 and Comprehensive Organic Functional Group Transformations, Editors-in-Chief Katritzky, A. R. et al, Pergamon, 1995.

N-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

Chromatography, recrystallisation and other conventional separation procedures may also be used with intermediates or final products where it is desired to obtain a particular geometric isomer of the invention.

The following Examples illustrate the invention. All temperatures are in °C. The following abbreviations are used:
NMM—N-methylmorpholine;
MeOH—methanol;
DCM—dichloromethane;
DIPEA—diisopropylethylamine;
Pyr—pyridine;
DMSO—dimethylsulphoxide;
Et$_2$O—diethylether;
EtOAc—ethyl acetate;
BOC—butoxycarbonyl;
AcOH—acetic acid;
EtOH—ethanol,
Ar—aryl;
iPr—isopropyl;
Me—methyl;
THF—tetrahydrofuran,
FMOC—9-fluorenylmethoxycarbonyl;
obs—obscured;
dil—dilute;
Bu—butyl;
DMF—N,N-dimethylformamide;
br—broad;
app—apparent;
RT—room temperature;
DIPEA—diisopropylethylamine
All NMR's were obtained at 300 mHz.

Intermediate 1

3,5-Dichloropyridine-4-carboxylic acid

A solution of 3,5-dichloropyridine (5.00 g, 33.8 mmol) in THF (25 ml) was added to a solution of LDA [generated from nBuLi (2.5M solution in hexanes, 14.9 ml, 37.2 mmol) and diisopropylamine (4.10 g, 5.7 ml, 40.6 mmol)] in THF (25 ml) at −78° under nitrogen, to give a yellow/brown slurry. The reaction was stirred for 30 min at −78° then CO$_2$ gas was bubbled through to give a clear brown solution that slowly gave a precipitate, warmed to RT over 2 h, then quenched with water (20 ml) and partitioned between Et$_2$O (100 ml) and 1M NaOH (100 ml). The aqueous layer was separated and acidified to pH1 with concentrated hydrochloric acid and then extracted with 10% MeOH in DCM (100 ml×3). The combined organic layers were dried (MgSO$_4$) and the solvent removed under vacuum to give a brown solid that was recrystallised from ethanol and dried under vacuum to give the title compound as pinkish crystals (2.63 g, 41%). δH (DMSO-d$^6$) 8.74 (2H, s). δC (DMSO-d$^6$) 163.5, 147.7, 141.0, 126.7.

Intermediate 2

Ethyl (S)-3-(4-[3,5-dichloropyrid-4-ylcarboxamido] phenyl)-2-(t-butoxycarbonyl amino)propionate A slurry of the compound of Intermediate 1 (51.2 g, 0.267 mol) in DCM (195 ml) and thionyl chloride (195 ml, 2.67 mol) was treated with DMF (5 drops) and heated to reflux for 4 h. The reaction was concentrated in vacuo and azeotroped with toluene (2×50 ml) to give a yellow solid which was used without further purification. A solution of ethyl-(S)-3-(4-aminophenyl)-2-(t-butoxycarbonyl amino) propionate (130.8 g, 0.425 mol) in DCM (800 ml) was cooled to 0° and treated with NMM (56.0 ml, 0.51 mol), stirred 5 minutes and then a solution of the acid chloride (98.3 g, 0.468 mol) in DCM (200 ml) was added dropwise keeping the reaction temperature below 5°. The reaction was stirred for 1 h, quenched with NaHCO$_3$ solution (500 ml), the organic layer separated, washed with NaHCO$_3$ solution (500 ml), 10% citric acid solution (500 ml) and NaHCO$_3$ solution (500 ml), dried (MgSO$_4$) and concentrated in vacuo to give a yellow solid which was recrystallised (EtOAc/hexane) to give the title compound, 140 g, 69%. δH (DMSO d$^6$), 8.8 (2H, s), 7.55 (2H, d, J 8.5 Hz), 7.23 (2H, d, J 8.5 Hz), 4.0 (3H, m), 3.4 (2H, b s), 2.9 (1H, m), 2.8 (1H, m), 1.3 (9H, s), 1.25 (3H, t). m/z (ES$^+$, 70V) 504 (MNa$^+$).

Intermediate 3

Ethyl (S)-3-[4-(3,5-dichloropyrid-4-yl carboxamido) phenyl]-2-aminopropionate hydrochloride A solution of the compound of Intermediate 2 (70 g, 0.146 mol) in EtOAc (500 ml) and 1,4-dioxan (50 ml) was treated with a solution of HCl in EtOAc (500 ml, 3M), and stirred at RT for 4 h. The reaction was concentrated in vacuo to give a yellow solid which was triturated with Et$_2$O then recrystallised (EtOAc/hexane) to give the title compound (59.3 g, 92%). δH (DMSO d$^6$), 11.10 (1H, s), 8.70 (2H, s), 7.55 (2H, d, J 8.4 Hz), 7.25 (2H, d, J 8.4 Hz), 4.10 (3H, m), 3.10 (2H, m), 1.10 (3H, m). m/z (ES$^+$, 70V) 382 (MH$^+$).

Intermediate 4

3-(tert-Butyl)-4-isopropoxy-3-cyclobutene-1,2-dione tert-Butyl lithium (2.29 ml of a 1.7M solution in pentane, 3.9 mmol) was added to a solution of 3,4-diisopropoxy-3-cyclobutene-1,2-dione (594 mg, 3 mmol) in THF (30 ml) at −78° C. After 5 h trifluoroactic anhydride (636 µl, 4.5 mmol) was added and stirring continued at −78° C. for 30 min. The cold mixture was poured into NH$_4$Cl(aq), extraced with EtOAc, dried (Na$_2$SO$_4$) and evaporated in vacuo. Column chromatography (SiO$_2$; EtOAc/hexane, 15:85) gave the title compound as a mobile yellow oil (408 mg, 69%). δH (CDCl$_3$) 5.43 (1H, sept, J 6.2 Hz), 1.45 (6H, d, J 6.2 Hz) and 1.33 (9H, s); m/z (ES$^+$, 70V) 197 (M$^+$+H).

Intermediate 5

1-Chloro-2,6-naphthyridine

1-Hydroxy-2,6-naphthyridine (550 mg) [prepared according to the method of Sakamoto, T. et al Chem. Pharm. Bull. 33, 626, (1985)] was stirred with phosphorous oxychloride (10 ml) at 110° for 5 h. The volatiles were removed in vacuo and the residue treated carefully with ice. After diluting with water (to ~25 ml), solid NaHCO$_3$ was added to neutralise and the product extracted into EtOAc (2×80 ml). The combined organic extracts were dried (MgSO$_4$), evaporated in vacuo, and the crude product chromatographed (SiO$_2$; EtOAc) affording the title compound as a slightly yellow solid (420 mg, 68%). δH (CDCl$_3$) 9.35 (1H, s), 8.82 (1H, d, J 5.9 Hz), 8.48 (1H, d, J 5.6 Hz), 8.00 (1H, d, J 5.9 Hz), 7.74 (1H, d, J 5.6 Hz); m/z (ES$^+$, 70V) 165 and 167 (MH$^+$).

Intermediate 6

Ethyl (S)-3-{4-[(2,6-naphthyridin-1-yl)amino] phenyl}-2-[N-(t-butyloxycarbonyl)amino] propanoate Ethyl (S)-3-(4-aminophenyl)-2-[N-(t-butyloxycarbonyl) amino]propanoate (600 mg, 1.95 mmol), Intermediate 5 (350 mg, 2.13 mmol) and DIPEA (276 mg, 372 µl, 2.13 mmol) in 2-ethoxyethanol (0.5 ml) were stirred at 130° under N$_2$ for several hours. The reaction was partitioned between EtOAc (70 ml) and saturated aqueous NaHCO$_3$ (30 ml). The phases were separated and the aqueous layer re-extracted with EtOAc (3×30 ml). The combined organic extracts were washed with brine (10 ml), dried (MgSO$_4$) and evaporated in vacuo to afford a dark oil. Chromatography (SiO$_2$; 3% MeOH/DCM) gave the title compound as a dull orange foam (360 mg, 42%). δH (CDCl$_3$) 9.19 (1H, s), 8.67 (1H, d, J 5.9 Hz), 8.24 (1H, d, J 5.8 Hz), 7.66 (1H, d, J 5.9 Hz), 7.65 (2H, d, J 8.5 Hz), 7.21 (1H, d, J 5.8 Hz), 7.16 (2H, d, J 8.5 Hz), 7.15 (1H, obscured s), 5.05–4.97 (1H, m), 4.60–4.51 (1H, m), 4.19 (2H, q, J 7.1 Hz), 3.17–3.04 (2H, m), 1.44 (9H, s), 1.27 (3H, t, J 7.1 Hz); m/z (ES$^+$, 70V) 459 (MNa$^+$), 437 (MH$^+$).

Intermediate 7

Ethyl (S)-2-amino-3-{4-[(2,6-naphthyridin-1-yl) amino]phenyl}propanoate

Intermediate 6 (360 mg) was treated with a solution of trifluoroacetic acid (10 ml) and DCM (10 ml) and stirred at RT for 2 h. The volatiles were removed in vacuo and the residue was partitioned between EtOAc (80 ml) and saturated aqueous NaHCO$_3$ (30 ml). The phases were separated and the aqueous layer re-extracted with EtOAc (3×30 ml). The combined organic extracts were dried (MgSO$_4$) and evaporated in vacuo to afford the title compound as a dark orange viscous oil (280 mg, 100%). δH (CDCl$_3$) 9.18 (1H, s), 8.66 (1H, d, J 5.9 Hz), 8.22 (1H, d, J 5.8 Hz), 7.67 (1H, d, J 5.9 Hz), 7.64 (2H, d, J 8.5 Hz), 7.22 (2H, d, J 8.5 Hz), 7.19 (1H, d, J 5.8 Hz), 4.20 (2H, q, J 7.1 Hz), 3.73 (1H, dd, J 7.9, 5.1 Hz), 3.10 (1H, dd, J 13.6, 5.2 Hz), 2.87 (1H, dd, J 13.6, 7.9 Hz), 1.70 (3H, br s), 1.28 (3H, t, 7.1 Hz); m/z (ES$^+$, 70V) 337 (MH$^+$).

Intermediate 8

Methyl (S)-2-(t-butyloxycarbonylamino)-3-[4-(2,6-naphthyridin-1-yloxy)phenyl]propanoate To N-(t-butyloxycarbonyl)tyrosine methyl ester (1.42 g, 4.82 mmol) in dry DMF (10 ml) was added 1-chloro-2,6 naphthyridine (0.79 g, 4.82 mmol) and cesium carbonate (1.65 g, 5.06 mmol) and the reaction stirred at 45° under N$_2$ for 2 days. The DMF was evaporated, EtOAc added and washed (3×) with water, dried (MgSO$_4$), and evaporated in vacuo. The residue was chromatographed (SiO$_2$; 40 to 100% EtOAc/isohexane) to afford the title compound as white foam (1.61 g, 82%). δ$_H$ (CDCl$_3$) 9.29 (1H, s), 8.76 (1H, d, J 5.74 HZ), 8.17 (1H, d, J 5.74 Hz), 8.11 (1H, d, J 5.8 Hz), 7.43 (1H, d, J 5.8 Hz), 7.22–7.18 (3H, m), 5.03 (1H, br s), 4.61 (1H, br s), 3.75 (3H, s), 3.15–3.05 (2H, m), 1.44 (9H, s); m/z (ES$^+$, 70V) MH$^+$424.

Intermediate 9

Ethyl (S)-2-(N-t-butyloxycarbonylamino)-3-[4-(isoquinolin-1-ylamino)phenyl]propanoate A stirred solution of ethyl (S)-3-(4-aminophenyl)-2-(N-t-butyloxycarbonylamino)propanoate (3.08 g, 10.0 mmol), 1-chloroisoquinoline (1.80 g, 11.0 mmol) and N,N-diisopropylethylamine (1.42 g, 1.91 ml, 11.0 mmol) in 2-ethoxyethanol (1.0 ml) was heated at 130° for 4 h. The volatiles were removed in vacuo and the residue partitioned between EtOAc (120 ml) and saturated aqueous NaHCO$_3$ (50 ml). The phases were separated and the aqueous layer was re-extracted with EtOAc (80 ml). The combined organic extracts were washed with brine (30 ml), dried (MgSO$_4$) and evaporated in vacuo. The obtained dark oil was chromatographed (silica; 20–30% EtOAc/hexane) to afford the title compound as a pink oil which crystallised on standing (2.78 g, 64%). δH (CDCl$_3$) 8.07 (1H, d, J 5.8 Hz), 7.93 (1H, d, J 8.4 Hz), 7.72 (1H, d, J 7.5 Hz), 7.63 (1H, d), 7.61 (2H, d, J 8.5 Hz), 7.51 (1H, t, J 6.8 Hz), 7.23 (1H, br s), 7.10 (1H, br s), 7.10 (2H, d, J 6.8 Hz), 5.02 (1H, br d, J 8.0 Hz), 4.54 (1H, br m), 4.16 (2H, t, J 7.1 Hz), 3.05 (2H, br m), 1.43 (9H, s), 1.25 (3H, t, J 7.1 Hz); m/z (ES$^+$, 60V) 436 (MH$^+$).

Intermediate 10

(S)-Ethyl 2-amino-3-[4-(isoguinolin-1-ylamino)phenyl]propanoate

A stirred solution of Intermediate 9 (2.70 g) in EtOAc (100 ml) was treated with HCl gas until turbidity and precipitation was seen to occur. The reaction mixture was stirred at ambient temperatue for an addition 0.5 h. The reaction was purged with nitrogen then diluted with EtOAc (50 ml) and saturated aqueous NaHCO$_3$ (50 ml). Sufficient solid NaHCO$_3$ was added to ensure full neutrality. The phases were separated and the aqueous layer re-extracted with EtOAc (2×40 ml). The combined organic extracts were washed with brine (20 ml), dried (MgSO$_4$) and evaporated in vacuo to afford the title compound as a light orange oil (2.10 g, q). δH (CDCl$_3$) 8.06 (1H, d, J 5.8 Hz), 7.91 (1H, d, J 8.3 Hz), 7.71 (1H, d, J 7.9 Hz), 7.63 (1H, obs. signal), 7.59 (2H, d, J 8.4 Hz), 7.49 (1H, app.t, J 7.8 HZ), 7.25 (1H, br s), 7.15 (1H, d, J 8.4 Hz), 7.09 (1H, d, J 5.8 Hz), 4.17 (2H, q, J 7.2 Hz), 3.68 (1H, dd, J 7.7, 5.1 Hz), 3.06 (1H, dd, J 14.6, 5.1 Hz), 2.81 (1H, dd, J 13.6, 7.9 Hz), 1.58 (2H, br s), 1.26 (3H, t, J 7.0 Hz); m/z (ES$^+$, 60V) 435.9 (MH$^+$).

Intermediate 11

Ethyl (E)-3-{4-[(tert-Butoxycarbonyl)amino]phenyl}-2-propenoate

Ethyl 4-aminocinnamate (2.5 g, 13.1 mmol) was dissolved in THF (25 ml) and treated with di-tert-butyl dicarbonate (3.14 g). The solution was refluxed for 16 h and then allowed to cool. The product was extracted into EtOAc and washed with water and brine, dried over Na$_2$SO$_4$, filtered and the solvent removed. The crude product was purified by column chromatography (SiO$_2$; EtOAc/hexane 1:9) to give the title compound (2.82 g, 74%) as a white solid. δH (CDCl$_3$)7.62 (1H, d, J 16.0 Hz), 7.45 (2H, d, J 8.8 Hz), 7.38 (2H, d, J 8.8 Hz), 6.63 (1H, br s), 6.33 (1H, d, J 16.0 Hz), 4.12 (2H, q, J 7.1 Hz), 1.52 (9H, s), 1.25 (3H, t, J 7.1 Hz). m/z (ES$^+$, 70V) 314 (MNa$^+$).

Intermediate 12

Ethyl (3S)-3-{4-[(tert-Butoxycarbonyl)amino]phenyl}-3-{N-benzyl[(1R)-1-phenylethyl]amino}propanoate Intermediate 11 (1.0 g, 3.44 mmol) was dissolved in THF (25 ml), treated with sodium hydride and left to stir for 20 mins. (R)-(+)-N-Benzyl(methylbenzylamine (1.44 ml) in THF (25 ml) at 0° was treated with n-butyllithium (2.75 ml, 2.5M in hexanes) and the purple solution left to stir for 20 mins then cooled to −78° and the ester anion added slowly. The reaction mixture was stirred at −78° C. for 4 h then quenched with ammonium chloride solution, extracted into EtOAc, washed with water and brine, dried (Na$_2$SO$_4$), filtered and the solvent removed. The crude product was purified by column chromatography (SiO$_2$; CH$_2$Cl$_2$) to give the tile compound (1.14 g, 66%) as a white solid. δH (CDCl$_3$) 7.42–7.17 (14H, m), 6.45 (1H, br s), 4.39 (1H, dd, J 9.4, 5.5 Hz), 3.99 (1H, q, J 6.9 Hz), 3.93 (2H, qd, J 7.1, 2.4 Hz), 3.72 (1H, d, J 14.7 Hz), 3.64 (1H, d, J 14.7 Hz), 2.63 (1H, dd, J 14.7, 5.5 Hz), 2.52 (1H, dd, J 14.7, 9.5 Hz), 1.52 (9H, s), 1.22 (3H, d, J 6.9 Hz), 1.06 (3H, t, J 7.1 Hz). m/z (ES$^+$, 70V) 503 (MH$^+$).

Intermediate 13

Ethyl (3S)-3-amino-3-{4-[(tert-Butoxycarbonyl)amino]}phenyl-propanoate

Intermediate 12 (312 mg, 0.62 mmol) in MeOH (5 ml) was treated with formic acid (0.1 ml) and 10% palladium on carbon. The reaction mixture was heated to reflux for 30 mins then cooled, filtered through celite™ and the solvent removed to give the title compound (195 mg, 100%) as an oil. δH (CDCl$_3$) 8.05 (2H, br s), 7.28 (2H, d, J 8.5 Hz), 7.21 (2H, d, J 8.5 Hz,), 6.92 (1H, br s), 4.48 (1H, dd, J 8.4, 5.7 Hz), 4.05 (2H, q, J 7.1 Hz), 3.6 (1H, dd, J 17.2, 8.4 Hz), 2.79 (1H, dd, J 17.2, 5.7 Hz), 1.44 (9H, s), 1.14 (3H, t, J 7.1 Hz). m/z (ES$^+$, 70V) 331 (MNa$^+$).

Intermediate 14

Methyl (R)-3-[(tert-Butoxycarbonyl)amino]-3-(4-hydroxyphenyl)propanoate

Methyl (3R)-(3-amino)-3-(4-hydroxyphenyl)propanoate [S. G. Davies and O. Ichihara, Tetrahedron Asymmetry, (1991), 2, 183–186] (346 mg, 1.78 mmol) was dissolved in dioxan (5 ml) and sodium bicarbonate solution (5 ml) added. The solution was treated with di-tert-butyl dicarbonate (407 mg, 1.86 mmol) and stirred vigourously for 16 h. The solution was diluted with water, and the product extracted into EtOAc (×2), washed with water, brine, dried (Na$_2$SO$_4$), filtered and the solvent removed. The product was purified by column chromatography (SiO$_2$; CH$_2$Cl$_2$/MeOH 20:1) to give the title compound (211 mg, 42%) as a white solid. δH (CDCl$_3$) 7.06 (2H, d, J 8.6 Hz), 6.66 (2H, d, J 8.6 Hz), 5.48 (1H, br), 4.98 (2H, br m), 3.61 (3H, s), 2.78 (2H, m), 1.42 (9H, s). m/z (ES$^+$, 70V) 318 (MNa$^+$).

Intermediate 15

Methyl (3R)-3-[(tert-Butoxycarbonyl)amino]-3-{4-[(6,7-dimethoxy-4-quinazolinyl)oxy]phenyl}propanoate Intermediate 14 (420 mg, 1.42 mmol) in DMF (4 ml) was treated with potassium carbonate (394 mg) and 4-chloro-6, 7-dimethoxyquinazoline (320 mg). The solution was stirred for 48 h and then water (20 ml) was added. The mixture was extracted with EtOAc (×2), washed with water (×3), brine, dried ($Na_2SO_4$), filtered and the solvent removed to give the title compound (657 mg, 96%) as a foamy yellow solid. δH (DMSO $d^6$) 8.53 (1H, s), 7.53 (1H, s), 7.40 (2H, d, J 8.6 Hz), 7.37 (1H, s), 7.24 (2H, d, J 8.6 Hz), 4.96 (1H, m, CH), 3.98 (3H, s), 3.95 (3H, s), 3.57 (3H, s), 2.77 (2H, m), 1.36 (9H, s). m/z ($ES^+$, 70V) 484 ($MH^+$).

Intermediate 16

Methyl (3R)-3-Amino-3-{4-[(6,7-dimethoxy-4-quinazolinyl)oxy]phenyl}propanoate

Intermediate 15 (650 mg, 1.35 mmol) was dissolved in EtOAc (10 ml) and HCl gas was bubbled through. The reaction mixture was stirred for 2 h and the solvent removed to give the title compound (589 mg, 100%) as an oil. δH (DMSO $d^6$) 8.66 (1H, s), 7.65 (2H, d, J 8.7 Hz), 7.58 (1H, s), 7.44 (1H, s), 7.39 (2H, d, J 8.7 Hz), 3.99 (3H, s), 3.97 (3H, s), 3.58 (3H, s), 3.22 (1H, dd, J 16.3, 6.1 Hz), 3.05 (1H, dd, J 16.3, 8.5 Hz). m/z ($ES^+$, 70V) 384 ($MH^+$).

Intermediate 17

Methyl (S)-3-{4-[(3-phenyl-1-quinazolinyl)amino]-phenyl}-[2-(tert-butoxycarbonyl)amino]-propanoate Methyl (2S)-[2-(tert-butoxycarbonyl)amino]-3-(4-aminophenyl)propanoate (500 mg, 1.7 mmol) and 4-chloro-2-phenylquinazoline (408 mg) were dissolved in 2-ethoxyethanol (5 ml) with Hunigs base (0.6 ml) and the solution heated at 120° C. for 16 h. The solution was cooled and concentrated. The residue was purified by column chromatography ($SiO_2$; $CH_2Cl_2$/MeOH 25:1) to give the title compound (682 mg, 81%) as a brown foamy solid. δH ($CDCl_3$) 8.56 (2H, dd, J 7.5, 3.7 Hz), 8.10 (1H, m), 7.95 (1H, m), 7.88 (2H, d, J 8.5 Hz), 7.80 (1H, m), 7.70 (1H, m), 7.50 (3H, m), 7.23 (2H, d, J 8.5 Hz), 5.05 (1H, m), 4.65 (1H, m), 3.72 (3H, s), 3.49 (1H, m), 3.15 (2H, m), 1.45 (9H, s). m/z ($ES^+$, 70V) 499 ($MH^+$).

Intermediate 18

Methyl (S)-2-Amino-3-{4-[(3-phenyl-1-quinazolinyl)amino]phenyl}propanoate

Intermediate 17 (678 mg, 1.36 mmol) in EtOAc (30 ml) was saturated with HCl gas and stirred for 45 mins. The brown precipitate was filtered off and dried to give the title compound (518 mg, 96%) as a brown foamy solid. δH (DMSO $d^6$) 9.12 (1H, d, J 8.6 Hz), 8.83 (2H, m), 8.50 (1H, d, J 8.1 Hz), 8.44 (2H, d, J 7.1 Hz), 8.14 (1H, d, J 8.1 Hz), 8.10 (1H, t, J 8.1 Hz), 7.84 (2H, d, J 8.6 Hz), 7.70 (1H, d, J 7.1 Hz), 7.63 (2H, t, J 7.1 Hz), 7.40 (2H, d, J 8.5 Hz), 3.70 (3H, s), 3.67 (1H, m), 3.30 (1H, dd, J 14.0, 5.5 Hz), 3.18 (1H, dd, J 14.0, 7.4 Hz). m/z ($ES^+$, 70V) 399 ($MH^+$).

Intermediate 19

Ethyl (R)-3-Amino-3-[4-(tert-butoxycarbonyl)aminophenyl]porpanoate

Ethyl (3R)-3{-Benzyl[(1S)-1-phenylethyl]amino}-3-[4-(tert-butoxycarbonyl)amino phenyl]propanoate (1.18 g, 2.35 mmol) was dissolved in MeOH (10 ml) and formic acid (1 ml) and 10% palladium on carbon added and the mixture refluxed for 2 h. The reaction mixture was cooled, filtered through Celite® and concentrated to give the crude title compound which was used immediately in the next reaction. δH ($CDCl_3$) 7.34 (2H, d, J 8.1 Hz), 7.27 (2H, d, J 8.1 Hz), 7.10 (1H, br s), 4.59 (1H, m), 4.11 (2H, q, J 7.1 Hz), 3.14 (1H, dd, J 16.8, 7.9 Hz), 2.86 (1H, dd, J 16.8, 12.0 Hz), 1.20 (3H, t, J 7.1 Hz).

Intermediate 20

Ethyl (R)-3-amino-3-(4-aminophenyl)propanoate

Intermediate 19 was dissolved in EtOAc (25 ml) and the solution saturated with HCl gas. The solution was stirred at RT for 90 mins whilst a white precipitate formed. The solid was filtered and dried to give the title compound (570 mg, 88% over 2 steps) as a white solid. δH (DMSO $d^6$) 8.79 (2H, br s), 7.63 (2H, d, J 8.4 Hz), 7.36 (2H, d, J 8.4 Hz, 4.58 (1H, m), 3.98 (2H, q, J 7.1 Hz), 3.19 (1H, dd, J 16.3, 5.6 Hz), 2.99 (1H, dd, J 16.3, 9.1 Hz), 1.08 (3H, t, J 7.1 Hz). m/z ($ES^+$, 70V) 192 ($M-NH_3$).

Intermediate 21

Ethyl (R)-3-(4-Aminophenyl)-3-(tert-butoxycarbonylamino)propanoate

Intermediate 20 (550 mg, 1.96 mmol) was dissolved in dioxan (10 ml) and treated with sodium bicarbonate (1 g), water (10 ml) and di-tert-butyl dicarbonate (427 mg) and the mixture stirred for 16 h. Water was added and the product extracted into EtOAc (×2), washed with brine, dried ($Na_2SO_4$), filtered and concentrated to give the crude product which was purified by column chromatography ($SiO_2$; $CH_2Cl_2$/MeOH 20:1) to give the title compound (296 mg, 49%) as an oil. δH ($CDCl_3$) 7.07 (2H, d, J 8.3 Hz), 6.64 (2H, d, J 8.3 Hz), 5.28 (1H, br s), 4.99 (1H, m), 4.05 (2H, q, J 7.1 Hz), 2.82 (1H, dd, J 15.1, 6.5 Hz), 2.73 (1H, dd, J 15.1, 6.5 Hz), 1.42 (9H, s), 1.17 (3H, t, J 7.1 Hz). m/z ($ES^+$, 70V) 331 ($MNa^+$).

Intermediate 22

Ethyl (3R)-3-[(tert-Butoxycarbonylamino)]-3-[4-(2,6-naphthyridine-1-ylamino)phenylpropanoate Intermediate 21 (250 mg, 0.81 mmol) in 2-ethoxyethanol (2 ml) was treated with 1-chloro-2,6-naphthyridine (134 mg) and heated at 120° for 15 mins, then 100° C. for 1 h, then cooled and concentrated. The residue was extracted into EtOAc (×3), washed with sodium bicarbonate solution, brine, dried ($Na_2SO_4$), filtered and concentrated to give the crude product. The products were purified by column chromatography ($SiO_2$; $CH_2Cl_2$/MeOH 50:1–20:1–10:1) to give the deprotected compound (106 mg, 30%) as a brown gum and the title compound (98 mg, 36%) as a yellow gum. δH ($CDCl_3$) 9.18 (1H, s), 8.66 (1H, d, J 5.9 Hz), 8.20 (1H, d, J 5.8 Hz), 7.73 (1H, d, J 5.9 Hz), 7.65 (2H, d, J 8.5 Hz), 7.30 (2H, d, J 8.5 Hz), 7.19 (1H, d, J 5.8 Hz), 5.47 (1H, m), 5.08 (1H, m), 4.09 (2H, q, J 7.1 Hz), 2.83 (2H, t, J 6.4 Hz), 1.44 (9H, s), 1.20 (3H, t, J 7.1 Hz). m/z ($ES^+$, 70V) 437 ($MH^+$).

Intermediate 23

Ethyl (R)-3-Amino-3-[4-(2,6-naphthyridin-1-ylamino)phenylpropanoate

Intermediate 22 (100 mg, 1 mmol) was dissolved in EtOAc (5 ml) and saturated with HCl gas. The reaction mixture was stirred to give a precipitate which was filtered and dried to give the title compound which was combined with the material isolated from the previous reaction. δH (CDCl₃) 9.18 (1H, s), 8.65 (1H, d, J 5.9 Hz), 7.65 (2H, d, J 8.5 Hz,), 7.37 (2H, d, J 8.5 Hz), 7.19 (1H, d, J 5.7 Hz), 4.44 (1H, t, J 6.8 Hz), 4.15 (2H, q, J 7.1 Hz), 2.68 (2H, d, J 6.8 Hz), 1.25 (3H, t, J 7.1 Hz).

Intermediate 24

N-BOC-O-(2-Pyrimidinyl)-L-tyrosine methyl ester

A solution of N-BOC-L-tyrosine methyl ester (3.0 g, 10.2 mmol) in DMF (5 ml) was added to a suspension of NaH (60% in oil, 11.2 mmol, 447 mg) in DMF (10 ml). After 10 min, a solution of 2-chloropyrimidine (11.2 mmol, 1.28 g) in DMF (3 ml) was added and the mixture stirred overnight. The reaction was quenched with water, diluted EtOAc and washed with water and brine. The EtOAc layer was dried (Na₂SO₄) and concentrated in vacuo. Purification by column chromatography [SiO₂, EtOAc/hexane, 1:1] gave the title compound. δH (DMSO d₆) 8.62 (2H, d, J 4.8 Hz), 7.37 (1H, d, J 8.1 Hz), 7.28 (2H, d, J 8.4 Hz), 7.24 (1H, t, J 4.8 Hz), 7.09 (2H, d, J 8.4 Hz), 4.18 (1H, m), 3.01 (1H, dd, J 13.8, 4.6 Hz), 1.33 (9H, s).

Intermediate 25

O-(2-Pyrimidinyl)-L-tyrosine methyl ester hydrochloride

Removal of BOC group from Intermediate 24 (HCl/EtOAc) gave the title compound as a white solid. δH (DMSO d₆) 8.69 (3H, m), 8.63 (2H, d, J 4.9 Hz), 7.31–7.25 (3H, m), 7.15 (2H, d, J 8.6 Hz), 4.30 (1H, m), 3.69 (3H, s), 3.19 (1H, dd, J 14.5, 6.4 Hz), 3.12 (1H, dd, J 14.3, 7.2 Hz).

Intermediate 26

N BOC-O-(3,5-Dichloroisonicotinoyl)-L-tyrosine methyl ester

A solution of N-BOC-L-tyrosine methyl ester (2.95 g, 10 mmol) in THF (10 ml) was added to a suspension of NaH (60% in oil, 11 mmol, 440 mg) in THF (30 ml) at 0°. After 10 min, a solution of 3,5-dichloroisonicotinoyl chloride (11 mml, 2.32 g) in THF (10 ml) was added and the mixture stirred at RT for 4 h. NH₄Cl (aq) was added and the mixture extracted with DCM. The DCM extracts were dried (Na₂SO₄) and concentrated in vacuo. Recrystallisation (EtOAc/hexane) gave the title compound as white crystals (3.61 g, 77%). δH (DMSO d₆) 8.89 (2H, s), 7.39 (2H, d, J 8.5 Hz), 7.32 (1H, d, J 8.2 Hz), 7.23 (2H, d, J 8.5 Hz), 4.21 (1H, m), 3.62 (3H, s), 3.05 (1H, dd, J 13.8, 4.9 Hz), 2.89 (1H, dd, J 13.8, 10.5 Hz), 1.31 (9H). m/z (ES⁺, 70V) 410 (M⁺+Na).

Intermediate 27

O-(3,5-Dichloroisonicotinoyl)-L-tyrosine methyl ester hydrochloride

Intermediate 26 (3.61 g) in EtOAc (150 ml) was treated with HCl/EtOAc (3 m, 50 ml). The white precipitate produced was filtered off and dried to give the title compound as a white solid (1.93 g). δH (DMSO d₆) 8.90 (2H, s), 8.74 (3H, br), 7.42 (2H, d, J 8.5 Hz), 7.28 (2H, d, J 8.6 Hz), 4.31 (1H, m), 3.67 (3H, s), 3.25 (1H, dd, J 14.2, 6.0 Hz), 3.17 (1H, dd, J 14.1, 7.2 Hz). m/z (ES⁺, 70V) 369 (MH⁺).

Intermediate 28

3-Butyl-4-methoxy-3-cyclobutene-1,2-dione n-BuLi (8.13 ml of a 1.6M solution in hexane, 13 mmol) was added slowly to a solution of 3,4-dimethoxy-3-cyclobutene-1,2-dione (1.42 g, 10 mmol) in THF (100 ml) at −78°. After 2 h, trifluoroacetic anhydride (2.12 ml, 15 mmol) was added. After a further 30 min the cold solution was poured into NH₄Cl(aq) (100 ml) and EtOAc (100 ml) and stirred well. The aqueous layer was extracted with EtOAc. The organic extracts were washed with brine, dried (Na₂SO₄) and concentrated in vacuo. Column chromatography (SiO₂, EtOAc/hexane, 30:70) gave the title compound as a yellow oil (803 mg, 48%). δH (CDCl₃) 4.42 (3H, s), 2.60 (2H, t, J 7.6 Hz), 1.71–1.61 (2H, m), 1.44–1.32 (2H, m), 0.94 (3H, t, J 7.3 Hz). m/z (ES⁺, 70V) 169 (MH⁺).

Intermediate 29

Methyl (Z)-2-[(tert-butoxycarbonyl)amino]-3-(3-methoxy-4-nitrophenyl)-2-propenoate Activated manganese IV oxide (26 g) was added to a mixture of 3-methoxy-4-nitrobenzylalcohol (5.26 g, 28.7 mmol), N-(t-Butyloxycarbonyl)-α-(diethylphosphono) glycine methylester (described in WO99/47547) (8.91 g, 27.4 mmol) and DBU (4.29 ml, 28.7 mmol) in DCM (150 ml) at 0°. The mixture was stirred at RT overnight then filtered. The filtrate was washed with dil. HCl, dried (Na₂SO₄) and evaporated in vacuo. Recrystallisation from MeOH gave the title compound as pale brown crystals (4.6 g). δH (DMSO d₆) 8.94 (1H, br s), 7.91 (1H, d, J 8.4 Hz), 7.56 (1H, d, J 1.5 Hz), 7.36 (1H, dd, J 8.5, 1.3 Hz), 7.12 (1H, br s), 3.92 (3H, s), 3.75 (3H, s), 1.37 (9H, s). m/z (ES⁺, 70V) 375 (M⁺+Na).

Intermediate 30

Methyl 3-(4-amino-3-methoxyphenyl)-2-[(tert-butoxycarbonyl)amino]-2-propanoate

A mixture of Intermediate 29 (2.30 g, 6.53 mmol) and palladium on charcoal (10% Pd on carbon, 230 mg) in MeOH (65 ml) was stirred under a hydrogen atmosphere at RT overnight. The catalyst was filtered off and the filtrate concentrated in vacuo. Recrystallisation (Et₂O/hexane) gave the title compound as dark pink needles (1.62 g, 77%). δH (DMSO d₆) 7.12 (1H, d, J 7.9 Hz), 6.65 (1H, s), 6.51 (2H, s), 4.52 (1H, s), 4.49 (1H, s), 4.07 (1H, m), 3.72 (3H, s), 3.59 (3H, s), 2.81 (1H, dd, J 13.7, 5.4 Hz), 2.69 (1H, dd, J 13.1, 9.5 Hz), 1.32 (9H, s). m/z (ES⁺, 70V) 347 (MNa⁺).

Intermediate 31

Methyl 3-{4-[(6,7-dimethoxy-4-quinazolinyl) amino]-3-methoxyphenyl}-2-[(tert-butoxycarbonyl) amino]propanoate A mixture of intermediate 30 (486 mg, 1.5 mmol), 4-chloro-6,7-dimethoxy quinazoline (337 mg, 1.5 mmol) and diisopropylethylamine (261 μl, 1.5 mmol) in ethoxyethanol (1.5 ml) was heated at 120° for 24 h. The mixture was diluted with DCM, washed with dil. HCl and water, dried (Na₂SO₄) and concentrated in vacuo. Column chromatography (SiO₂: MeOH/DCM, 5:95) gave the title compound as a brown gum (720 mg, 94%). δH (DMSO d₆) 9.10 (1H, s, ArNH), 8.34 (1H, d, J 1.0 Hz), 7.85 (1H, d, J 1.4 Hz), 7.47–7.44 (2H, m), 7.40 (1H, d, J 8.0 Hz), 7.47–7.44 (2H, m), 7.40 (1H, d, J 8.0 Hz), 7.20 (1H, s), 7.07 (1H, s), 6.91 (1H, d, J 8.0 Hz), 4.34–4.28 (1H, m), 3.98 (3H, s), 3.98 (3H, s), 3.82 (3H, s) 3.70 (3H, s), 3.09 (1H, dd, J 13.8, 5.0 Hz), 2.95 (1H, dd, J 13.7, 10.0 Hz), 1.42 (9H, s). m/z (ES⁺, 70V) 573 (MH⁺).

Intermediate 32

Methyl 2-amino-3-{4-[(6,7-dimethoxy-4-quinazolinyl)amino]-3-methoxyphenyl}propanoate hydrochloride Dry HCl was bubbled into a solution of Intermediate 31 (715 mg, 1.4 mmol) in EtOAc (30 ml) for a few seconds.

The mixture was stirred at RT for 1 h. The precipitate was filtered off and dried to give the title compound as a brown solid (534 mg, 85%). δH (DMSO d$_6$, 370K) 8.57 (1H, s), 8.23 (1H br s), 7.43 (1H, d, J 7.9 Hz), 7.15 (1H, s), 6.95 (1H, dd, J 8.0, 1.5 Hz), 4.28 (1H, dd, J 7.1, 6.2 Hz), 4.02 (3H, s), 4.01 (2H, s), 3.82 (3H, s), 3.75 (3H, s), 3.31 (1H, dd, J 14.2, 6.1 Hz), 3.24 (1H, dd, J 14.2, 7.1 Hz). m/z (ES$^+$, 70V) 413 (MH$^+$).

Intermediate 33

Methyl (S)-2-[(tert-butoxycarbonyl)amino]-3-{4-[2-(2,6-dichlorophenyl)ethynyl]phenyl}propanoate Nitrogen was bubbled through a solution of N-BOC-L-4-iodophenylalanine methyl ester (1.50 g, 3.69 mmol) in toluene (20 ml) and triethylamine (10 ml). Bis(triphenylphosphine)palladium (II) chloride (10 mol %, 260 mg) and copper (I) iodide (20 mol %, 140 mg) were added. A solution of 2,6-dichlorophenylacetylene (949 mg, 5.55 mmol) in toluene (10 ml) was added by syringe-pump over 3 h. The mixture was stirred at RT for a further 3 h. The mixture was diluted with EtOAc, washed with dil. HCl and brine, dried (Na$_2$SO$_4$) and evaporated in vacuo. Column chromatography (SiO$_2$; EtOAc/hexane, 20:80) gave the title compound as a brown gum (1.61 g, 97%). δH (DMSO d$_6$), 7.60–7.58 (2H, m), 7.51 (2H, d, J 8.1 Hz), 7.42 (1H, dd, J 8.8, 7.4 Hz), 7.33 (2H, d, J 8.1 Hz), 4.21 (1H, br m), 3.73 (3H, s), 3.04 (1H, dd, J 13.8, 5.0 Hz), 2.88 (1H, dd, J 13.7, 10.0 Hz) and 1.31 (9H, s): m/z (ES$^+$, 70V) 470 (M$^+$+Na).

Intermediate 34

Methyl (S)-2-amino-3-{4-[2-(2,6-dichlorophenyl)ethynyl]phenyl}propanoate hydrochloride HCl gas was bubbled through a solution of the compound of Example 33 (1.6 g, 3.57 mmol) in EtOAc (70 ml) for 5 min. The mixture was stirred for 1 h at RT. The precipitate formed was filtered off and washed with ether to give the title compound as an off-white solid (1.21 g, 88%). δH (DMSO d$_6$), 8.73 (3H, br s), 7.60 (2H, d, J 8.0 Hz), 7.56 (2H, d, J 8.1 Hz), 7.44 (1H, dd, J 8.7, 7.6 Hz), 7.35 (2H, d, J 8.1 Hz), 4.30 (1H, t, J 6.6 Hz), 3.68 (3H, s), 3.25 (1H, dd, J 14.2, 6.1 Hz), 3.16 (1H, dd, J 14.0, 7.2 Hz); m/z (ES$^+$, 70V) 348 (M$^+$+H).

Intermediate 35

5-Methyl-4-[3H]quinazolinone

6-Methylanthranilic acid (5 g, 33 mmol) and formamidine acetate (0.4 g, 41 mmol) were refluxed in 2-ethyoxyethanol (50 ml) for 16 h. On cooling the solvent was removed in vacuo, the residue slurried in diethyl ether, the solid filtered, washed with diethyl ether and dried to yield 3.6 g of the title compound. δH (DMSO d$_6$), 7.97 (1H, s), 7.60 (1H, dd, J 7.9, 7.6 Hz), 7.43 (1H, d, J 8.0 Hz), 7.21 (1H, d, J 7.3 Hz), 2.76 (3H, s); m/z (ES$^+$70V)161 (MH$^+$).

Intermediate 36

4-Chloro-5-methylquinazoline

The compound of Intermediate 35 (4.1 g, 26 mmol) was refluxed in phosphorous oxychloride (60 ml) for 5 h. On cooling the phosphorous oxychloride was removed in vacuo and the residue quenched in ice cold saturated sodium bicarbonate. The resulting mixture was extracted with EtOAc (3×50 ml), washed with brine, dried (Mg$_2$SO$_4$), the solvent removed and the residue purified by column chromatography (silica 1:1 ethylacetate/isohexane) to yield the title compound as white solid. δH (DMSO d$_6$), 8.5 (1H, s), 7.7 (1H, dd) 7.8 (1H, d), 7.3 (1H, m)

Intermediate 37

Ethyl-(S)-3-{4-([5-methyl-4-quinazolinyl]amino)phenyl}-2-(t-butoxy-carbonyl)amino propanoate Ethyl-(S)-3-(4-aminophenyl)-2-[(t-butoxycarbonyl)amino]propanoate (413 mg, 1.4 mmol) and Intermediate 36 (250 mg, 1.4 mmol) were heated at reflux in EtOH (10 ml). The solution was cooled, solvent removed in vacuo, residue stirred in EtOAc (10 ml) and sat. sodium bicarbonate (10 ml), organic layer isolated, washed with sodium bicarbonate, brine, dried (MgSO$_4$) and the solvent removed, to yield the title compound as an off white solid (520 mg). δH (CDCl$_3$) 8.6 (1H, s), 7.8 (1H, br, s), 7.7 (1H, d, J 7.8 Hz), 7.6 (2H, m), 7.3 (1H, d, J 7.2 Hz), 7.2 (2H, d, J 8.7 Hz), 5.2 (1H, br m), 4.6 (1H, br m) 4.2 (2H, q, J 7.2 Hz), 3.15 (2H, br m), 3.1 (3H, s), 1.4 (9H, s), 1.25 (3H, t, J 7.2 Hz).

Intermediate 38

Ethyl-(S)-3-(4-[(5-methyl-4-quinazolinyl)amino]phenyl)-2-aminopropanoate

The compound of Intermediate 37 (1.1 g, 2.5 mmol) in DCM (4 ml) and trifluoroacetic acid (2 ml) was stirred for 1 h. The solution was poured onto saturated sodium bicarbonate and extracted with EtOAc (×3). The extracts were washed with brine, dried (MgSO$_4$), solvent removed in vacuo to give the title compound as yellow oil. δH (CDCl$_3$), 8.6 (1H, s), 7.8 (1H, br s), 7.7 (1H, d, J 8.4 Hz), 7.6 (3H, m), 7.3 (3H, m) 4.2 (2H, q, J 7.2 Hz), 3.7 (1H, m), 3.1 (1H, dd, J 13.6, 8.4 Hz), 3.0 (1H, s), 2.8 (1H, dd, J 13.6, 7.9 Hz), 1.3 (3H, t, J 7.2 Hz). m/z (ES$^+$, 70V) 351 (MH$^+$)

Intermediate 39

Methyl-2-amino-5-(trifluoromethoxy)benzoate

A mixture of 2-Bromo-4-trifluoromethoxy aniline (2.7 g, 10.6 mmol) palladium (II) acetate (360 mg,) triethylamine (9 ml) and 1,3-bis(diphenylphosphino)propane (651 mg) in anhydrous methanol (10 ml) and anhydrous dimethyl formamide (10 ml) were cooled in ice/methanol bath, and carbon monoxide gas was bubbled through for 10 min. The mixture was heated at 70° under a partially inflated balloon of carbon monoxide for 17 h. On cooling nitrogen was bubbled through the solution to dispense excess carbon monoxide, and the mixture was poured onto water (50 ml) and EtOAc (50 ml), filtered through Celite®, the organic layer isolated, and aqueous phase was extracted with EtOAc. The organic layers were combined, washed with water (×2), brine (×2), dried (MgSO$_4$), and the solvent removed in vacuo. The residue was distilled and the fraction boiling at 170°, 0.08 mbar collected to yield 1.8 g of a yellow liquid. δH (CDCl$_3$), 7.7 (1H, m), 7.1 (1H, m), 6.6 (1H, d, J 9.0 Hz), 3.9 (3H, s).

Intermediate 40

6-(Trifluoromethoxy)-4[3H]-quinazoline

Prepared in a similar manner to the compound of intermediate 35 from the compound of Intermediate 39. δH (DMSO d$_6$), 8.1 (1H, s), 7.9 (1H, s), 7.8 (2H, m).

Intermediate 41

4-Chloro-6-(trifluoromethoxy)quinazoline

Prepared from the compound of Intermediate 40 in a similar manner to that described for Intermediate 36. δH (CDCl$_3$), 9.1 (1H, s), 8.1 (1H, d, J 9.2 Hz), 80 (1H, m), 7.8 (1H, m); m/z (EI$^+$, 70V) 249/251.

Intermediate 42

Ethyl-(S)-3-(4-{[6-(trifluoromethoxy)-4-quinazolinyl]amino}phenyl-2[(t-butoxycarbonyl)amino]porpanoate Prepared from Intermediate 41 in a similar manner to that described for Intermediate 37. δH (CDCl$_3$), 8.7 (1H, s), 8.0 (1H, d, J 9.1 Hz), 7.8 (1H, br s), 7.6 (3H, m), 7.2 (2H, d, J 8.5 Hz), 5.0 (1H, br s) 4.5 (1H, br s), 4.2 (2H, q, J 7.2 Hz), 3.1 (2H, br s), 1.4 (9H, s), 1.2 (3H, t, J 7.2 Hz).

Intermediate 43

Ethyl (S)-3-(4-{[6-trifluoromethoxyl-4-quinazolinyl]amino}phenyl)-2-aminopropanoate Prepared from the compound of Intermediate 42 in a similar manner to that described for Intermediate 38. δH (CDCl$_3$), 8.7 (1H, s), 7.9 (1H, d, J 9.2 Hz), 7.7 (1H, br m), 7.6 (3H, m), 7.2 (2H, d, J 7.1 Hz), 4.2 (2H, q, J 7.2 Hz), 3.8 (1H, m), 3.1 (1H, m), 2.9 (1H, m), 1.3 (3H, t, J 7.2 Hz); m/z (EI$^+$, 70V) 421 (MH$^+$)

Intermediate 44

3-Amino-4-methoxy-3-cyclobutene-1,2-dione 3,4-Dimethoxy-3-cyclobutene-1,2-dione (1.3 g, 9.2 mmol) in of MeOH (10.0 ml) was treated with aqueous ammonia (10.0 ml of a 2.0M solution) and stirred at ambient temperature for 2 h. The yellow precipitate thus formed was recovered by filtration, washed with MeOH and Et$_2$O and dried in vacuo to afford the title compound (0.87 g, 75%) as an amorphous yellow powder δH (d$^6$ DMSO) 8.32 (2H, br s), 4.28 (3H, s). m/z (ES$^+$, 70V) 127 (MH$^+$).

Intermediate 45

Methyl-(S)-3-{4-[(2-chloro-6,7-dimethoxy-4-quinazolinyl)amino]phenyl}-2-[(t-butoxycarbonyl)amino]proganoate Prepared in a similar manner to the compound of Intermediate 9 from methyl-(S)-3-(4-aminophenyl)-2-(N-t-butoxycarbonylamino)propanoate and 2,4-dichloro-6,7-dimethoxyquinazoline. δH (CD$_3$OD) 7.72 (1H, s), 7.69 (2H, d, J 8.4 Hz), 7.25 (2H, d, J 8.4 Hz), 7.05 (1H, s), 4.34 (1H, m), 4.15 (2H, m, J 7.1 Hz), 4.00 (3H, s), 3.96 (3H, s), 3.08 (1H, m), 2.97 (1H, m), 1.40 (9H, s), 1.23 (3H, t, J 7.1 Hz). m/z (ESI$^+$ 531 (MH$^+$).

EXAMPLE 1

Ethyl (S)-3-[4-(3,5-dichloro-4-pyridylcarboxamido)phenyl]-2-(2-isopropoxy-3,4-dioxocylobut-1-enylamino)propanoate A solution of Intermediate 3 (2.1 g, 5 mmol) in EtOH (25 ml) was treated with DIPEA (0.96 ml, 5.5 mmol) and 3,4-diisopropoxy-3-cyclobutene-1,2-dione (1.1 g, 5.5 mmol) and heated to reflux for 16 h. The reaction mixture was cooled and concentrated in vacuo. The residue was taken up in EtOAc (50 ml) and washed with 10% aqueous citric acid (2×50 ml), NaHCO$_3$ solution (2×30 ml) and brine (30 ml), dried (MgSO$_4$) and the solvent evaporated in vacuo to give a pale yellow oil, which was purified by column chromatography (SiO$_2$, EtOAc:hexane 1:1) to give the title compound as a white foam 1.62 g, 62%). δH (DMSO d$^6$), 10.45 (1H, s), 8.69 (2H, s), 8.52 (1H, d, J 8.4 Hz), 7.57 (2H, d, J 7.6 Hz), 7.25 (2H, d, J 7.6 Hz), 5.22 (1H, m), 4.69 (1H, m), 4.19 (2H, q, J 7.1 Hz), 3.25 (1H, dd, J 14.3, 5.2 Hz), 3.07 (1H, dd, J 14.3, 9.4 Hz), 1.38 (6H, dd, J 6.2, 3.9 Hz), 1.23 (3H, t, J 7.1 Hz).

EXAMPLE 2

Ethyl-(S)-3-[4-(3,5-dichloro-4-pyridylcarboxamido)phenyl]-2-(2-[3-methoxypropylamine]-3,4-dioxocyclobut-1-enylamino)propanoate A solution of the compound of Example 1 (1.55 g, 2.99 mmol) in EtOH (25 ml) was treated with 3-methoxypropylamine (0.34 ml, 3.3 mmol) and stirred for 16 h at RT. The white solid was isolated by filtration, and washed with cold Et$_2$O (3×10 ml) to give the title compound (1.38 g, 84%). δH (DMSO d$^6$), 10.89 (1H, s), 8.80 (2H, s), 7.59 (2H, d,J 8.4 Hz), 7.25 (2H, br m), 7.18 (2H, d, J 8.4 Hz), 4.99 (1H, m), 4.18 (2H, q, J 7.1 Hz), 3.54 (2H, m), 3.37 (2H, t, J 6.3 Hz), 3.23 (3H, s), 3.16 (1H, m), 3.06 (1H, m), 1.75 (2H, q. J 6.3 Hz), 1.22 (3H, t, J 7.1 Hz). m/z (ES$^+$, 70V) 549 (MH$^+$).

EXAMPLE 3

(S)-3-[4-(3,5-Dichloro-4-pyridylcarboxamido)phenyl]-2-[2-(3-methoxypropylamino)-3,4-dioxocyclobut-1-enylamino)propanoic acid A solution of the compound of Example 2 (1.30 g, 2.48 mmol) in THF (40 ml) and water (25 ml) was treated with LiOH.H$_2$O (125 mg, 2.98 mmol) and stirred for 3 h at RT. The reaction mixture was concentrated in vacuo, and acidified to pH 2 with 1M hydrochloric acid. The resulting solid was isolated by filtration, washed with water and dried in vacuo to give the title compound (1.15 g, 85%). δH (DMSO d$^6$), 10.89 (1H, s), 8.79 (2H, s), 7.58 (3H, m), 7.19 (2H, d, J 8.1 Hz), 4.92 (1H, m), 3.54 (2H, m), 3.23 (3H, s), 3.16 (1H, dd, J 13.9, 5.1 Hz), 3.05 (1H, dd, J 13.9, 7.4 Hz) and 1.74 (2H, t, J 6.4 Hz). m/z (ES$^+$, 70V) 521 (MH$^+$).

EXAMPLE 4

Ethyl-(S)-3[4-(3,5-dichloro-4-pyridylcarboxamido)phenyl]-2-(2-propylamino-3,4-dioxocyclobut-1-enylamino)propanoate A solution of the compound of Example 1 (1 g, 1.93 mmol) in EtOH (25 ml) was treated with n-propylamine (0.18 ml, 2.12 mmol) and stirred at RT for 16 h. The resulting white solid was isolated by filtration and washed with cold Et$_2$O (2×20 ml) to give the title compound (0.68 g, 68%). δH (DMSO d$^6$), 10.87 (1H, s), 8.78 (2H, s), 7.57 (4H, m,), 7.16 (2H, d, J 8.3 Hz), 4.97 (1H, m), 4.16 (2H, q, J 7.1 Hz), 3.44 (2H, m), 3.11 (2H, m), 1.50 (2H, m), 1.20 (3H, t, J 7.1 Hz), 0.86 (3H, t, J 7.1 Hz). m/z (ES$^+$, 70V) 519 (MH$^+$).

EXAMPLE 5

(S)-3-[4-(3,5-Dichloro-4-pyridylcarboxamido)phenyl]-2-(2-propylamino-3,4-dioxocyclobut-1-enylamino)propanoic acid The title compound (0.67 g, 99%) was prepared from the compound of Example 4 (0.66 g, 1.27 mmol) in a similar manner to the compound of Example 3. δH (DMSO d$^6$), 10.51 (1H, s), 8.71 (2H, s), 7.56 (2H, d, J 8.3 Hz), 7.36 (1H, m), 7.31 (1H, d, J 9.0 Hz), 7.22 (2H, d, J 8.3 Hz), 4.96 (1H, m), 3.49 (2H, q, J 6.7 Hz), 3.20 (1H, dd, J 14.1,5.6 Hz), 3.09 (1H, dd, J 14.1, 7.4 Hz), 1.57 (2H, m), 0.92 (3H, t, J 7.4 Hz). m/z (ES+, 70V) 491 (MH+).

EXAMPLE 6

Ethyl (S)-3-[4-(3,5-dichloro-4-pyridylcarboxamido)phenyl]-2-[(2-tert-butyl)-3,4-dioxo-1-cyclobutenylamino]porpanoate A mixture of the compound of Intermediate 4 (392 mg, 2 mmol), Intermediate 3 (837 mg, 2 mmol) and DIPEA (348 μl, 2 mmol) in abs. ethanol (20 ml) was heated at reflux for 24 h. The solvent was removed in vacuo and the residue dissolved in DCM, washed with HCl (1M), dried ($Na_2SO_4$) and evaporated in vacuo. Column chromatography ($SiO_2$; MeOH/DCM, 5:95) gave the title compound as a yellow foam (741 mg, 72%). δH (DMSO $d_6$), 10.83 (1H, s), 8.77 (2H, s), 8.54 (1H, d, J 8.6 Hz,), 7.54 (2H, d, J 8.4 Hz), 7.23 (2H, d, J 8.5 Hz), 5.01 (1H, m), 4.17 (2H, q, J 7.1 Hz), 3.25 (1H, dd, J 4.6 Hz), 3.04 (1H, dd, J 13.7, 10.9 Hz), 1.21 (9H, s), 1.21 (3H, t, J 7.1 Hz). m/z (ES+, 70V) 518 (M++H).

EXAMPLE 7

(S)-3-[4-(3,5-Dichloro-4-pyridylcarboxamido)phenyl]-2-[(2-tert-butyl)-3,4-dioxo-1-cyclobutenylamino]propanoate Lithium hydroxide monohydrate (66 mg, 1.56 mmol) was added to the compound of Example 6 (735 mg, 1.42 mmol) in THF (14 ml) and water (14 ml). After 2.5 h at RT the THF was removed in vacuo. The aqueous residue was acidified (pH1, 1M HCl) and the precipitate filtered off, washed with water and dried to give the title compound as a pale brown solid (625 mg, 90%). δH (DMSO $d_6$), 13.29 (1H, br s), 10.85 (1H, s), 8.78 (2H, s), 8.49 (1H, d, J 9.2 Hz), 7.55 (2H, d, J 8.5 Hz), 7.24 (2H, d, J 8.5 Hz), 4.95 (1H, ddd, J 11.0, 9.3, 4.2 Hz), 3.28 (1H, dd, J 13.8, 4.1 Hz), 3.04 (1H, dd, J 13.7, 1.1 Hz), 1.22 (9H, s); m/z (ES+, 70V) 490 (M++H).

EXAMPLE 8

Methyl (S)-3-{4-[(3,5-dichloroisonicotinoyl)oxy]phenyl}-2-(2-propylamino-3,4-dioxocyclbut-1-enylamino)propanoate In a similar manner to that described for Example 1 and Example2 the title compound was prepared from the compound of Intermediate 27 as a white solid. δH (DMSO $d_6$, 390K) 8.81 (2H, s) 736 (2H, d, J 8.7 Hz), 7.26 (2H, d, J 8.7 Hz), 5.11–5.05 (1H, m), 3.78 (3H, s), 3.52–3.47 (2H, m) 3.29 (1H, dd, J 14.2, 5.9 Hz), 3.18 (1H, dd, J 14.2, 9.7 Hz), 1.63–1.54 (2H, m), 0.93 (3H, t, J 7.4 Hz,). m/z (ES+, 70V) 506 (MH+).

EXAMPLE 9

(S)-3-{4-[(3,5-Dichloroisonicotinoyl)oxy]phenyl}-2-(2-propylamino-3,4-dioxocyclobut-1-enylamino)propanoic acid In a similar manner to that described for Example 3 the title compound was prepared from Example 8 as a white solid. δH (DMSO $d_6$, 390K) 13.31 (1H, br), 8.80 (2H, s), 7.38 (2H, d, J 8.6 Hz), 7.25 (2H, d, J 8.6 Hz), 5.0–4.98 (1H, m), 3.52–3.47 (2H, m,) 3.29 (1H, dd, J 14.2, 5.7 Hz), 3.16 (1H, dd, J 14.2, 7.5 Hz), 2.51–2.50 (2H, m), 0.93 (3H, t, J 7.4 Hz). m/z (ES+, 70V) 494 (MH+).

EXAMPLE 10

Ethyl (S)-3-[4-(3,5-dichloro-4-pyridylcarboxamido)phenyl]-2-(2-butyl-3,4-dioxo-1-cyclobutenylamino)propanoate A mixture of Intermediate 28 (336 mg, 2 mmol), Intermediate 3 (837 mg, 2 mmol) and DIPEA (700 μl, 4 mmol) in EtOH (2 ml) was heated at reflux for 2 h. The solvent was removed in vacuo. The residue was dissolved in DCM (150 ml), washed with dil. HCl, dried ($Na_2SO_4$) and concentrated in vacuo. Column chromatography ($SiO_2$: MeOH/DCM, 5:95) gave the title compound as a yellow foam (904 mg, 87%). δH (DMSO $d_6$, 390K) 10.39 (1H, br s), 8.68 (2H, s), 8.59 (1H, br d, J 7.8 Hz), 7.55 (2H, br s), 7.26 (2H, d, J 8.3 Hz), 4.84 (1H, br s), 4.21 (2H, q, J 7.1 Hz), 3.28 (1H, dd, J 14.3, 5.3 Hz), 3.10 (1H, dd, J 14.3, 9.2 Hz), 2.5 (2H, m), 1.62–1.54 (2H, m), 1.38–1.29 92H), 1.24 (3H, t, J 7.1 Hz, $CO_2CH_2CH_3$), 0.91 (3H, t, J 7.3 Hz). m/z (ES+, 70V) 518 (MH+).

EXAMPLE 11

(S)-3-{4-(3,5-Dichloro-4-pyridylcarboxamido)phenyl]-2-(2-butyl-3,4-dioxo-1-cyclobutenylamino)propanoic acid In a similar manner to that described for Example 3 the title compound was prepared from the compound of Example 10 as a pale yellow solid. δH (DMSO $d_6$, 370K), 10.48 (1H, s), 8.70 (2H, s), 8.5 (1H, v br), 7.55 (2H, d, J 7.8 Hz), 7.25 (2H, d, J 7.9 Hz), 4.85 (1H, v br), 3.29–3.22 (1H, m), 3.09–3.03 (1H, m), 2.5 (2H, m), 1.57–1.51 (2H, m), 1.36–1.27 (2H, m), 0.90 (3H, t, J 7.3 Hz). m/z (ES+, 70V) 490 (MH+).

EXAMPLE 12

Ethyl (S)-3-{4-[(2,6-naphthyridin-1-yl)amino]phenyl}2-[(2-isopropoxy-3,4-dioxocyclobut-1-enyl)amino]propanoate A solution of Intermediate 7 (280 mg, 0.84 mmol) and 3,4-diisopropoxy-3-cyclobuten-1,2-dione (200 mg, 1.01 mmol) in absolute ethanol (5 ml) was stirred at RT for 8 h then at 50° for 18 h. The volatiles were removed in vacuo and the residue chromatographed (silica, 80% EtOAc/Hexane to 100% EtOAc) affording the title compound as a dull yellow foam (250 mg, 63%). δH ($CDCl_3$) 9.18 (1H, s), 8.66 (1H, d, J 5.9 Hz), 8.21 (1H, d, J 5.7 Hz), 7.72 (1H, d, J 5.9 Hz), 7.66 (2H, d, J 8.5 Hz), 7.22 (1H, obs. s), 7.20 (1H, d, J 5.7 Hz), 7.14 (2H, d, J 8.5 Hz), 6.37, 5.90, 5.18 and 4.60 (together 1H, br m's), 4.27 (2H, q, J 7.1 Hz), 3.31–3.10 (2H, br m), 1.42 (3H, d, J 6.2 Hz), 1.41 (3H, d, J 6.2 Hz), 1.32 (3H, t, J 7.1 Hz); m/z (ES+, 70V) 475 (MH+).

EXAMPLE 13

Ethyl (S)-3-{4-[(2,6-naphthyridin-1-yl)amino]phenyl}2-{[2-N,N-diethylamino-3,4-dioxocyclobut-1-enyl]amino}propanoate The compound of Example 12 (240 mg, 0.51 mmol) and diethylamine (74 mg, 105 μl, 1.01 mmol) in absolute ethanol (2 ml) was stirred at 45° under an atmosphere of $N_2$ for 18 h. The volatiles were removed in vacuo and the residue chromatographed (silica, gradiant elution 1 to 3% EtOH/EtOAc) to afford the title compound as a yellow foam (240 mg, 97%). δH ($CDCl_3$) 9.17 (1H, s), 8.65 (1H, d, J 5.9 Hz), 8.19 (1H, d, J 5.7 Hz), 7.78 (1H, d, J 5.9 Hz), 7.68 (2H, d, J 8.4 Hz), 7.48 (1H, s), 7.18 (1H, d, J 5.7 Hz), 7.13 (2H, d, J 8.4 Hz), 5.45–5.35 (2H, overlapping signals), 4.25 (2H, q, J 7.1 Hz), 3.68–3.31 (4H, br m), 3.30–3.18 (2H, m), 1.31 (3H, t, J 7.1 Hz), 1.22 (6H, t, J 7.1 Hz); m/z (ES$^+$, 70V) 488 (MH$^+$).

EXAMPLE 14

(S)-3-{4-[(2,6-Naphthyridin-1-yl)amino]phenyl}2-{[2-N,N-diethylamino-3,4-dioxocyclobut-1-enyl]amino}propanoic acid The compound of Example 13 (230 mg, 0.47 mmol) was treated with a solution of LiOH.H$_2$O (25 ml, 0.60 mmol) in water (4 ml) and dioxan (4 ml) at RT for 1.5 h. A few drops of AcOH were added and the volatiles removed in vacuo. The residue was chromatographed [silica, gradiant elution, DCM (200 to 120), MeOH (20), AcOH (3), H$_2$O (2)] to afford the product as a yellow oil. Freeze-drying from aqueous MeOH afforded the title compound as a bright yellow amorphous solid (165 mg, 76%). δH (d$_6$ DMSO) 9.28 (1H, s), 9.20 (1H, s), 8.65 (1H, d, J 5.9 Hz), 8.37 (1H, d, J 5.8 Hz), 8.12 (1H, d, J 5.8 Hz), 7.78 (2H, d, J 8.5 Hz), 7.66 (1H, d, J 9.0 Hz), 7.26 (1H, d, J 5.8 Hz), 7.22 (2H, d, J 8.5 Hz), 5.15–5.05 (1H, m), 3.70–3.30 (4H, br m), 3.22 (1H, dd, J 13.9, 4.0 Hz), 3.00 (1H, dd, J 13.9, 10.9 Hz), 1.09 (6H, t, J 7.1 Hz); m/z (ES$^+$, 70V) 460 (MH$^+$).

EXAMPLE 14A (S)-3-{4-[(2,6-Naphthyridin-1-yl)amino]phenyl}-2-{[2-N,N-diethylamino-3,4-dioxocyclobut-1-enyl]amino}propanoic acid, sodium salt A solution of the compound of Example 14 (250 mg, 0.55 mmol) in water (3 ml) and THF (2 ml) was treated with sodium hydroxide solution (0.1M, 5.5 mmol) and stirred for 10 mins. The solution was freeze dried to give the title compound as a bright orange solid (250 mg, 95%). δH (d$_6$ DMSO) 8.43 (1H, s), 8.06 (2H, s), 7.48 (1H, d, J 5.6 Hz), 7.16 (2H, d, J 8.3 Hz), 6.93 (2H, d, J 8.4 Hz), 5.88 (1H, d, J 5.6 Hz), 3.73 (1H, t, J 6.7 Hz), 3.88–3.83 (2H, m), 3.55–3.50 (2H, m), 2.86 (1H, dd, J 13.3, 6.5 Hz), 2.67 (1H, m), 1.12 (6H, t, J 7.1 Hz). (ES$^+$, 70V) 460 (MH$^+$).

In a similar manner to that described for Examples 13 and 14 were prepared the Examples 15 to 28:

EXAMPLE 15

Ethyl (S)-3-[4-(2,6-naphthyridin-1-ylamino)phenyl]2-[2-piperidin-1-yl)-3,4-dioxocyclobut-1-enylamino]propanoate δ$_H$ (CDCl$_3$) 9.18 (1H, s), 8.67 (1H, d, J 5.9 Hz), 8.20 (1H, d, J 5.9 Hz), 7.74 (1H, d, J 5.9 Hz), 7.67 (2H, d, J 8.5 Hz), 7.35 (1H,s), 7.20 (1H, d, J 5.9 Hz), 7.13 (2H, d, J 8.5 Hz), 5.40 (2H, narrow m), 4.25 (2H,q, J 7.2 Hz), 3.69–3.50 (4H, br m), 3.22 (2H, narrow m), 1.67 (6H, narrow m), 1.31 (3H, t, J 7.2 Hz); m/z (ES$^+$, 70V) (MH$^+$) 500.

EXAMPLE 16

(S)-3-[4-(2,6-Naphthyridin-1-ylamino)phenyl]-2-[2-(piperidin-1-yl)-3,4-dioxocyclobut-1-enylamino]propanoic acid δ$_H$ (d$_6$ DMSO) 9.29 (1H, s), 9.21 (1H, s), 8.65 (1H, d, J 5.9 Hz), 8.38 (1H, d, J 5.9 Hz), 8.12 (1H, d, J 5.8 Hz), 7.77 (2H, d, J 8.4 Hz), 7.76 (1H, obs. signal), 7.26 (1H, d, J 5.8 Hz), 7.21 (2H, d, J 8.4 Hz), 5.07 (1H, narrow m), 3.72–3.48 (4H, br m), 3.20 (1H, dd, J 14.0, 4.1 Hz), 2.98 (1H, dd, J 14.0, 10.6 Hz), 1.68–1.49 (6H, br m); m/z (ES$^+$, 70V) (MH$^+$) 472.

EXAMPLE 17

Ethyl (S)-3-[4-(2,6-naphthyridin-1-ylamino)phenyl]-2-(2-N,N-di-n-propylamino-3,4-dioxocyclobut-1-enylamino)propanoate δ$_H$ (CDCl$_3$) 9.18 (1H, s), 8.70 (1H, d, J 5.9 Hz), 8.15 (1H, s), 7.85 (1H, br s), 7.64 (2H, d, J 8.3 Hz), 7.19–7.13 (3H, m), 5.40–5.30 (1H, m), 4.35–4.20 (2H, m), 3.60–3.10 (6H, m), 1.65–1.55 (4H, m), 1.33 (3H, t, J 7.1 Hz), 0.9 (6H, t, J 7.35 Hz), m/z (ES$^+$, 70V) MH$^+$516.

EXAMPLE 18

(S)-3-[4-(2,6-Naphthyridin-1-ylamino)phenyl]-2-(2-N,N-di-n-propylamino-3,4-dioxocyclobut-1-enylamino)propanoic acid δ$_H$ (d$_6$ DMSO, 370K) 9.19 (1H, s), 9.0 (1H, br s), 8.64 (1H, d, J 8.6 Hz), 8.34 (1H, d,J 5.9 Hz), 8.14 (1H, d, J 5.7 Hz), 7.79 (2H, d, J 8.4 Hz), 7.25–7.21 (1H, m), 7.23 (2H, d, J 8.7 Hz), 7.05 (1H, br s), 5.15 (1H, br s), 3.56–3.40 (4H, m), 3.27 (1H, dd, J 14.2, 4.9 Hz), 3.10 (1H, dd, J 14.2, 9.4 Hz), 1.65–1.50 (4H, m), 0.86 (6H, t, J 7.3 Hz), m/z (ES$^+$, 70V) MH$^+$ 488.

EXAMPLE 19

(S)-3-[4-(2,6-naphthyridin-1-ylamino)phenyl]2-(2-tert-butyl-3,4-dioxocyclobut-1-enylamino)-propanoic acid δ$_H$ (d$_6$ DMSO) 9.29 (1H, s), 9.22 (1H, s), 8.67 (1H, d, J 5.8 Hz), 8.51 (1H, d, J 9.1 Hz), 8.40 (1H, d, J 0.8 Hz), 8.38 (1H, d, J 0.8 Hz), 8.13 (1H, dd, J 5.6, 1.3 Hz), 7.78 (2H, nr m), 7.26 (1H, d, J 5.8 Hz), 7.19 (1H, d, J 8.6 Hz), 4.95 (1H, br s), 3,4–3.2 (1H, m), 3.04 (1H, dd, J 13.6, 11.1 Hz), 1.23 (9H, s). m/z (ES$^+$, 70V) (MH$^+$) 445.2.

EXAMPLE 20

(S)-3-[4-(2,6-Naphthyridin-1-ylamino)phenyl]-2-[2-N-methyl-N-butylamino)-3,4-dioxocyclobut-1-enylamino]propanoic acid δH (d$_6$ DMSO, 390K) 9.19 (1H, s), 9.08 (1H, s), 8.65 (1H, d, J 5.9 Hz), 8.35 (1H, d, J 5.9 Hz), 8.35 (1H, d, J 5.9 Hz), 8.14 (1H, d, J 5.7 Hz), 7.78 (2H, d, J 8.3 HZ), 7.25–7.20 (3H, m), 5.06 (1H, br s), 3.58–3.42 (2H, m), 3.24 (1H, dd, J 14.1, 4.7 Hz), 3.16 (3H, s), 3.06 (1H, dd, J 14.1, 9.5 Hz), 1.54–1.50 (2H, m), 1.27 (2H, dd, J 15.1, 7.4 Hz), 0.87 (3H, t, J 7.31 HZ). m/z ES$^+$, 70V) 474 (MH$^+$).

EXAMPLE 21

(S)-3-[4-(2,6-Naphthyridin-1-yl-N-methylamino)phenyl]-2-[2-N,N-diethylamino-3,4-dioxocyclobut-1-enylamino)propanoic acid δH (d$_6$ DMSO, 350K) 9.23 (1H, d, J 1.0 Hz), 8.36 (1H, d, J 5.6 Hz), 8.22 (1H, d, J 6.0 Hz), 7.49 (1H, dd, J 5.7, 0.9 Hz), 7.30 (1H, br d, J 8.0 Hz), 7.21 (2H, d, J 8.5 Hz), 7.05 (1H, d, J 6.0 Hz), 6.93 (2H, d, J 8.5 Hz), 5.12–5.09 (1H, narrow m), 3.66–3.45 (4H, m), 3.49 (3H, s), 3.24 (1H, dd, J 14.0–4.5 Hz), 3.03 (1H, dd, J 14.0, 10.1 Hz), 1.10 (6H, t, J 7.1 Hz) m/z (ES$^+$, 70V) 474 (MH$^+$).

EXAMPLE 22

(S)-3-[4-(2,6-Naphthyridin-1-ylamino)phenyl]-2-[(2,5-dimethyl-3-pyrrolin-1-yl)-3,4-dioxocyclobut-1-enylamino]propanoic acid δH (DMSO $d_6$, 350K); 9.19 (1H, d, J 0.9 Hz), 9.09 (1H, s), 8.65 (1H, d, J 5.9 Hz), 8.35 (1H, d, 5.9 Hz), 8.14 (1H, d, J 5.7 Hz), 7.78 (2H, d, J 8.3 Hz), 7.26–7.18 (4H, m), 5.90 (2H, s), 5.09 (1H, br s), 4.85 (2H, q, J 12.8, 6.4 Hz), 3.27 (1H, dd, J 14.1, 4.8 Hz), 3.11 (1H, dd, J 14.1, 9.5 Hz), 1.35 (3H, d, J 6.4 Hz), 1.31 (3H, d, J 6.4 Hz), m/z (ES$^+$, 70V) 484 (MH$^+$).

EXAMPLE 23

(S)-3-[4-(2,6-Naphthyridin-1-ylamino)phenyl]2-[2-(N-methyl-N-prolylamino)-3,4-dioxocyclobut-1-enylamino]propanoic acid δH (DMSO $d_6$, 350K), 9.20 (1H, s), 9.10 (1H, s), 8.65 (1H, d, J 5.85 Hz), 8.35 (1H, d, J 5.92 Hz), 8.14 (1H, d, J 5.68 Hz), 7.79 (2H, d, J 8.03 Hz), 7.36 (1H, d, J 9.0 Hz), 7.26–7.22 (3H, m), 5.16 (1H, br s), 3.50–3.39 (2H, m), 3.25 (1H, dd, J 14.09, 4.83 Hz), 3.17 (3H, s), 3.07 (1H, dd, J 14.1, 9.9 Hz), 1.61–1.52 (2H, m), 0.84 (3H, t, J 7.35 Hz); m/z (ES$^+$, 70V) 460(MH$^+$).

EXAMPLE 24

(S)-3-[4-(2,6-Naphthyridin-1-ylamino)phenyl]-2-[(2-(S)-(2-methoxymethyl)pyrrolidin-1-yl]-3,4-dioxocyclobut-1-enyl)amino]propanoic acid δH (DMSO $d_6$, 350K) 9.20 (1H, s), 9.10 (1H, s), 8.65 (1H, d, J 5.9 Hz), 8.35 (1H, d, J 5.9 Hz), 8.14 (1H, d, J 5.7 Hz), 7.80 (2H, d, J 8.3 Hz), 7.27–7.20 (4H, m), 5.07 (1H, br s), 4.20 (1H, d, J 5.2 Hz), 3.85–3.64 (2H, m), 3.35–3.32 (2H, m), 3.25 (3H, s), 3.25–3.01 (2H, m), 2.03–1.75 (4H, m); m/z (ES$^+$, 70V), 502 (MH$^+$).

EXAMPLE 25

(S)-3-[4-(2,6-Naphthyridin-1-ylamino)phenyl]-2-[2-(N-ethyl-N-iso-propylamino)-3,4-dioxocyclobut-1-enylamino]propanoic acid δH (DMSO $d_6$, 350K); 9.20 (1H, s), 9.09 (1H, s), 8.64 (1H, d, J 5.9 Hz), 8.35 (1H, d, J 5.9 Hz), 8.15 (1H, d, J 5.7 Hz), 7.78 (2H, d, J 8.3 Hz), 7.26–7.20 (4H, m), 5.18 (1H, brs), 4.44–4.37 (1H, m), 3,45 (2H, q, J 7.2, 2.4 Hz), 3.25 (1H, dd, J 14.1, 4.7 Hz), 3.08 (1H, dd, J 14.1, 9.8 Hz), 1.20 (6H, q, J 6.7, 3.3 Hz), 1.14 (3H, t, J 7.1 Hz), m/z (ES$^+$, 70V), 474 (MH$^+$).

EXAMPLE 26

(S)-3-[4-(2,6-Naphthyridin-1-ylamino)phenyl]-2-[2-(N-methyl-N-iso-propylamino)-3,4-dioxocyclobut-1-enylamino]propanoic acid δH (DMSO $d_6$, 350K) 9.20 (1H, s), 9.09 (1H, s), 8.65 (1H, d, J 5.9 Hz), 8.35 (1H, d, J 5.9 Hz), 8.14 (1H, d, J 5.6 Hz), 7.79 (2H, d, J 8.3 Hz), 7.38 (1H, d, J 8.1 Hz), 7.26–7.22 (3H, m), 5.12 (1H, br s), 4.46–4.40 (1H, m), 3.25 (1H, dd, J 14.1, 4.8 Hz), 3.05 (1H, dd, J 14.2, 4.6 Hz), 3.06 (3H, s), 1.82 (3H, d, J 2.58 Hz, 1.65 (3H, d, J 2.6 Hz); m/z (ES$^+$, 70V) 460 (MH$^+$).

EXAMPLE 27

(S)-3-[4-(2,6-Naphthyridin-1-ylamino)phenyl]-2-[2-(2,5-dimethylpyrrolidin-1-yl)-3,4-doxocyclobut-1-enylamino]propanoic acid δH (DMSO $d_6$, 350K) 9.20 (1H, d, J 0.9 Hz), 9.10 (1H, s), 8.65 (1H, d, J 5.9 Hz), 8.35 (1H, d, J 5.9 Hz), 8.14 (1H, d, J 5.7 Hz), 7.79 (2H, d, J 8.3 Hz), 7.26–7.23 (3H, m), 3.26 (1H, dd, J 14.2, 4.8 Hz), 3.1 (1H, dd, J 14.2, 9.7 Hz), 2.15–2.09 (2H, m), 1.73–1.66 (2H, m), 1.28 (3H, d, J 6.4 Hz), 1.25 (3H, d, J 6.4 Hz); m/z (ES$^+$, 70V) 486 (MH$^+$).

EXAMPLE 28

(S)-3-[4-(2,6-Naphthyridin-1-ylamino)phenyl]-2-[2-(2-methylpiperidin-1-yl)-3,4-dioxocyclobut-1-enylamino]propanoic acid δH (DMSO $d_6$, 370K), 9.19 (1H, s), 9.03 (1H, s), 8.64 (1H, d, J 5.8 Hz), 8.33 (1H, d, J 5.9 Hz), 8.14 (1H, d, J 5.6 Hz), 7.78 (2H, q, J 8.4, 2.3 Hz), 7.25–7.22 (4H, m), 5.13 (1H, br s), 4.45 (1H, br s), 4.04 (1H, d, J 13.7 Hz), 3.25–3.20 (2H, m), 3.11–3.05 (1H, m), 1.76–1.49 (6H, m), 1.24 (3H, q, J 6.9, 5.2 Hz); m/z (ES$^+$, 70V) 486 (MH$^+$).

EXAMPLE 29

Methyl(S)-3-[4-(2,6-naphthyridin-1-yloxy)phenyl]-2-(2-N,N-diethylamino-3,4-dioxocyclobut-1-enylamino)propanoate To methyl (S)-2-(2-isopropoxy-3,4-dioxocyclobut-1-enylamino)-3-[4-(2,6-naphthyridin-1-yloxy)phenyl]-propanoate (prepared from the compound of Intermediate 8 in a similar manner to the compound of Example 1) (0.20 g, 0.44 mmol) in methanol (3 ml) was added 2 equivalents of diethylamine (0.09 ml) and the solution was stirred at 65° overnight. The solution was cooled and then evaporated. The solid was chromatographed (silica, EtOAc/isohexane 50–100%) to afford the title compound (0.15 g, 73%) as a white solid. $δ_H$ (CDCl$_3$) 9.30 (1H, s), 8.77 (1H, d, J 5.7 Hz), 8.19 (1H, d, J 5.8 Hz), 8.08 (1H, d, J 5.79 Hz), 7.44 (1H, d, J 5.8 Hz), 7.24–7.18 (4H, m), 5.46 (1H,m), 5.35 (1H, m), 3.83 (3H, s), 3.70–3.40 (4H, br s), 3.31 (2H, d, J 5.3 Hz), 1.24 (6H, t, J 7.2 Hz). m/z (ES$^+$, 70V) MH$^+$ 475.

EXAMPLE 30

(S)-3-[4-(2,6-Naphthyridin-1-yloxy)phenyl]-2-(2-N,N-diethylamino-3,4-dioxocyclobut-1-enylamino)propanoic acid The compound of Example 29 (0.137 g, 0.29 mmol) in dioxan (2 ml) and water (2 ml) was treated with LiOH.H$_2$O (0.02 g) and stirred at RT for 4 h, a few drops of glacial acetic acid were added and the solution was then evaporated in vacuo. The product was chromatographed (silica; DCM 200: MeH 20: HOAc 3: H$_2$O 2) to afford the title compound as an off-white solid (0.10 g, 78%). $δ_H$ ($d_6$ DMSO, 350K), 9.40 (1H, s), 8.76 (1H, d, J 5.7 Hz), 8.15–8.09 (2H, m), 7.65 (1H, dd, J 5.8, 0.9 Hz), 7.37 (1H, s), 7.36 (2H, d, J 8.6 Hz), 7.20 (2H, d, J 8.6 Hz), 5.15 (1H, br s), 3.59–3.51 (4H, m), 3.32 (1H, dd, J 14.1, 4.8 Hz), 3.13 (1H, dd, J 14.1, 9.9 Hz), 1.14 (6H, t, J 7.1 Hz). m/z (ES$^+$, 70V) MH$^+$ 461.

The compounds of Examples 31 to 33 were prepared in a similar manner to the compounds of Examples 29 and 30.

EXAMPLE 31

(S)-3-[4-(2,6-Naphthyridin-1-yloxy)phenyl]-2-[2-2-piperidin-1-yl-3,4-dioxocyclobut-1-enylamino]propanoiac acid $δ_H$ ($d_6$ DMSO, 370K) 9.39 (1H, s), 8.76 (1H, d, J 5.7 Hz), 8.13 (2H, nr m), 7.65 (1H, dd, J 5.7, 0.9 Hz), 7.34 (2H, d, J 8.6 Hz), 7.21 (2H, d, J 8.6 Hz), 5.16 (1H, br s), 3.64–3.59 (5H, m), 3.31 (1H, dd, J 14.1, 5.0 Hz), 3.12 (1H, dd, J 14.1, 9.6 Hz), 1.63–1.57 (5H, m); m/z (ES$^+$, 70V) MH$^+$ 473.

EXAMPLE 32

Methyl-(S)-3-[4-(2,6-naphthyridin-1-yloxy)phenyl]-2-(2-N,N-di-n-propylamino-3,4-dioxocyclobut-1-enylamino)propanoic acid $\delta_H$ (d$_6$ DMSO) 9.41 (1H, s), 8.76 (1H, d, J 5.7 Hz), 8.14 (1H, d, J 5.7 Hz), 8.07 (1H, d, J 5.7 Hz), 7.74 (1H, d, J 8.9 Hz), 7.67 (1H, d, J 5.8 Hz), 7.33 (2H, d, J 8.5 Hz), 7.18 (2H, d, J 8.5 Hz), 5.23 (1H, m), 3.72 (3H, s), 3.37 (5H, br m), 3.11 (1H, m), 1.48 (4H, br m), 0.80 (6H, t, J 7.3 Hz).

EXAMPLE 33

(S)-3-[4-(2,6-Naphthyrydin-1-yloxy)phenyl]-2-(2-N,N-di-n-propylamino-3,4-dioxocyclobut-1-enylamino)propanoic acid $\delta_H$ (d$_6$ DMSO 350K) 9.41 (1, d, J 1.0 Hz), 8.77 (1H d, J 8.7 Hz), 8.14 (1H: d, J 5.7 Hz), 8.11 (1H, d, J 5.7 Hz), 7.67 (1H, dd, J 5.8, 0.9 Hz), 7.35 (2H, d, J 8.6 Hz), 7.27 (1H, d, J 8.9 Hz), 7.21 (2H, d, J 8.6 Hz), 5.20 (1H, m), 3,47 (4H, m), 3.33 (1H, dd, J 14.1, 4.8 Hz), 3.13 (1H, dd, J 14.1, 10.0 Hz), 1.55 (4H, m), 0.86 (6H, t, J 7.4 Hz). m/z (ES$^+$, 70V) 489 (MH$^+$).

EXAMPLE 34

Methyl-(S)-3-{4-[2-(2,6-dichlorophenyl)ethynyl]phenyl}-2-[(2-isopropoxy-3,4-dioxo-1-cyclobutenyl)amino]propanoate A mixture of the compound of Intermediate 34 (1.17 g, 3.04 mmol), 3,4-diisopropoxy-3-cyclobutene-1,2-diene (632 mg, 3.19 mmol) and DIPEA (540 μl, 3.1 mmol) in MeOH (30 ml) was stirred at RT for 3 days. The solvent was removed in vacuo. The residue was dissolved in DCM, washed with dil. HCl, dried (Na$_2$SO$_4$) and evaporated in vacuo. Column chromatography (SiO$_2$; MeOH/DCM, 3:97) gave the title compound as a yellow gum (1.45 g, 98%). δH (DMSO d$_6$, 390K), 8.47 (1H, d, J 7.9 Hz), 7.53–7.50 (3H, m), 7.38 (1H, dd, J 8.7, 7.5 Hz), 7.33 (2H, d, J 8.2 Hz), 5.21 (1H, sept. J 6.2 Hz), 4.78–4.72 (1H, m), 3.72 (3H, s), 3.31 (1H, dd, J 14.2, 5.2 Hz), 3.13 (1H, dd, J 14.2, 9.4 Hz), 1.38 (3H, d, J 6.1 Hz). 1.37 (3H, d, J 6.2 Hz); m/z (ES$^+$, 70V) 486 (M$^+$+H).

EXAMPLE 35

Methyl(S)-3-{4-[2-(2,6-dichlorophenyl)ethynyl]phenyl}-2-[2-propylamino-3,4-dioxocyclobut-1-enylamino]propanoate Propylamine (96 μl, 1.18 mmol) was added to a solution of the compound of Example 34 (475 mg, 0.98 mmol) in MeOH (10 ml). The reaction mixture was stirred at RT overnight. Volatiles were removed in vacuo and the resulting solid triturated with boiling MeOH. The solid was filtered off to give the title compound as a white solid (335 mg, 71%). δH (DMSO-d$_6$, 390K) 7.57–7.53 (4H, m), 7.44–7.40 (1H, m), 7.33 (2H, d, J 8.3 Hz), 7.3 (1H, br m) 7.2 (1H, br m), 5.10 (1H, m), 3.76 (3H, s), 3.54–3.49 (2H, m), 3.30 (1H, dd, J 14.1, 5.9 Hz), 3.18 (1H, dd, J 14.1, 7.7 Hz), 1.60 (2H, sept. J 7.1 Hz), 0.95 (3H, t, J 17.4 Hz); m/z (ES$^+$, 70V) 485 (M$^+$+H).

EXAMPLE 36

(S)-3-{4-[2-(2,6-Dichlorophenyl)ethynyl]phenyl}-2-(2-propylamino-3,4-dioxocyclobut-1-enylamino)propanoic acid Lithium hydroxide monohydrate (34 mg, 0.81 mmol) was added to the compound of Example 35 (325 mg, 0.671 mmol) in a mixture of THF (7 ml) and water (7 ml). After 1 h at RT the THF was removed in vacuo. The aqueous residue was acidified (pH 1–2, dil. HCl) and the precipitated filtered off, washed with water and dried to give the title compound as a yellow solid (315 mg, 90%). δH (DMSO d$_6$, 390K), 7.37–7.31 (4H, m), 7.21 (1H, dd, J 8.6, 7.5 Hz), 7.14 (2H, d, J 8.4 Hz), 7.1 (2H, br m), 4.82 (1H, m), 3.33–3.29 (2H, m), 3.11 (1H, dd, J 14.1, 5.7 Hz), 2.98 (1H, dd, J 14.1, 7.6 Hz), 1.39 (2H, sept. J 7.1 Hz). 0.75 (3H, t, J 7.4 Hz); m/z (ES$^+$, 70V) 471 (M$^+$+H).

EXAMPLE 37

Methyl (S)-3-{4-[2-(2,6-dichlorophenyl)ethynyl]phenyl}-2-(2-N,N-diethylamino-3,4-dioxocyclobut-1-enylamino)propanoate A mixture of the compound of Example 34 (470 mg, 0.969 mmol) and diethylamine (401 μl, 3.88 mmol) in MeOH (10 ml) was heated at 50° C. overnight. The solvent was removed in vacuo and the residue purified by column chromatography (SiO$_2$; MeOH/DCM, 5:95) to give the title compound as a light brown foam (450 mg, 93%). δH (DMSO d$_6$, 390K), 7.55–7.50 (4H, m), 7.42–7.35 (3H, m), 7.16 (1H, d, J 8.5 Hz), 5.63 (1H, m), 3.74 (3H, s), 3.55 (4H, q, J 7.1 Hz), 3.34 (1H, dd, J 14.2, 5.3 Hz), 3.20 (1H, dd, J 14.2, 9.4 Hz), 1.17 (6H, t, J 7.1 Hz); m/z (ES$^+$, 70V) 499 (M$^+$+H).

EXAMPLE 38

(S)-3-{4-[2-(2,6-Dichlorophenyl}ethynyl]phenyl}-2-(2-N,N-diethylamino-3,4-dioxocyclobut-1-enylamino)propanoic acid Obtained as an off-white solid from the compound of Example 37 by ester hydrolysis using the method described above for Example 36. δH (DMSO-d$_6$, 390K), 7.42–7.37 (4H, m), 7.29–7.24 (3H, m,), 6.91 (1H, br d, J 8.7 Hz), 3,43 (4H, q, J 7.1 Hz), 3.22 (1H, dd, J 14.2, 5.1 Hz), 3.06 (1H, dd, J 14.2, 9.4 Hz), 1.04 (6H, t J 7.1 Hz). m/z (ES$^+$, 70V) 485 (M$^+$+H).

The compounds of Examples 39 to 44 were prepared from methyl-(S)-3-(4-aminophenyl)-2-(N-t-butyloxycarbonylamino)propanoate and the appropriate reagent in a similar manner to that described for Intermediate 3 then derivatised in a manner analogous to that described for Examples 1, 2 and 3.

EXAMPLE 39

(S)-3-[4-(Benzylcarboxamido)phenyl]-2-(2-n-propylamino-3,4-dioxocyclobut-1-enylamino)propanoic acid $\delta_H$ (d$_6$ DMSO 390K); 9.25 (1H, s), 7.86 (1H, s), 7.44 (2H, d, J 8.4 Hz), 7.40–7.15 (5H, m), 7.08 (2H, d, J 8.4 Hz), 7.0 (1H, d, J 8.0 Hz), 4.94 (1H, br s), 3.62 (2H, s), 3,47 (2H, nr m), 3.14 (1H, dd, J 14.1, 5.7 Hz), 3.04 (1H, dd, J 14.1, 6.8 Hz), 1.57 (2H, dd, J 14.3, 7.1 Hz), 0.92 (3H, t, J 7.3 Hz); m/z (ES$^+$, 70V) 436 (MH$^+$).

EXAMPLE 40

(S)-3-[4-(2,4,6-Trifluorobenzylamino)phenyl]-2-(2-n-propylamino-3,4-dioxocyclobut-1-enylamino)propanoic acid $\delta_H$ (d$_6$ DMSO 390K) 7.88 (1H, s), 7.12 (1H, br s), 6.97 (1H, br s), 6.92 (2H, d, J 8.3 Hz), 6.78 (2H, nr m), 6.58 (2H, d, J 8.3 Hz), 4.89 (1H, br s)m 4.27 (2H, s), 3.46–3.48 (2H, nr m), 3.04 (1H, dd, J 14.18, 5.7 Hz), 2.95 (1H, dd, J 14.2, 6.68 Hz), 1.62–1.53 (2H, Nr m), 0.92 (3H, t, J 7.38 Hz); m/z (ES$^+$, 70V), 462 (MH$^+$).

EXAMPLE 41

(S)-3-[4-(2,6-Dichlorobenzylamino)phenyl]-2-(2-n-propylamino-3,4-dioxocyclobut-1enylamino) propanoic acid $\delta_H$ (d$_6$ DMSO) 7.26 (2H, s), 7.17 (1H, d, J 7.3 Hz), 7.14 (1H, br s), 6.95 (1H, br s), 6.8 (2H, d, J 8.4 Hz), 6.5 (2H, d, J 8.47 Hz), 4.70 (1H, br s), 4.31 (3H, s), 3.13 (2H, m), 2.89 (1H, dd, J 14.2, 5.6 Hz), 2.79 (1H, dd, J 14.2, 7.1 Hz), 2.85 (1H, br s), 1.44 (2H, dd, J 14.2, 7.1 Hz), 0.76 (3H, t, J 7.4 Hz); m/z (ES$^+$, 70V) 476 (MH$^+$).

EXAMPLE 42

(S)-3-[4-(2,4,6-Trichlorobenzylamino)phenyl]-2-(2-n-propylamino-3,4-dioxocyclobut-1-enylamino) propanoic acid $\delta_H$ (d$_6$ DMSO) 7.55 (2H, s),7.23 (1H, br s), 7.09 (1H, br d, J 8.4 Hz), 6.96 (2H, d, J 8.4 Hz), 6.66 (2H, d, J 8.5 Hz), 4.90 (1H, br s), 4.44 (2H, s), 3.48 (2H, m), 3.07 (1H, dd, J 14.1, 5.5 Hz), 2.95 (1H, dd, J 14.2, 7.2 Hz), 1.60 (2H, dd, J 14.3, 7.0 Hz), 0.93 (3H, t, J 7.4 Hz); m/z (ES$^+$, 70V) 509 (MH$^+$).

EXAMPLE 43

(S)-3-[4-(3-Chlorothiophen-2-ylcarboxamido) phenyl]-2-(2-n-propylamino-3,4-dioxocyclobut-1-enylamino)propanoic acid $\delta_H$ (d$_6$ DMSO) 9.50 (1H,s), 7.79 (1H, d, J 5.2 Hz), 7.57 (2H, d, J 8.4 Hz), 7.21 (2H, d, J 8.4 Hz), 7.12 (1H, br s), 7.11 (1H, d, J 5.2 Hz), 4.96 (1H, br s), 3,49 (2H, m), 3.25–3.02 (2H, m), 1.59 (2H, dd, J 14.3, 7.1 Hz), 0.93 (3H, t, J 7.4 HZ), m/z (ES$^+$, 70V) 461 (MH$^+$).

EXAMPLE 44

(S)-3-[4-(3-Chlorobenzo[b]thiophen-2-ylcarboxamido)phenyl]-2-(2-n-propylamino-3,4-dioxocyclobut-1-enylamino)propanoic acid $\delta_H$ (d$_6$ DMSO, 400K) 9.98 (1H, s), 8.07 (1H, nr, m), 7.94 (1H, nr m), 7.6 (5H, m), 7.23 (2H, d, J 8.4 Hz), 7.1 (1H, br s), 4.98 (1H, br s), 3.5 (2H, m), 2.35 (1H, dd, J 14.2, 5.7 Hz), 3.3 (1H, dd, J 14.2, 5.7 Hz), 1.59 (2H, hex, J 7.3 Hz), 0.94 (3H, t, J 7.3 Hz). m/z (ES$^+$, 70V) 512 (MH$^+$).

The compounds of Examples 45 to 47 were prepared from methyl (S)-3-(4-aminophenyl)-2-(N-t-butoxycarbonylamino)propanoate and the appropriate reagent in a similar manner to that described for Intermediate 6 then derivatised in a similar manner to that described for Examples 11, 13 and 14.

EXAMPLE 45

(S)-3-[4-(Pyrimidin-2-ylamino)phenyl]-2-(2-n-propylamino-3,4-dioxocyclobut-1-enylamino) propanoic acid $\delta_H$ ((d$_6$ DMSO, 390K) 8.86 (1H, br s), 8.41 (2H, d, J 4.8 Hz), 7.64 and 7.62 (2H, dd, J 1.8, 1.4 Hz), 7.15 (1H, br s), 7.12 (2H, d, J 8.6 Hz), 6.77 (1H, t, J 4.8 Hz), 4.93 (1H, br s), 3,48 (2H, t, J 6.8 Hz), 3.18 (1H, dd, J 14.1, 5.5 Hz), 3.05 (1H, dd, J 14.2, 7.3 Hz), 1.58 (2H, dd, J 14.2, 7.0 Hz), 0.92 (3H, t, J 7.4 Hz), m/z (ES$^+$, 70V) 396 (MH$^+$).

EXAMPLE 46

(S)-3-{4-[(2-Benzyl-6-chloropyrimidin-4-yl)amino] phenyl}-2-{[2-N,N-diethylamino-3,4-dioxocyclobut-1-enyl]amino}propanoic acid $\delta$H (DMSO, 370K) 9.40 (1H, s), 7.48 (2H, d J 2.3 Hz), 7.38 (4H, s), 7.35–7.25 (2H, m), 7.24 (2H, d, J 8.5 Hz), 6.64 (1H, s), 5.15 (1H, br s), 4.07 (2H, s), 3.60 (2H, q, J 7.2, 4.7 Hz), 3.3 0(1H, dd, J 14.2, 4.9 Hz), 3.10 (1H, dd, J 14.1, 9.4 Hz), 1.2 (6H, t, J 7.1 Hz); m/z (ES$^+$, 70V) 534 (MH$^+$).

EXAMPLE 47

(S)-3-[4-(Quinolin-4-ylamino)phenyl]-2-{[2-N,N-diethylamino-3,4-dioxo-1-cyclobutenyl] amino}propanoic acid $\delta$H (DMSO, 390K) 8.48 (1H, d, J 5.2 Hz), 8.39 (1H, d, J 7.1 Hz), 7.93 (1H, dd, J 8.4, 0.8 Hz), 7.71 (1H, d, J 5.4 Hz), 7.54–7.50 (1H, m), 7.32 (2H, d, J 8.4 Hz), 7.24 (2H, d, J 8.5 Hz), 6.83 (1H, d, J 5.2 Hz), 4.68 (1H, m), 3.70–3.50 (4H, m), 3.32 and 3.29 (1H, dd, J 13.8, 5.5 Hz), 3.24 and 3.21 (1H, dd, J 13.8, 6.3 Hz), 1.23 (6H, t, J 7.2 Hz), m/z (ES$^+$, 70V), 459 (MH$^+$).

The compounds of Examples 48 to 55 were prepared from N-BOC-L-tyrosine methyl ester and the appropriate reagent in the manner described for Intermediate 24 then derivatised in a manner analogous to that described for Examples 12 to 14.

EXAMPLE 48

Methyl (S)-3-[4-(2,6-Dichlorobenzyloxy)phenyl]-2-(2-N,N-diethylamino-3,4-dioxocyclobut-1-enylamino)propanoate $\delta$H (DMSO d$_6$) 7.71 (1H, d, J 9.0 Hz), 7.55–7.52 (2H, m), 7.47–7.42 (1H, d), 7.18 (2H, d, J 8.7 Hz), 6.95 (2H, d, J 8.7 Hz), 5.17 (2H, s), 5.15 (1H, m), 3.70 (3H, s), 3.55 (4H, br), 3.20 (1H, dd, J 4.6 Hz), 3.01–2.93 (1H, m), 1.07 (6H, t, J 7.1 Hz); m/z (ES$^+$, 70V) 505 (MH$^+$).

EXAMPLE 49

(S)-3-[4-(2,6-Dichlorobenzyloxy)phenyl]-2-(2-N,N-diethylamino-3,4-dioxocyclobut-1-enylamino) propanoic acid $\delta$H (DMSO d$_6$) 13.08 (1H, br), 8.31–8.24 (2H, m), 8.22–8.04 (1H, m), 8.02 (2H, d, J 8.8 Hz), 7.77 (2H, d, J 8.7 Hz), 6.07 (2H, s), 7.70 (1H, br), 5.95 (1H, br m), 4.49–4.40 (4H, m), 4.05 (1H, dd, J 14.3, 5.1 Hz), 3.89 (1H, dd, J 14.2, 9.1 Hz), 1.97 (6H, t, J 7.1 Hz); m/z (ES$^+$, 70V) 491 (MH$^+$).

EXAMPLE 50

Methyl (S)-3-[4-(2,6-dichlorobenzyloxy)phenyl]-2-(2-propylamino-3,4-dioxocyclobut-1-enylamino) propanoate $\delta$H (DMSO d$_6$) 7.60 (1H, br), 7.56 (2H, m), 7.47–7.42 (1H, m,), 7.09 (2H, d, J 8.3 Hz), 6.97 (2H, d, J 8.7 Hz), 5.17 (2H, s), 4.99 (1H, m), 3.70 (3H, s), 3.70 (2H, m), 3.12 (1H, dd, J 5.2 partly obscured), 1.54–1.47 (2H, m), 0.86 (3H, t, J 7.4 Hz). m/z (ES, 70V) 491 (MH$^+$).

EXAMPLE 51

(S)-3-[4-(2,6-Dichlorobenzyloxy)phenyl]-2-(2-propylamino-3,4-dioxocyclobut-1-enylamino) propanoic acid δH (DMSO d$_6$, 390K), 7.42–7.40 (2H, m), 7.35–7.31 (1H, m), 7.09 (1H, br), 7.08–7.06 (2H, m), 6.89–6.86 (2H, m) 5.17 (2H, s), 4.82 (1H, br), 3.39–3.38 (2H, m), 3.09 (1H, dd, J 14.2, 5.6 Hz), 2.96 (1H, dd, J 14.2, 7.4 Hz), 1.52–1.47 (2H, m), 0.84 (3H, t, J 7.4H$_3$); m/z (ES$^+$, 70V) 477 (MH$^+$).

EXAMPLE 52

Methyl (S)-3-[4-(2-pyrimidinyloxyphenyl]-2-(2-N,N-diethylamino-3,4-dioxocyclobut-1-enylamino) propanoate δH (DMSO d$_6$, 390K) 860 (2H, d, J 4.8 Hz), 7.31 (2H, d, J 8.6 Hz,), 7.20 (1Ha, t, J 4.8 Hz). 7.10 (2H, d, J 8.6 Hz), 5.28–5.23 (1H, m), 3.74 (3H, s), 3.56 (4H, q, J 7.1 Hz), 3.31 (1H, dd, J 14.3, 5.4 Hz), 3.17 (1H, dd, J 14.2, 9.2 Hz), 1.17 (6H, t, J 7.1 Hz); m/z (ES$^+$, 70V) 425 (MH$^+$).

EXAMPLE 53

(S)-3-[4-(2-Pyrimidinyloxy)phenyl]-2-(2-N,N-diethylamino-3,4-dioxocyclobut-1-enylamino) propanoic acid δH (DMSO d$_6$, 390K) 13.10 (1H, br), 8.60 (2H, d, J 4.8 Hz), 7.31 (2H, d, J 8.7 Hz), 7.20 (1H, d, J 4.8 Hz), 7.09 (2H, d, J 8.7 Hz), 6.97 (1H, br), 5.18–5.17 (1H, m), 3.60–3.59 (4H, m), 3.31 (1H, dd, J 14.3, 5.2 Hz), 3.16 (1H, dd, J 14.3, 9.1 Hz); m/z (ES$^+$, 70V), 411 (MH$^+$).

EXAMPLE 54

Methyl (S)-3-[4-(2-pyrimidinyloxy)phenyl]-2-(2-propylamino-3,4-dioxocyclobut-1-enylamino) propanoate δH (DMSO d$_6$, 390K) 8.61 (2H, d, J 4.8 Hz), 7.70 (1H, br), 7.55 (1H, br), 7.26–7.19 (3H, m), 7.10 (2H, d, J 8.5 Hz), 5.02 (1H, m), 3.71 (3H, s), 3.44 (2H, br), 3.18 (1H, dd, J 14.0, 5.4 Hz, CH$_A$H$_B$Ar), 3.08 (1H, dd, J 14.0, 8.0 Hz, CH$_A$H$_B$Ar), 1.54–1.46 (2H, m, NHCH$_2$CH$_2$CH$_3$), 0.86 (3H, t, J 7.4, NCH$_2$CH$_2$CH$_3$); m/z (ES$^+$, 70V) 411 (MH$^+$).

EXAMPLE 55

(S)-3-[4-(2-Pyrimidinyloxylphenyl]-2-(2-propylamino-3,4-dioxocyclobut-1-enylamino) propanoic acid δH (DMSO d$_6$, 390K) 8.67 (2H, d, J 4.8 Hz), 7.33 (2H, d, J 8.6 Hz), 7.27 (1H, d, J 4.7 Hz), 7.16 (2H, d, J 8.6 Hz), 5.06–5.02 (1H, m), 3.58–3.53 (2H, m), 3.31 (1H, dd, J 14.3, 5.6 Hz), 3.18 (1H, dd, J 14.2, 7.5 Hz,), 1.67–1.62 (2H, m), 0.99 (3H, t, J 7.4 Hz); m/z (ES$^+$, 70V) 397 (MH$^+$).

EXAMPLE 56

Methyl (S)-{4-[(3-phenyl-1-quinazolinyl)amino] phenyl}-[(2-isopropoxy-3,4-dioxocyclobut-1-enyl) amino]propanoate Intermediate 18 (518 mg, 1.3 mmol) was dissolved in MeOH (5 ml) and DIPEA base (0.5 ml), treated with 3,4-diisopropoxy-3-cyclobutene-1,2-dione (309 mg) and stirred at RT for 16 h. The solution was concentrated, dissolved in DCM (20 ml), washed with water, dried (Na$_2$SO4), filtered and concentrated. The crude product was purified by column chromatography (SiO$_2$:CH$_2$Cl$_2$/MeOH 50:1) to give the title compound (550 mg, 1.0 mmol, 79%) as a brown foamy solid. δH (DMSO) 8.44 (1H, m), 8.43 (2H, m), 7.80 (2H, m), 7.75 (2H, m), 7.50 (2H, m), 7.49 (2H, m), 7.33 (2H, d, J 8.6 Hz), 5.23 (1H, septet, J 6.2 Hz), 4.80 (1H, m), 3.76 (3H, s), 3.30 (1H, dd, 14.2, 5.3 Hz), 3.13 (1H, dd, J 14.2, 9.3 Hz), 1.38 (3H, d, J 6.2 Hz), 1.37 (3H, d, J 6.2 Hz); m/z (ESI, 70V) 537 (MH$^+$).

EXAMPLE 57

Methyl (S)-3-{4-[(2-phenyl-4-quinazolinyl)amino] phenyl}-[2-N,N-diethylamino-3,4-dioxo-1-cyclobutenyl)amino]propanoate The compound of Example 56 (550 mg, 1.0 mmol) and diethylamine (0.21 ml) in MeOH (5 ml) was stirred at RT for 16 h and the solution then concentrated. The residue was purified by column chromatography (SiO$_2$; DCM/MeOH 100:1) to give the title compound (375 mg, 0.68 mmol, 68%) as a brown foamy solid. δH (DMSO, 390K) 8.45 (3H, m), 7.85 (4H, m), 7.56 (1H, m), 7.48 (3H, m), 7.35 (2H, d, J 8.7H, 5.33 (1H, m), 3.76 (3H, s), 3.56 (2H, q, J 7.2 Hz), 3.54 (2H, q, J 7.2 Hz), 3.33 (1H, dd, J 14.2, 5.3 Hz), 3.20 (1H, dd, J 14.2, 9.2 Hz), 1.17 (6H, t, J 7.1 Hz); m/z; (ES$^+$, 70V) 550 (MH$^+$).

EXAMPLE 58

(S)-3-{4-[(2-Phenyl-4-quinazolinyl)amino]phenyl}-[2-N,N-diethylamino-3,4-dioxo-1-cyclobutenyl) amino]propanoic acid Example 57 (360 mg, 0.66 mol) was dissolved in THF (2 ml) and water (2 ml) and treated with lithium hydroxide (41 mg). The solution was stirred at RT or 90 mins and concentrated. The residue was dissolved in water and slowly acidified to pH2 with dilute hydrochloric acid to give a yellow precipitate which was filtered and dried to give the title compound (237 mg, 67%). δH (DMSO d$_6$) 9.75 (1H, br m), 8.60 (1H, d, J 8.7 Hz), 8.43 (2H, m), 7.92 (4H, m), 7.62 (1H, m), 7.52 (3H, m), 7.38 (2H, d, J 8.6 Hz), 5.21 (1H, m), 3.57 (2H, q, J 7.1 Hz), 3.55 (2H, q, J 7.1 Hz), 3.3 (1H, dd, J 14.1, 4.6 Hz), 3.15 (1H, dd, J 14.1, 10.1 Hz), 1.14 (3H, t, J 7.1 Hz); m/z (ES$^+$, 70V) 536 (MH$^+$).

The compounds of Examples 59 to 64 were prepared from methyl-(S)-3-(4-aminophenyl)-2-(N-t-butoxycarbonyl) aminopropanoate and the appropriate quinazoline in a manner similar to that described for Intermediate 18 and then derivatised in a manner similar to that described for Examples 56, 57 and 58.

EXAMPLE 59

Methyl-(S)-3-[4-(Quinazolin-4-ylamino)phenyl]-2-(2-N,N-diethylamino-3,4-dioxocyclobut-1-enylamino)propanoic acid δ$_H$ (CDCl$_3$) 8.73 (1H, s), 8.0 (1H, d, J 8.5 Hz), 7.91 (1H, d, J 8.3 Hz), 7.83–7.54 (6H, m), 7.15 (2H, d, J 8.5 Hz), 5.41 (1H, br s), 3.8 (3H, s), 3.70–3.35 (4H, br m), 3.35–3.15 (2H, m), 1.23 (6H, t, J 7.2 Hz); m/z (ES$^+$, 70V) 474 (MH$^+$).

EXAMPLE 60

(S)-3-[4-(Quinazolin-4-ylamino)phenyl]-2-(2-N,N-diethylamino-3,4-dioxocyclobut-1-enylamino) propanoic acid δ$_H$ (d$_6$ DMSO, 390K) 8.62 (1H, s), 8.55 (1H, d, J 8.8 Hz), 7.90–7.82 (5H, m), 7.66–7.62 (1H, nr m), 7.34 (2H, d, J 8.5

Hz), 7.09 (1H, br s), 5.25 (1H, br s), 3.64–3.56 (4H, m), 3.35 (1H, dd, J 14.2, 5.1 Hz), 3.20 (1H, dd, J 14.2, 9.1 Hz), 1.23 (6H, t, J 7.15 Hz); m/z (ES$^+$, 70V) 460 (MH$^+$).

EXAMPLE 61

(S)-3-{4-[(6,7-Dimethoxyquinazolin-4-yl)amino]phenyl}-2-{[2-N,N-diethylamino-3,4-dioxo-1-cyclobutenyl]amino}propanoic acid δH (CDCl$_3$) 9.39 (1H, s), 8.41 (1H, s), 7.81 (1H,s ), 7.67 (3H, dd, J 8.5, 3.8 Hz), 7.25 (2H, d, J 8.4 Hz), 7.16 (1H, s), 5.12 (1H, br s), 3.93 (3H, s), 3.91 (3H, s), 3.60–3.40 (4H, m), 3.20–2.90 (2H, m), 1.09 (6H, t, J 7.0 Hz); m/z (ES$^+$, 70V) 520 (MH$^+$).

EXAMPLE 62

(S)-3-{4-{(6,7-Dimethoxyquinazolin-4-yl)amino]phenyl}2-{[2-n-propylamino)-3,4-dioxo-1-cyclobutenyl]amino}propanoic acid δH (DMSO) 9.40 (1H, s), 8.42 (1H, s), 7.81 (1H, s), 7.70 (1H, s), 7.66 (2H, d, J 8.3 Hz), 7.16 (2H, d, J 7.9 Hz), 7.15 (1H, s), 4.82 (1H, br s), 3.93 (3H, s), 3.91 (3H, s), 3.6–2.9 (4H, m), 1.49 (2H, dd, J 14.1, 7.0 Hz), 0.86 (3H, t, J 7.3 Hz); m/z (ES$^+$, 70V) 506 (MH$^+$).

EXAMPLE 63

Methyl (S)-3-[4-(6-methoxyquinazolin-4-ylamino)phenyl]-2-(2-N,N-diethylamino-3,4-dioxocyclobut-1-enylamino)propanoate δ$_H$ (CDCl$_3$) 8.65 (1H, s), 7.83 (1H, d, J 9.1 Hz), 7.69 (3H, s, d, J 8.0 Hz), 7.45 (1H, dd, J 9.2, 2.6 Hz), 7.13 (2H, d, J 8.5 Hz), 5.40 (1H, br s), 3.95 (3H, s), 3.79 (3H, s), 3.6–3.41 (4H, br m), 3.48 (1H, dd, J 14.1, 5.5 Hz), 3.22 (1H, dd, J 14.1, 7.0 Hz), 1.29 (6H, t, J 7.2 Hz), m/z (ES$^+$, 70V) 504 (MH$^+$).

EXAMPLE 64

(S)-3-[4-(6-Methoxyquinazolin-4-ylamino)phenyl]-2-(2-N,N-diethylamino-3,4-dioxocyclobut-1-enylamino)propanoic acid δ$_H$ (d$_6$ DMSO, 370K); 9.35 (1H, br s), 8.40 (1H, s), 7.89 (1H, d, J 2.7 Hz, 7.54 (2H, d, J 8.6 Hz), 7.71 (1H, s), 7.49 (1H, d, J 2.7 Hz), 7.28 (2H, d, J 8.5 Hz), 7.15 (1H, br s), 5.14 (1H, br s), 3.97 (3H, s), 3.42–3.6 (4H, m), 3.28 (1H, dd, J 14.1, 4.9 Hz), 3.60–3.42 (4H, m), 3.28 (1H, dd, J 14.1, 4.9 Hz), 3.14 (1H, dd, J 14.1, 9.2 Hz), 1.16 (6H, t, J 17.1 Hz); m/z (ES$^+$, 70V) 490 (MH$^+$)

The compounds of Examples 65 to 68 were prepared from Intermediate 32 in a manner similar to that described for Examples 56 to 58.

EXAMPLE 65

Methyl 3-{4-[(6,7-dimethyoxy-4-quinazolinyl)amino]-3-methoxyphenyl}-2-(2-propylamino-3,4-dioxocyclobut-1-enylamino)propanoate δH (DMSO d$_6$, 390K) 8.54 (1H, br s), 8.38 (1H, s,), 7.75 (1H, d, J 7.8 Hz), 7.66 (1H, s), 7.34 (1H, br d J 8.5 Hz), 7.25 (1H, br s), 7.20 (1H, s), 6.97 (1H, d, J 1.9 Hz), 6.85 (1H, br s), 5.15–5.09 (1H, m), 3.97 (3H, s), 3.96 (3H, s), 3.78 (3H, s), 3.76 (3H, s), 3.5–3.47 (2H, m), 3.26 (1H, dd, J 14.1, 5.6 Hz), 3.12 (1H, dd, J 14.1, 8.0 Hz), 1.59 (2H, sext, J 7.2 Hz), 0.93 (3H, t, J 7.4 Hz); m/z (ES$^+$70V) 550 (MH$^+$).

EXAMPLE 66

3-{4-[(6,7-Dimethoxy-4-quinazolinyl)amino]-3-methoxyphenyl}2-(2-propylamino-3,4-dioxocyclobut-1-enylamino)propanoic acid δH (DMSO d$_6$, 390K) 8.38 (1H, s), 7.73 (1H, d, J 8.0 Hz), 7.66 (1H, s), 7.27 (1H, br s), 7.20 (1H, s), 6.99 (1H, d, J 1.8 Hz), 6.87 (1H, dd, J 8.0, 1.9 Hz), 5.02 (1H, m), 3.97 (3H, s), 3.96 (3H, s), 3.83 (3H, s), 3.49 (2H, q, J 6.3 Hz), 3.27 (1H, dd, J 14.1, 5.4 Hz), 3.11 (1H, dd, J 14.1, 7.8 Hz), 1.59 (2H, sext. J 76.2 Hz), 0.93 (3H, t, J 7.4 Hz); m/z (ES$^+$, 70V) 536 (MH$^+$.

EXAMPLE 67

Methyl 3-{4-[(6,7-dimethoxy-4-quinazolinyl)amino]-3-methoxyphenyl}-2-(2-N,N-diethylamino-3,4-dioxocyclobut-1-enylamino)propanoate δH (DMSO d$_6$, 390K) 8.33 (1H, br s), 8.15 (1H, s), 7.51 (1H, d, J 8.1 Hz), 7.44 (1H, s), 6.98 (1H, s), 6.92 (1H, d, J 9.0 Hz), 6.82 (1H, d, J 1. Hz), 6.69 (1H, dd, J 8.0, 1.9 Hz), 5.15–5.09 (1H, m), 3.76 (3H, s), 3.75 (3H, s), 3.61 (3H, s), 3.55 (3H, s), 3.35 (4H, q, J 7.1 Hz), 3.11 (1H, dd, J 14.2, 5.1 Hz), 2.94 (1H, dd, J 14.2, 9.5 Hz), 0.96 (6H, t, J 7.1 Hz); m/z (ES$^+$, 70V) 564 (MH$^+$).

EXAMPLE 68

3-{4-[(6,7-Dimethoxy-4-quinazolinyl)amino]-3-methoxyphenyl}-2-(2-N,N-diethylamino-3,4-dioxocyclobut-1-enylamino)propanoic acid δH (DMSO d$_6$, 390K), 8.49 (1H, s,), 7.97 (1H, br s), 7.51–7.49 (1H, m), 7.38 (1H, s), 7.21 (1H, br d), 7.12 (1H, s), 6.96 (1H, dd, J 7.9, 1.3 Hz), 5.28–5.25 (1H, m), 4.00 (6H, s), 3.81 (3H, s), 3.58 (1H, q, J 7.1 Hz), 3.35 (1H, dd, J 14.2, 4.8 Hz), 3.20 (1H, dd, , 14.2, 9.7 Hz), 1.18 (6H, t, J 7.1 Hz); m/z (ES$^+$, 70V) 550 (MH$^+$).

EXAMPLE 69

Methyl (S)-3-{4-[(6,7-dimethoxy-4-quinazolinyl)amino]phenyl}-2-(2-tert butyl-3,4-dioxocyclobut-1-enylamino)propanoate A mixture of methyl-(S)-{4-[(6,7-dimethoxy-4-quinazolinyl)amino]phenyl}-2-amino propanoate (332 mg, 0.869 mmol) and Intermediate 4 (171 mg, 0.87 mmol) in MeOH (10 ml) was heated at reflux for 5 days. The solvent was removed in vacuo. The residue was dissolved in DCM, washed with dil. HCl, dried (Na$_2$SO$_4$) and concentrated in vacuo. Column chromatography (SiO$_2$; MeOH/DCM, 7:93) gave the title compound as a brown glass (275 mg). δH (DMSO d$_6$) 9.39 (1H, s), 8.62 (1H, br d), 8.40 (1H, d, J 1.2 Hz), 7.81 (1h, s), 7.69–7.65 (2H, m), 7.22 (2H, d, J 8.5 Hz), 5.08 (1H, m), 3.94 (3H, s), 3.91 (3H, s), 3.74 (3H, s), 3.30 (1H, m), 3.02 (1H, dd, J 13.5, 11.2 Hz), 1.22 (9H, s); m/z (ES$^+$, 70V) 519 (MH$^+$).

EXAMPLE 70

Ethyl-(S)-3-{4-[(3-chloro-6,7-dimethoxy-4-quinazolinyl)amino]phenyl}-2-[(2-isopropoxy-3,4-dioxocyclobut-1-enyl)amino]propanoate Prepared in a similar manner to the compound of Example 56 from the Intermediate 45. δH (CD$_3$OD) 7.73 (2H, d, J 8.6 Hz), 7.73 (1H, s), 7.27 (2H, d, J 8.6 Hz), 7.06 (1H, s), 5.28

(1H, m), 5.07 and 4.62 (1H, br), 4.23 (2H, q), 4.00 (3H, s), 3.97 (3H, s), 3.35 (1H, m) 3.05 (1H, m), 1.40 (6H, d, J 6.2 Hz), 1.30 (3H, t, J 7.3 Hz).

EXAMPLE 71

Ethyl-(S)-3-{4-{(3-chloro-6,7-dimethoxy-4-quinazolinyl)amino]phenyl)-2-2-[(2-N,N-diethylamino-3,4-dioxocyclybut-1-enylamino] propanoate Prepared in a similar manner to the compound of the Example 57 from the compound of Example 70. δH (CD$_3$OD) 7.72 (1H, s), 7.70 (2H, d, J 8.6 Hz), 7.29 (2H, d, J 8.6 Hz), 7.04 (1H, s), 5.33 (1H, dd), 4.25 (2H, q, J 7.1 Hz), 3.99 (3H, s), 3.96 (3H, s), 3.58 (4H, br), 3.44 (1H, dd), 3.10 (1H, dd), 1.30 (3H, t, J 7.1 Hz), 1.20 (6H, t, J 7.2 Hz).

EXAMPLE 72

(S)-3-{4-[(3-Chloro-6,7-dimethoxy-4-quinazolinyl) amino]phenyl}-2-[(2-NN-diethylamino-cyclobut-1-enyl)amino]propanoic acid Prepared in a similar manner to the compound of Example 58 from the compound of Example 71. δH (d$_6$ DMSO) 7.86 (1H,s), 7.65 (2H, d, J 8.6 Hz), 7.31 (2H, d, J 8.6 Hz), 7.16 (1H, s), 5.15 (1H, m), 3.97 (3H, s), 3.95 (3H,s), 3.53 (4H, m), 3.20 (1H, m), 3.13 (1H, m), 1.50 (6H, t, J 7.1 Hz) m/z (ES$^+$) 554 (MH$^+$).

EXAMPLE 73

(S)-3-{4-[(6,7-Dimethoxy-4-quinazolinyl)amino] phenyl}-2-(2-t-butyl-3,4-dioxocyclobut-1-enylamino)propanoic acid Prepared in a similar manner to the compound of Example 58 from the compound of Example 69. δH (DMSO d$_6$, 370K) 8.40 (1H, s), 7.94 (1H, d, J 9.2 Hz), 7.83 (1H, s), 7.58 (2H, d, J 8.5 Hz), 7.17 (2H, d, J 8.6 Hz), 7.14 (1H, s), 4.96–4.90 (1H, m), 3.89 (3H, s), 3.87 (3H, s), 3.22 (1H, dd, J 14.1, 4.5 Hz), 3.04 (1H, dd, J 14.0, 10.2 Hz), 1.17 (9H, s) m/z (ES$^+$, 70V) 505 (MH $^+$).

EXAMPLE 74

Ethyl-(S)-3-(4-[(5-methyl-4-quinazolinyl)amino] phenyl)-2-[(2-isopropoxy-3,4-dioxocyclobut-1-enyl) amino]propanoate Intermediate 38 (800 mg, 2.3 mmol) and 3,4-diisopropoxy-3-cyclobuten-1,2-dione(453 mg, 1 equiv) were stirred at RT in anhydrous MeOH (5 m) for 17 h. The solvent was removed in vacuo and the residue purified by column chromatography (silica, 75:25 EtOAc-isohexane) to give the title compound. δH (DMSO d$_6$; 350K), 8.70 (broad signal), 8.50 (1H, s), 7.60 (4H, m), 7.30 (1H, d, J 7.0 Hz), 7.20 (2H, d, J 8.4 Hz), 5.20 (1H, m), 5.60 (1H, broad s), 4.20 (2H, m), 3.20 (1H, m), 3.10 (1H, m), 3.00 (3H, s), 1.30 (6H, d, J 6.2 Hz), 1.20 (3H, m); m/z (ES$^+$, 70V) 489 (MH$^+$).

EXAMPLE 75

Ethyl (S)-3-(4-[(5-methyl-4-quinazolinyl)amino] phenyl)-2-[(2-N,N-diethylamino-3,4-dioxocyclobut-1-enyl)amino]propanoate The compound of Example 74 (250 mg, 0.5 mmol) and N,N-diethylamine were stirred at RT in anhydrous (5 ml) MeOH for 17 h. The solvent was removed in vacuo and the residue purified by column chromatography (silica; EtOAc to 95% EtOAc: 5% MeOH) to isolate the title compound (200 mg) as an off-white solid. δH (DMSO d$_6$), 8.60 (1H, s), 8.50 (1H, s), 7.80 (1H, d, J 9.1 Hz), 7.60 (4H, m), 7.40 (1H, d, J 7.0 Hz), 7.20 (2H, d, J 6.8 Hz), 5.20 (1H, m), 4.00 (1H, m), 3.70 (3H, s), 3.50 (4H, broad signal), 3.20 (1H, m), 3.00 (1H, m), 2.90 (3H, s), 1.20 (6H, m). m/z (ES$^+$, 70V) 488 (MH$^+$).

EXAMPLE 76

(S)-3-(4-[(5-Methyl-4-quinazolinyl)amino]phenyl)-2-[(2-N,N-diethylamino-3,4-dioxocyclobut-1-enyl) amino]propanoic acid The compound of Example 75 (190 mg, 0.38 mmol) and lithium hydroxide monohydrate (19 mg) were stirred in a solvent mixture of MeOH (3 ml), THF (1.5 ml), and water (1.5 ml) for 17 h. The solvent was removed in vacuo and the residue dissolved in water, the solution neutralised with HCl, concentrated in vacuo and the residue purified by column chromatography (silica; 200:20:3:2 DCM:MeOH:AcOH:H$_2$O) to isolate the title compound as yellow solid. δH (DMSO d$_6$, 350K), 8.50 (1H, broad signal), 7.70 (3H, broad signal), 7.40–7.20 (3H, m), 5.10 (1H, m), 3.6 (4H, m), 3.30 (1H, m), 3.10 (1H, m), 1.10 (6H, t, J 7.2 Hz), m/z (ES$^+$, 70V) 474 (MH$^+$).

Also prepared in a similar manner to that described for Examples 75 and 76 from the compound of Example 74 were the compounds of Examples 77 and 78:

EXAMPLE 77

Methyl-(S)-3-(4-[(5-methyl-4-quinazolinyl)amino] phenyl)-2-[(2-N,N-di-n-propylamine-3,4-dioxocyclobut-1-enyl)amino]propanoate δH (DMSO d$_6$, 350K), 8.50 (1H, broad s), 7.80–7.60 (4H, m), 7.40 (1H, m), 7.30 (2H, m), 5.30 (1H, m), 3.70 (3H, s), 3.50 (4H, m), 3.40 (1H, m), 3.20 (1H, m), 3.10 (3H, s), 1.60 (4H, m), 0.90 (6H, t, J 7.4 Hz), m/z (ES$^+$, 70V) 516 (MH$^+$)

EXAMPLE 78

(S(-3-(4-[(5-Methyl-4-quinazolinyl)amino]phenyl)-2-[(2-N,N-di-n propylamino-3,4-dioxocyclobut-1-enyl)amino]propanoic acid δH (DMSO d$_6$, 350K), 8.70 (1H, s), 7.80 (2H, m), 7.70–7.40 (3H, m), 7.40 (2H, d, J 8.5 Hz), 5.20 (1H, m), 3.60 (4H, m), 3.40 (1H, m), 3.20 (1H, m), 3.00 (3H, s), 1.50 (4H, m), 0.90 (6H, t, J 7.3 Hz), m/z (ES$^+$, 70V) 502 (MH$^+$).

EXAMPLE 79

Ethyl-(S)-3-(4-([6-(trifluoromethoxy)-4-quinazolinyl]amino)phenyl]-2-[(2-isopropoxy-3,4-dioxocyclobut-1-enyl)amino]propanoate Prepared in a similar manner to Example 74 from the compound of Intermediate 43. δH (DMSO d$_6$, 300K), 9.20–9.00 (1H, m), 8.70 (2H, m), 8.00 (2H, m), 7.80 (2H, m), 7.30 (2H, m), 5.20 (1H, m), 5.00 (1H, m), 4.50 and 4.20 (1H, 2, sets m), 3.80 (3H, m), 3.30 (1H, m), 3.00 (1H, m), 1.30 (6H, m), m/z (ES$^+$, 70V) 545 (MH$^+$).

EXAMPLE 80

Methyl (S)-3-(4-([6-(trifluoromethoxy)-4-quinazolinyl]amino)phenyl)-2-[(2-N,N-diethylamino-3,4-dioxocyclbut-1-enyl)amino] propanoate Prepared from the compound of Example 79 in a similar manner to that described for Example 75. δH (CD$_3$OD), 8.50

(1H, s), 8.40 (1H, s), 7.90 (1H, d, J 9.1 Hz), 7.80 (1H, m), 7.70 (2H, d, J 8.6 Hz), 7.30 (2H, d, J 8.6 Hz), 5.50 (1H, m), 3.80 (3H, s), 3.60 (4H, broad signal), 3.50 (1H, m), 3.10 (1H, m), 1.20 (6H, t, J 7.2 Hz), m/z (ES$^+$, 70V) 544 (MH$^+$).

EXAMPLE 81

(S)-3-(4-([6-(Trifluoromethoxy)-4-quinazolinyl]amino)phenyl)-2-[(2-diethylamino-3,4-dioxocyclobut-1-enyl)amino]propanoic acid Prepared from Example 80 in a similar manner to that described for Example 76. δH (DMSO, 340K), 9.80 (bd s), 8.60 (2H, m), 8.00–7.70 (4H, m), 7.30 (2H, d), 5.20 (1H, m), 3.50 (4H, m), 3.30 (1H, m), 3.10 (1H, m), 1.20 (6H, t, J 7.1 Hz) m/z (ES$^+$, 70V) 544 (MH$^+$).

EXAMPLE 82

Methyl-(S)-3-(4-([6-(trifluoromethoxy)-4-quinazolinyl]amino)phenyl)-2-[(2-N,N-di-n-propylamino-3,4-dioxocyclobut-1-enyl)amino]propanoate Prepared from the compound of Example 79 in a similar manner to that described for Example 75. δH (CD$_3$OD), 8.50 (1H, s), 8.40 (1H, broad signal), 7.90 (1H, d, J 9.2 Hz), 7.85–7.70 (3H, m), 7.30 (1H, d, J 8.5 Hz), 5.40 (1H, m), 3.80 (3H, s), 3.60 (5H, broad signal), 3.10 (1H, m), 1.60 (4H, m), 0.90 (3H, t, J 7.4 Hz), m/z (ES$^+$, 70V) 586 (MH$^+$).

EXAMPLE 83

(S)-3-(4-([6-(Trifluoromethoxy)-4-quinazolinyl]amino)phenyl)-2-[(2-N,N-di-n-propylamino-3,4-dioxocyclobut-1-enyl)amino]propanoic acid Prepared from the compound of Example 82 in a similar manner to that described for Example 76. δH (DMSO d$_6$, 350K), 9.70 (broad signal), 8.60 (2H, m), 7.90 (1H, d, J 9.2 Hz), 7.70 (3H, m), 7.30 (2H, d, J 8.0 Hz), 5.20 (1H, m), 3.50 (4H, m), 3.30 (1H, m), 3.200 (1H, m), 1.60 (4H, m), 0.90 (3H, t, J 7.4 Hz), m/z (ES$^+$, 70V) 572 (MH$^+$).

The compounds of Examples 84 to 89 were prepared in a similar manner to that described for the preparation of Intermediate 8 from N-BOC-L-tyrosine methyl ester and the appropriate quinazoline and then derivatised in a manner similar to that described for Examples 56 to 58.

EXAMPLE 84

Methyl (S)-3-[4-(6,7-dimethoxyquinazolin-4-yloxy)phenyl]-2-(2-N,N-diethylamino-3,4-dioxocyclobut-1-enylamino)propanoate δH (CDCl$_3$) 8.57 (1H, s), 7.54 (1H, s), 7.33 (1H, s), 7.25–7.17 (5H, m), 5.55–4.9 (1H, m), 4.07 (6H, s), 3.83 (3H, s), 3.55–3.4 (5H, m), 3.31 (1H, dd, J 9.0, 5.5 Hz), 1.25 (6H, t, J 7.2 Hz), m/z (ES$^+$, 70V) 535 (MH$^+$).

EXAMPLE 85

(S)-3-{4-[(6,7-Dimethoxyquinazolin-4-yl)oxy]phenyl}-2-{[2-N,N-diethylamino-3,4-dioxo-1-cyclobutenyl]amino}propanoic acid δH (d$_6$ DMSO, 370K) 8.58 (1H, s), 7.64 (1H, s), 7.44–7.40 (3H, m), 7.28 (2H, d, J 8.5 Hz), 5.23 (1H, br s), 4.06 (3H, s), 4.04 (3H, s), 3.66–3.56 (4H, m), 3.39 (1H, dd, J 14.1, 4.6 Hz), 3.21 (1H, dd, J 14.1, 9.6 Hz), 1.22 (6H, t, J 7.1 Hz), m/z (ES$^+$, 70V) 521 (MH$^+$),

EXAMPLE 86

Methyl (S)-3-[4-(6-methoxyquinazolin-4-yloxy)phenyl]-2-(2-N,N-di-n-propylamino-3,4-dioxocyclobut-1-enylamino)propanoate δ$_H$ (CDCl$_3$) 8.62 (1H, s), 7.95 (2H, d, J 9.0 Hz), 7.59–7.54 (2H, m), 7.26–7.18 (3H, m), 5.47–5.42 (1H, m), 5.30 (1H, d, J 8.4 Hz), 3.99 (3H, s), 3.83 (3H, s), 3.60–3.10 (6H, m), 1.67–1.60 (4H, m), 0.92 (6H, t, J 7.4 Hz); m/z (ES$^+$, 70V) 533 (MH$^+$).

EXAMPLE 87

(S)-3-[4-(6-Methoxyquinazolin-4-yloxy)phenyl]-2-(2-N,N-di-n-propylamino-3,4-dioxocyclobut-1-enylamino)propanoic acid (d$_6$ DMSO) 8.57 (1H, s), 7.92 (1H, d, J 10.0 Hz), 7.65 (2H, d, J 7.3 Hz), 7.37 (2H, d, J 8.7 Hz), 7.24 (2H, d, J 8.6 Hz), 7.09 (1H, br s), 5.13 (1H, br s), 3.98 (3H, s), 3.59–3.39 (4H, m), 3.35 (1H, dd, J 14.5, 5.0 Hz), 3.17 (1H, dd, J 14.1, 9.4 Hz), 1.67–1.50 (4H, m), 0.87 (6H, t, J 7.3 Hz); m/z (ES$^+$, 70V) 519 (MH$^+$)

EXAMPLE 88

(S)-3-[4-(6-Methoxyquinazolin-4-yloxy)phenyl]-2-(2-n-prolylamino-3,4-dioxocyclobut-1-enylamino)propanoic acid δ$_H$ (d$_6$ DMSO, 370K) 8.59 (1H, s), 7.92 (1H, d, J 9.8 Hz), 7.65 (2H, d, J 7.3 Hz), 7.35–7.24 (5H, m), 4.97 (1H, br s), 3.99 (3H, s), 3.50 (2H, t, J 6.3 Hz), 3.29 (1H, dd, J 14.0, 5.4 Hz), 3.13 (1H, dd, J 14.1, 7.4 Hz), 1.58 (2H, dd, J 14.2, 7.1 Hz), 0.92 (3H, t, J 7.4 Hz); m/z (ES$^+$, 70V) 477 (MH$^+$).

EXAMPLE 89

(S)-3-[4-(6-Methoxyquinazolin-4-yloxy)phenyl]-2-(2-N,N-diethylamino-3,4-dioxocyclobut-1-enylamino)propanoic acid δ$_H$ (DMSO, 370K) 8.58 (1H, s), 7.92 (1H, d, J 9.9 Hz), 7.65 (2H, d, J 4.7 Hz), 7.39 (2H, d, J 8.5 Hz), 7.25 (2H, d, J 8.8 Hz), 5.21 (1H, br s), 3.98 (3H, s), 3.6–3.5 (4H, m), 3.34 (1H, dd, J 14.2, 5.1 Hz), 3.17 (1H, dd, J 14.1, 9.9 Hz), 1.17 (6H, t, J 7.1 Hz); m/z (ES$^+$, 70V) 461 (MH$^+$).

EXAMPLE 90

(S)-Ethyl-3-[4-(isoquinolin-1-ylamino)phenyl]-2-[(2-isopropoxy-3,4-dioxocyclobut-1-enyl)amino]propanoate A solution of Intermediate 10 (426 mg, 1.27 mmol) and 3,4-diisopropoxy-3-cyclobutene-1,2-dione(301 mg, 1.52 mmol) in absolute ethanol (5.0 ml) was stirred at 40° under N$_2$ for 18 h. The volatiles were removed in vacuo and the residue chromatographed (SiO$_2$; 25–50% EtOAc/hexane) to afford the title compound as a pale orange foam (585 mg, 97%). δH (CDCl$_3$) 8.04 (1H, d, J 5.8 Hz), 7.98 (1H, d, J 8.4 Hz), 7.72 (1H, d, J 7.8 Hz), 7.62 (1H, obscured m), 7.61 (2H, d, J 8.3 Hz), 7.52 (1H, app.t, J 7.0 Hz), 7.35 (1H, br s), 7.12–7.08 (3H, m), 6.60, 6.03, 5.13 and 4.59 (together 1H, m), 5.32 (1H, m), 4.24 (2H, q, J 7.1 Hz), 3.25–3.01 (2H, br m), 1.39 (6H, d, J 6.1 Hz), 1.30 (3H, t, J 7.1 Hz); m/z (ES$^+$, 70V) 474 (MH$^+$).

EXAMPLE 91

Ethyl (S)-3-[4-(isoquinolin-1-ylamino)phenyl]2-{[2-N,N-diethylamino-3,4-dioxo-1-cyclobutenyl]amino}propanoate A solution of the compound of Example 90 (585 mg, 1.24 mmol) and diethylamine (181 mg, 225 μl, 2.48 mmol) in absolute ethanol (2 ml) was heated at 50° under $N_2$ for 18 h. The volatiles were removed in vacuo affording the title compound as a dull orange foam (520 mg). δH (CDCl$_3$) 8.05 (1H, d, J 5.8 Hz), 7.96 (1H, d, J 8.3 Hz), 7.75 (1H, d, J 7.6 Hz), 7.65 (1H, m), 7.63 (2H, d, J 8.5 Hz), 7.55 (1H, app.t, J 7.0 Hz), 7.23 (1H, br s), 7.11 (1H, m), 7.10 (2H, d, J 8.5 Hz), 5.39 (1H, narrow m), 4.25 (2H, q, J 7.11 Hz), 3.65–3.35 (4H, br m), 1.32 (3H, t, J 7.1 Hz), 1.22 (6H, t, J 7.2 Hz); m/z (ES$^+$, 70V) 487 (MH$^+$).

EXAMPLE 92

(S)-3-[4-(Isoquinolin-1-ylamino)phenyl]-2-{[2-N,N-diethylamino-3,4-dioxo-1-cyclobutenyl] amino}propanoic acid A solution of example 91 (510 mg, 1.05 mmol) and LiOH.H$_2$O (53 mg, 126 mmol) in water (8 ml) and dioxan (8ml) was stirred at room temperature for 1.5 h. Several drops of AcOH were added and the volatiles were removed in vacuo. The residue was chromatographed [silica, DCM (200–120), MeOH (20), AcOH (3), H$_2$O(2)]. Freeze-drying from aqueous MeoH afforded the title compound as a pale yellow amphorous solid (230 mg, 48%). δH d$^6$ DMSO) 9.07 (1H, br s), 8.49 (1H, td, J 8.3 Hz), 7.95 (1H, d, J 5.7H), 7.79–7.75 (3H, m's), 7.70–7.64 (2H, m's), 7.58 (1H, td, J 8.3, 1.3 Hz), 7.20 (2H, d, J 8.4 Hz), 7.13 (1H, d, J 5.6 Hz), 3.65–3.38 (4H br m), 3.22 (1H, dd, J 13.9, 4.0 Hz), 2.99 (1H dd, J 13.9, 11.0 Hz) and 1.09 (6H, t, J 7.0 Hz); m/z (ES$^+$, 70V) 459 (MH$^+$).

EXAMPLE 93

Ethyl 3S)-3-{4-[(tert-Butoxycarbonyl)amino] phenyl}-3-[(2-isopropoxy-3,4-dioxocyclobut-1-enyl) amino]propanoate Intermediate 12 (190 mg, 0.062 mmol) in MeOH was treated with 3,4-diisopropoxy-3-cyclobutene-1,2-dione (122 mg) and N-methyl-morpholine (0.1 ml) and stirred at RT for 16 h. The solvent was removed and the product purified by column chromatography (SiO$_2$; CH$_2$Cl$_2$/MeOH 20:1) to give the title compound (176 mg, 64%) as a white foamy solid. δH (DMSO) 7.41 (2H, d, J 8.6 Hz), 7.24 (2h, d, J 8.6 Hz, 5.29 (1H, m), 5.25 (1H, dd, J 6.2 Hz), 4.06 (2H, q, J 7.1 Hz), 2.99 (1H, dd, J 15.8. 8.8 Hz), 2.86 (1H, dd, J 15.8, 6.0 Hz), 1.40 (3H, d, J 6.2 Hz), 1.36 (3H, d, J 6.2 Hz), 1.16 (3h, t, J 7.1 Hz); m/z (ESI, 70V) 469 (MNa$^+$).

EXAMPLE 94

Ethyl (3S)-3-(4-aminophenyl)-3-[(2-isopropoxy-3,4-dioxocyclobut-1-enyl)amino]propanoate The compound of Examples 93 (176 mg, 0.39 mmol) was dissolved in EtOAc (10 ml) and HCl gas was bubbled through. The reaction mixture was stirred for 2 h and the solvent removed to give the title compound (130 mg, 0.34 mmol, 87%) as an oil. δH (DMSO 360K) 7.38 (2H, d, J 8.5 Hz), 7.21 (2H, d, J 8.5 Hz), 5.30 (1H, br m), 5.25 (1H, septet, J 6.2 Hz), 4.08 (2H, q, J 7.1 Hz), 2.99 (1H, dd, J 15.8, 8.8 Hz), 2.85 (1H, dd, J 15.8, 6.0 Hz), 1.40 (3H, d, J 6.2 Hz), 1.36 (3H, d, J 6.2 Hz), 1.15 (3H, t, J 7.1 Hz).

EXAMPLE 95

Ethyl (3S)-3-{4-(3,5-dichloro-4-pyridylcarboxamido)phenyl}-3-[(2-isopropoxy-3,4-dioxocyclobut-1-enyl)amino]propanoate The compound of Example 94 (max 2 mmol) was dissolved in DCM (5 ml) and N-methylmorpholine (1 equiv) and cooled to 0°. 3,5-dichloroiso-nicotinoyl chloride (463 mg) was added and the reaction mixture stirred at RT for 16 h then quenched with sodium bicarbonate solution. The organic layer was washed with dilute hydrochloric acid, water, dried (Na$_2$SO$_4$), filtered and the solvent removed. The product was purified by column chromatography (SiO$_2$; CH$_2$Cl$_2$/MeOH 20:1) to give the title compound (636 mg, 61%) as an oil. δH (DMSO, 390K) 10.47 (1H, br s), 8.69 (2H, s), 7.62 (2H, d, J 8.4 Hz), 7.39 (2H, d, J 8.4 Hz), 5.38 (1H, m), 5.25 (1H, septet, J 6.1 Hz), 4.10 (2H, q, J 7.1 Hz), 3.05 (1H, dd, J 15.8, 8.6 Hz), 1.42 (3H, d, J 6.1 Hz), 1.38 (3H, d, J 6.1 Hz), 1.18 (3H, t, J 7.1 Hz); m/z (ES$^+$, 70V) 522 (MH$^+$).

EXAMPLE 96

Ethyl (3S)-3-{4-(3,5-dichloropyrid-4-ylcarboxamido)phenyl}-3-{[2-N,N-diethylamino-3, 4-dioxo-1-cyclobutenyl]amino}propanoate The compound of Example 95 (318 mg, 0.61 mmol) was dissolved in MeOH (5 ml) and diethylamine (0.13 ml). The solution was stirred for 16 h to give a white precipitate which was isolated by filtration and dried to give the title compound (247 mg, 78%) as a white solid. δH (DMSO, 370K) 10.93 (1H, br s), 8.78 (2H, s), 7.61 (2H, d, J 9.0 Hz), 7.41 (2H, d, J 9.0 Hz), 5.83 (1H, m), 3,59 (3H, s), 3,53 (4H, br m), 3.08 (1H, dd, J 16.0, 9.0 Hz), 2.95 (1H, dd, J 16.0, 6.0 Hz), 1.10 (6H, t, J 6.0 Hz); m/z (ES$^+$, 70V) 521 (MH+).

EXAMPLE 97

(3S)-3-{4-(3,5-Dichloropyrid-4-yl-carboxamido) phenyl}-3-{[2-N,N-diethylamino-3,4-dioxo-1-cyclobutenyl]amino}propanoic acid The compound of Example 96 (235 mg, 0.45 mmol) was dissolved in THF (5 ml) and water (5 ml) and lithium hydroxide (21 mg) added. The solution was stirred at RT for 3 h and the solvent removed in vacuo. The residue was dissolved in water (10 ml) and acidified to pH 2 with dil. HCl to give a white precipitate (198 mg, 0.39 mmol, 87%) which was filtered and dried to afford the title compound. δH (DMSO, 390K) 10.43 (1H, br s), 8.69 (2H, s), 7.60 (2H, d, J 8.5 Hz), 7.45 (2H, d, J 8.5 Hz), 7.29 (1H, br s), 5.82 (1H, m,), 3.60 (2H, q, J 7.0 Hz), 3,58 (2H, q, J 7.0 Hz), 3.02 (1H, dd, J 15.8, 8.2 Hz,), 2.90 (1H, dd, J 15.8, 6.1 Hz), 1.20 (6H, t, J 7.0 Hz); m/z (ES$^+$, 70V) 507 (MH$^+$). Analysis by chiral HPLC on Chirobiotic T column eluting with MeOH/ 0.6%HOAc gave single peak eluting at 5.58 minutes.

EXAMPLE 98

(3R)-3-{4-(3,5-Dichloropyrid-4-ylcarboxamido) phenyl-3-{[2-N,N-(diethylamino)-3,4-dioxo-1-cyclobutenyl]amino}propanoic acid This was prepared by the same route as the (S)-enantiomer Example 97 using the appropriate chiral amine. Analysis by chiral HPLC on Chirobiotic T column eluting with MeOH/0.6%HOAc gave single peak eluting at 6.54 minutes.

EXAMPLE 99

Methyl (3R)-3-[(2-Isopropoxy-3,4-dioxocyclobut-1-enyl)amino]-3-{4-[(6,7-dimethoxy-4-quinazolinyl) oxy]phenyl}propanoate Intermediate 16 (580 mg, 1.38 mmol) was dissolved in MeOH (6 ml) and DIPEA (0.53 ml) and 3,4-diisopropoxy- 3-cyclobuten-1,2-dione (300 mg) added. The solution was stirred for 16 h and the solvent removed. The residue was purified by column chromatography (SiO$_2$; CH$_2$Cl$_2$/MeOH 50:1) to give the title compound (539 mg, 75%) as a yellow oil. δH (DMSO, 350K) 8.99 (1H, br m), 8.54 (1H, s), 7.57 (1H, s), 7.49 (2H, d, J 8.6 Hz), 7.38 (1H, s), 7.32 (2H, d, J 8.6 Hz), 5.40 (1H, m), 5.27 (1H, septet, J 6.2 Hz), 4.01 (3H, s), 3.98 (3H, s), 3.64 (3H, s), 3.10 (1H, dd, J 16.1, 5.8 Hz,), 2.97 (1H, dd, J 16.1, 5.8 Hz), 1.42 (3H, d, J 6.2 Hz), 1.38 (3H, d, J 6.2 Hz); m/z (ES$^+$, 70V) 522 (MH$^+$).

EXAMPLE 100

Methyl (3R)-3-{[2-N,N-diethylamino-3,4-dioxo-1-cyclobutenyl]amino}-3-{4-[(6,7-dimethoxy-4-quinazolinyl)oxy]phenyl}propanoate The compound of Example 99 (265 mg, 0.51 mmol) was dissolved in MeOH (3 ml) and diethylamine added (0.1 ml). The solution was stirred for 16 h giving a white precipitate. The precipitate was filtered and dried to give the title compound (177 mg, 65%) as a white solid. δH (DMSO, 370K) 8.55 (1H, s), 7.59 (1H, s), 7.54 (2H, d, J 8.5 Hz), 7.32 (1H, s), 7.30 (2H, d, J 8.5 Hz, 5.94 (1H, m), 4.02 (3H, s), 3.99 (3H, s), 3.64 (3H, s), 3.60 (4H, septet, J 7.1 Hz), 3.15 (1H, dd, J 15.7, 8.9 Hz), 3.03 (1H, dd, J 15.7, 5.9 Hz), 1.19 (6H, t, J 7.1 Hz); m/z (ES$^+$, 70V) 535 (MH$^+$).

EXAMPLE 101

(R)-3-{[2-N,N-Diethylamino-3,4-dioxo-1-cyclobutenyl]amino}-3-{4-[(6,7-dimethoxy-4-quinazolinyl)oxy]phenyl}propanoic acid The compound of Example 100 (170 mg, 0.32 mmol) was dissolved in THF (2 ml) and water (2 ml) and lithium hydroxide (20 mg) was added. The solution was stirred at RT for 3 h and the solvent removed. The residue was dissolved in water (10 ml) and acidified to pH2 with dil. HCl to give a white precipitate (42 mg, 25%) which was filtered and dried. δH (DMSO, 400K) 8.56 (1H, s), 7.60 (1H, s), 7.54 (2H, d, J 8.6 Hz), 7.39 (1H, s), 7.31 (2H, d, J 8.6 Hz), 5.90 (1H, m), 4.03 (3H, s), 3.99 (3H, s), 3.62 (2H, q, J 7.1 Hz), 3.60 (2H, q, J 7.1 Hz), 3.06 (1H, dd, J 15.8, 8.2 Hz), 2.95 (1H, dd, J 15.8, 6.1 Hz), 1.21 (3H, t, 7.1 Hz), m/z (ES$^+$70V) 521 (MH$^+$).

EXAMPLE 102

Ethyl (R)-3-[(2-Isopropoxy-3,4-dioxo-1-cyclobutenyl)amino-3-[4-(2,6-naphthyridin-1-ylamino)phenylpropanoate Intermediate 23 (178 mg, 0.53 mmol) was dissolved in MeOH (5 ml) and DIPEA (0.2 ml), treated with 3,4-diisopropoxy-3-cyclobuten-1,2-dione (126 mg) and stirred at RT for 16 h. The solution was concentrated, dissolved in DCM (20 ml), washed with water, dried (Na$_2$SO4), filtered and concentrated. The crude product was purified by column chromatography (SiO$_2$, CH$_2$Cl$_2$/MeOH 50:1) to give the title compound (150 mg, 60%) as an oil. (H (DMSO, 370K) 9.21 (1H, s), 9.09 (1H, br s), 8.70 (1H, br m), 8.65 (1H, d, J 5.9), 8.33 (1H, d, J 5.9 Hz), 8.16 (1H, d, J 5.7 Hz), 7.87 (2H, d, J 8.5 Hz), 7.35 (2H, d, J 8.5 Hz), 7.28 (1H, d, J 5.7 Hz), 5.37 (1H, m), 5.27 (1H, septet, J 6.2 Hz), 4.10 (2H, qd, J 7.1, 0.4 Hz), 3.05 (1H, dd, J 15.8, 8.9Ht), 2.93 (1H, dd, J 15.8, 5.9), 1.43 (3H, d, J 6.$_2$ Hz), 1.39 (3H, d, J 6.2 H)), 1.18 (3H, t, 17.1 Hz),; m/z (ES$^+$, 70V) 475 (MH$^+$).

EXAMPLE 103

Methyl (3R)-3-](2-N,N-Diethylamino-3,4-dioxo-1-cyclobutenyl)amino-3-[4-(2,6-naphthyridin-1-ylamino)phenyl]propanoate The compound of Example 102 (145 mg, 0.3 mmol) in MeOH (2 ml) was treated with diethylamine (0.07 ml) and stirred at RT for 16 h. The solvent was removed and the residue was purified by column chromatography (SiO$_2$, CH$_2$Cl$_2$/MeOH 100.1) to give the title compound (140 mg, 98%) as a yellow oil. δH (DMSO, 370K) 9.21 (1H, s), 9.08 (1H, br s), 8.65 (1H, d, J 5.9 Hz), 8.33 (1H, d, J 5.9 Hz), 8.16 (1H, d, J 5.7 Hz), 7.86 (2H, d, J 8.5 Hz), 7.40 (2H, d, J 8.5 Hz), 7.27 (1H, d, J 5.7 Hz), 5.87 (1H, m), 3.63 (3H, s), 3.59 (2H, q, J 7.1 Hz), 3.57 (2H, q, J 7.1 Hz), 3.12 (1H, dd, J 15.6, 8.8 Hz), 2.99 (1H, dd, J 15.6, 6.0 Hz), 1.21 (3H, t, J 7.1 Hz), 1.18 (3H, t, J 7.1 Hz), m/z (ES$^+$, 70V) 474 (MH$^+$).

EXAMPLE 104

(3R)-3-[(2-N,N-Diethylamino-3,4-dioxo-1-cyclobutenyl)amino-3-[4-(2,6-naphthyridin-1-ylamino)phenylpropanoic acid The compound of Example 103 (140 mg, 0.29 mmol) was dissolved in THF (1 ml) and water (1 ml) and treated with lithium hydroxide (18 mg). The solution was stirred at RT for 90 mins and concentrated in vacuo. The residue was dissolved in water and slowly acidified to pH4.5 with dilute HCl acid to give a yellow precipitate which was filtered and dried to give the title compound (60 mg). δH (DMSO, 350K) 9.22 (1H, d, J 0.8 Hz), 8.66 (1H, d, J 5.8 Hz), 8.36 (1H, dd, J 5.9, 0.8 Hz), 8.15 (1H, d, J 5.8 Hz), 7.84 (2H, d, J 8.5 Hz), 7.40 (2H, d, J 8.5 Hz), 7.29 (1H, d, 15.8 Hz), 5.83 (1H, m), 3.59 (2H, q, J 7.1 Hz), 3.57 (2H, q, J 7.1 Hz), 3.02 (1H, dd, J 15.7, 8.8 Hz, 2.90 (1H, dd, J 15.7, 5.9 Hz), 1.18 (6H, t, J 7.1 Hz), m/z (ES$^+$, 70V) 460 (MH$^+$).

The following derivatised resins were prepared to enable the preparation of compounds of the invention by solid phase synthesis:

Resin bound (S)-3-(4-Aminophenyl)-2-(9-fluorenylmethoxy-carbonylamino)propanoic acid (1)

Paramax Wang resin (Advanced Chemtech, 10 g, 1.0 mmol/g, 10 mmol equivalent) in DMF (150 ml) was treated with N-α-FMOC-4-nitro-L-phenylalanine (22 g, 50 mmol), 2,6-dichlorobenzoyl chloride (7.0 ml, 50 mmol) and pyridine (4.0 ml, 50 mmol) and the mixture agitated under nitrogen at RT for 24 h. The resin was filtered and washed with DMF and DCM then unreacted resin sites were capped with 20% acetic anhydride in DMF for 30 mins at RT. The resin was filtered and washed as before then treated with a 1M solution of stannous chloride dihydrate in DMF (100 ml) at RT for 12 h and washed with DMF and DCM to give the derivatised resin (1).

Resin bound (S)-3-[4-(3,5-dichloro-4-pyridylcarboxamido) phenyl]-2-aminopropanoic acid (2)

Derivatised resin (1) from the above procedure was swollen in DCM (50 ml) then treated with DIPEA (5.1 ml, 29 mmol) and 3,5-dichloropyridine-4-carbonylchloride (6.2 ml, 29 mmol) and agitated under nitrogen at RT for 12 h. The resin was washed as before then treated with a 20% solution of piperidine in DMF (100 ml) for 30 mins at RT followed by thorough washing with DMC and DCM to give the derivatised resin (2).

Resin bound (S)-3-[4-(3,5-dichloro-4-pyridylcarboxamido) phenyl]-2-(2-methoxy-3,4-dioxocyclobut-1-enylamino) propanoic acid (3)

Derivatised resin (2) from the above procedure in DMF (100 ml) was treated with 3,4-dimethoxy-3-cyclobutene-1,2-dione (4.19, 29 mmol) for 12 h at 70° then filtered and washed with DMF and DCM to give the derivatised resin (3).

Resin bound (RS)-3-[4-(3,5-Dichloro-4-pyridylcarboxamido)phenyl]-3-(2-methoxy-3,4-dioxocyclobut-1-enylamino)propanoic acid (4)

Derivatised resin (4) was prepared in a similar manner to derivatised resin (3) from (RS)-3-(9-fluorenylmethoxycarbonylamino)-3-(4-nitrophenyl) propanoic acid. The latter was prepared as follows: A cold (0°) solution of (RS)-3-Amino-3-(4-nitrophenyl)propanoic acid [D. M. Kalvin and R. W. Woodward, J. Org. Chem. (1985) 50, 2259] (3.2 g, 15 mmol) in 10% aqueous sodium carbonate (60 ml) and 1,4-dioxane (30 ml) was treated portion-wise with 9-fluorenylmethoxycarbonyl-N-hydroxysuccinimide (5.6 g, 17 mmol) in 1,4-dioxane (15 ml) and the mixture stirred at RT for 12 h. The mixture was poured into water (300 ml) and the aqueous phase washed 3 times with $Et_2O$. The aqueous layer was then acidified with solid citric acid and extracted into $Et_2O$. The combined organic layers were dried ($MgSO_4$) and evaporated to a yellow oil then triturated from hexane and EtOAc to afford (RS)-3-(9-fluorenylmethoxy-carbonylamino)-3-(4-nitrophenyl)propanoic acid as a yellow solid (1.8 g); m/z ($ES^+$, 70V) 432.

Resin bound (S)-3-(4-Aminophenyl)-2-(2-propylamino-3,4-dioxocyclobut-1-enylamino)propanoic acid (5)

Paramax Wang resin (Advanced Chemtech, 10 g, 1.0 mmol/g, 10 mmol equivalent) in DMF (150 ml) was treated with N-α-FMOC-4-nitro-L-phenylalanine (22 g, 50 mmol), 2,6-dichlorobenzoyl chloride (7.0 ml, 50 mmol) and pyridine (4.0 ml, 50 mmol) and the mixture agitated under nitrogen at RT for 24 h. The resin was filtered and washed with DMF and DCM then unreacted resin sites were capped with 20% acetic anhydride in DMF for 30 mins at RT. The resin was filtered and washed as before. A portion (4 g) was treated with a 20% solution of piperidine in DMF (100 ml) for 30 mins at RT then filtered and washed with DMF and DCM. The resin was treated with 3,4-dimethoxy-3-cyclobutene-1,2-dione (1.9 g, 13.4 mmol) in DMF (50 ml) for 12 h at 70° C. then filtered and washed with DMF and DCM. The resin was swollen in DCM (10 ml) and EtOH (40 ml) and treated with propylamine (1.6 ml, 19.2 mmol). The solution was agitated for 12 h at RT then filtered and washed thoroughly with DCM. The resin was treated with a 1M solution of stannous chloride dihydrate in DMF (50 ml) at RT for 8 h then washed with DMF and DCM to give derivatised resin (5).

Resin bound diethylphosphono-α-diazoacetate (6)

Wang resin (Advanced Chem tech, 1.0 g, 0.7 mmol/g, 0.7 mmol equivalent) was treated with diethyl-phosphonoacetate (0.68 g, 3.5 mmol), N,N'-diisopropylcarbodiimide 0.55 ml, 3.5 mmol) and 4-N,N-dimethylaminopyridine (0.09 g, 0.7 mmol), in DCM (5.0 m). The mixture was agitated at ambient temperature for 16 h. The resin was filtered and washed with DMF, MeOH and DCM. The resulting resin (1.0 g) was treated with 4-acetamidobenzenesulfonyl azide (0.43 g, 1.86 mmol) and diazabicyclo-undec-7-ene (0.09 g, 0.62 mmol) in acetonitrile at ambient temperature for 16 h. The resin was washed with DMF, MeOH and DCM to give derivatised resin (6) [FTIR (ATR) $v_{max}$ 2132 $cm^{-1}$].

Resin bound (S)-3-[4-(1-isoquinolylamino)phenyl]-2-9-fluorenylmethoxycarbonylamino)propanoic acid (7)

Wang resin (Advanced Chemtech, 3.0 g, 0.7 mmol/g, 2.1 mmol equivalent) in DMF (50 ml) was treated with (S)-3-[4-(1-isoquinolylamino)phenyl]-2-(9-fluorenylmethoxycarbonylamino)propanoic acid (3.3 g, 6.3 mmol), 2,6-dichlorobenzoyl chloride (1.5 ml, 10.5 mmol) and pyridine (0.8 ml, 10.5 mmol) and the mixture agitated under nitrogen at RT for 24 h. The resin was filtered and washed with DMF and DCM then unreacted resin sites were capped with 20% acetic anhydride in DMF for 30 mins at RT. The resin was filtered and washed as before to give derivatised resin (7).

Resin bound (S)-3-[4-(1-isoquinolylamino)phenyl]-2-(2-methoxy-3,4-dioxocyclobut-1-enylamino)propanoic acid (8)

Derivatised resin (7) from the above procedure was treated with a 20% solution of piperidine in DMF (100 ml) for 30 mins at RT followed by thorough washing with DMF and DCM. The resin was treated with 3,4-dimethoxy-3-cyclobutene-1,2-dione (4.7 g, 33 mmol) for 12 h at 700 in DMF (50 ml) then filtered and washed as before to give derivatised resin (8).

Resin bound (S)-3-(4-benzoylphenyl)-2-(2-methoxy-3,4-dioxocyclobut-1-enyl)aminopropanoic acid (9)

N-α-FMOC-L-benzoylphenylalanine Wang resin (Advanced Chemtech, 400 mg, 0.5 mmol/g, 0.2 mmol equivalent) was treated with a 20% solution of piperidine in DMF (5 ml) for 30 mins at RT then filtered and washed thoroughly with DMF and DCM. The resin was treated with 3,4-dimethoxy-3-cyclobutene-1,2-dione (200 mg, 1.4 mmol) for 12 h at 70° in DMF (5 ml) then filtered and washed as before to give derivatised resin (9).

HPLC-MS

HPLC-MS was performed on a Hewlett Packard 1100/MSD ES Single Quadropole system with diode array detector using either:

Conditions A: A Luna C18(2) 50×4.6 mm (3 μm particle size) column, running a gradient of 95% [20 mM ammonium formate, pH 3.5], 5% [0.1% formic acid in acetonitrile] to 10% [20 mM ammonium formate, pH 3.5], 90% [0.1% formic acid in acetonitrile] over 3 min, then maintaining the mobile phase at that ratio for a further 2 min. Flow rate 0.8 ml/min.; or Conditions B: A Luna C18(2) 50×2.0 mm (3 μm) column, running a gradient of 95% [0.1% aqueous formic acid], 5% [0.1% formic acid in acetonitrile] to 10% [0.1% aqueous formic acid], 90% [0.1% formic acid in acetonitrile] over 2 min, then maintaining the mobile phase at that ratio for a further 1 min. Flow rate 0.8 ml/min.

MS was acquired by API electrospray in positive ion mode, at 70V, scanning from 150 to 750 amu.

EXAMPLE 105

(S)-3-[4-(3,5-Dichloro-4-pyridylcarboxamido) phenyl]-2(2-cyclohexylamino-3,4-dioxocyclobut-1-enylamino)propanoic acid To the derivatised resin (3), (120 mg) was added DCM (0.2 ml), EtOH (0.8 ml) and a 1M solution of cyclohexylamine in DCM (0.5 ml). The solution was agitated for 12 h at RT followed by filtration and multiple washes with DCM. The resin was treated with 60% trifluoroacetic acid in DCM (1.5 ml) for 3 h with agitation and then filtered. The filtrate was evaporated in vacuo to give the crude product which was purified by preparative HPLC to afford the title compound (5 mg).

HPLC-MS (Conditions A) Retention time 3.5 min $MH^+$ 531.

The following compounds of Examples 106 to 179 and 183 to 195 were prepared in a similar manner to the compound of Example 105, each using the starting material shown. For examples where the amine was added as a salt, 1 mol equivalent of DIPEA was also added.

EXAMPLE 106

(S)-3-[4-(3,5-Dichloro-4-pyridylcarboxamido)phenyl]-2-[2-(1-adamantylamino)-3,4-dioxocyclobut-1-enylamino]propanoic acid 1-Adamantylamine gave the title compound (4 mg).
HPLC-MS (Conditions A) Retention time 3.9 min MH$^+$ 583

EXAMPLE 107

(S)-3-[4-(3,5-Dichloro-4-2-pyridylcarboxamido)phenyl]-2-[2-(2-methoxyethylamino)-3,4-dioxocyclobut-1-enylamino]propanoic acid 2-Methoxyethylamine gave the title compound (10 mg).
HPLC-MS (Conditions A) Retention time 3.1 min MH$^+$ 507

EXAMPLE 108

(S)-3-[4-(3,5-Dichloro-4-pyridylcarboxamido)phenyl]-2-[2-(3-methoxypropylamino)-3,4-dioxocyclobut-1-enylamino]propanoic acid 3-Methoxypropylamine gave the title compound (9 mg).
HPLC-MS (Conditions A) Retention time 3.2 min MH$^+$ 521

EXAMPLE 109

(S)-3-[4-(3,5-Dichloro-4-pyridylcarboxamido)phenyl]-2-[2-(2-thienylmethylamino)-3,4-dioxocyclobut-1-enylamino]propanoic acid 2-(Aminomethyl)thiophene gave the title compound (4 mg).
HPLC-MS (Conditions A) Retention time 3.4 min MH$^+$ 545

EXAMPLE 110

(S)-3-[4-(3,5-Dichloro-4-pyridylcarboxamido)phenyl]-2-[2-(4morpholinoethylamino)-3,4-dioxocyclobut-1-enylamino]propanoic acid N-(2-Aminoethyl)morpholine gave the title compound (8 mg).
HPLC-MS (Conditions A) Retention time 2.9 min MH$^+$ 562

EXAMPLE 111

(S)-3-[4-(3,5-Dichloro-4-pyridylcarboxamido)phenyl]-2-[2-(3,4,5-trimethoxybenzylamino)-3,4-dioxocyclobut-1-enylamino]propanoic acid 3,4,5-Trimethoxybenzylamine gave the title compound (3 mg).
HPLC-MS (Conditions A) Retention time 3.4 min MH$^+$ 629

EXAMPLE 112

(S)-3-[4-(3,5-Dichloro-4-pyridylcarboxamido)phenyl]-2-[2-(1-piperidinoethylamino)-3,4-dioxocyclobut-1-enylamino]propanoic acid 1-(2-Aminoethyl)piperidine gave the title compound (11 mg).
HPLC-MS (Conditions A) Retention time 2.9 min MH$^+$ 560

EXAMPLE 113

(S)-3-[4-(3,5-Dichloro-4-pyridylcarboxamido)phenyl]-2-[2-(3-(2-oxopyrrolidin-1-yl)propylamino)-3,4-dioxocyclobut-1-enylamino]propanoic acid 1-(3-Aminopropyl)-2-pyrrolidinone gave the title compound (12 mg).
HPLC-MS (Conditions A) Retention time 3.1 min MH$^+$ 574

EXAMPLE 114

(S)-3-[4-(3,5-Dichloro-4-pyridylcarboxamido)phenyl]-2-[2-(3-phenylpropylamino)-3,4-dioxocyclobut-1-enylamino]propanoic acid 3-Phenylpropylamine gave the title compound (8 mg).
HPLC-MS (Conditions A) Retention time 3.7 min MH$^+$ 567

EXAMPLE 115

(S)-3-[4-(3,5-Dichloro-4-pyridylcarboxamido)phenyl-2-[2-(3-(1-imidazolyl)propylamino)-3,4-dioxocyclobut-1-enylamino]propanoic acid N-(3-Aminopropyl)imidazole gave the title compound (9 mg).
HPLC-MS (Conditions A) Retention time 2.8 min MH$^+$ 557

EXAMPLE 116

(S)-3-[4-(3,5-Dichloro-4-pyridylcarboxamido)phenyl]-2-[2-piperonylamino-3,4-dioxocyclobut-1-enylamino]propanoic acid Piperonylamine gave the title compound (3 mg).
HPLC-MS (Conditions A) Retention time 3.5 min MH$^+$ 583

EXAMPLE 117

(S)-3-[4-(3,5-Dichloro-4-pyridylcarboxamido)phenyl]-2-[2-(1-benzyl-4-piperidinylamino)-3,4-dioxocyclobut-1-enylamino]propanoic acid 4-Amino-1-benzylpiperidine gave the title compound (12 mg).
HPLC-MS (Conditions A) Retention time 3.1 min MH$^+$ 622

EXAMPLE 118

(S)-3-[4-(3,5-Dichloro-4-pyridylcarboxamido)phenyl]-2-[2-(2pyridylmethylamino)-3,4-dioxocyclobut-1-enylamino]propanoic acid 2-(Aminomethyl)pyridine gave the title compound (14 mg).
HPLC-MS (Conditions A) Retention time 3.2 min MH$^+$ 540

EXAMPLE 119

(S)-3-[4-(3,5-Dichloro-4-pyridylcarboxamido)phenyl]-2-(2-cyclopentylamino-3,4-dioxocyclobut-1-enylamino)propanoic acid Cyclopentylamine gave the title compound (8 mg).
HPLC-MS (Conditions A) Retention time 3.4 min MH$^+$ 517

EXAMPLE 120

(S)-3-[4-(3,5-Dichloro-4-pyridylcarboxamido)
phenyl]-2-[2-(4-phenylbutylamino)-3,4-
dioxocyclobut-1-enylamino]propanoic acid 4-Phenylbutylamine gave the title compound (4 mg).

HPLC-MS (Conditions A) Retention time 3.8 min $MH^+$ 581

EXAMPLE 121

(S)-3-[4-(3,5-Dichloro-4-pyridylcarboxamido)
phenyl]-2-[2-(3-pyridylmethylamino)-3,4-
dioxocyclobut-1-enylamino]propanoic acid 3-(Aminomethyl)pyridine gave the title compound (7 mg).

HPLC-MS (Conditions A) Retention time 3.0 min $MH^+$ 540

EXAMPLE 122

(S)-3-[4-(3,5-Dichloro-4-pyridylcarboxamido)
phenyl]-2-[2-(3,3-dimethylbutylamino)-3,4-
dioxocyclobut-1-enylamino]propanoic acid 3,3-Dimethylbutylamine gave the title compound (7 mg).

HPLC-MS (Conditions A) Retention time 3.6 min $MH^+$ 533

EXAMPLE 123

(S)-3-[4-(3,5-Dichloro-4-pyridylcarboxamido)
phenyl]-2-[2-(3,4-dichlorobenzylamino)-3,4-
dioxocyclobut-1-enylamino]propanoic acid 3,4-Dichlorobenzylamine gave the title compound (11 mg).

HPLC-MS (Conditions A) Retention time 3.8 min $MH^+$ 607

EXAMPLE 124

(S)-3-[4-(3,5-Dichloro-4-pyridylcarboxamido)
phenyl]-2-[2-(2-(1piperazinyl)ethylamino)-3,4-
dioxocyclobut-1-enylamino]propanoic acid N-(2-aminoethyl)piperazine gave the title compound (5 mg).

HPLC-MS (Conditions A) Retention time 2.8 min $MH^+$ 561

EXAMPLE 125

(S)-3-[4-(3,5-Dichloro-4-pyridylcarboxamido)
phenyl]-2-]2-(2-(1pyrrolidinyl)ethylamino)-3,4-
dioxocyclobut-1-enylamino]propanoic acid 1-(2-aminoethyl)pyrrolidine gave the title compound (9 mg).

HPLC-MS (Conditions A) Retention time 2.9 min $MH^+$ 546

EXAMPLE 126

(S)-3-[4-(3,5-Dichloro-4-pyridylcarboxamido)
phenyl]-2-[2-(3-hydroxypropylamino)-3,4-
dioxocyclobut-1-enylamino]propanoic acid 3-Hydroxypropylamine gave the title compound (4 mg).

HPLC-MS (Conditions A) Retention time 3.0 min $MH^+$ 507

EXAMPLE 127

(S)-3-[4-(3,5-Dichloro-4-pyridylcarboxamido)
phenyl]-2-[2-(3-cyclohexylanilino)-3,4-
dioxocyclobut-1-enylamino]propanoic acid 4-Cyclohexylaniline gave the title compound (3 mg).

HPLC-MS (Conditions A) Retention time 4.3 min $MH^+$ 607

EXAMPLE 128

(S)-3-[4-(3,5-Dichloro-4-2-pyridylcarboxamido)
phenyl]-2-[2-(4-morpholinoanilino)-3,4-
dioxocyclobut-1-enylamino]propanoic acid 4-Morpholinoaniline gave the title compound (5 mg).

HPLC-MS (Conditions A) Retention time 3.4 min $MH^+$ 610

EXAMPLE 129

(S)-3-[4-(3,5-Dichloro-4-pyridylcarboxamido)
phenyl]-2-(2-isopropylamino-3,4-dioxocyclobut-1-
enylamino)propanoic acid Isopropylamine gave the title compound (2 mg).

HPLC-MS (Conditions B) Retention time 2.3 min $MH^+$ 491

EXAMPLE 130

(S)-3-[4-(3,5-Dichloro-4-2-pyridylcarboxamido)
phenyl]-2-(2-tert-butylamino-3,4-dioxocyclobut-1-
enylamino)propanoic acid Tert-butylamine gave the title compound (1 mg).

HPLC-MS (Conditions B) Retention time 2.39 min $MH^+$ 505

EXAMPLE 131

(S)-3-[4-(3,5-Dichloro-4-pyridylcarboxamido)
phenyl]-2-2-propylamino-3,4-dioxocyclobut-1-
enylamino)propanoic acid Propylamine gave the title compound (5 mg).

HPLC-MS (Conditions B) Retention time 2.3 min $MH^+$ 491

EXAMPLE 132

(S)-3-[4-(3,5-Dichloro-4-pyridylcarboxamido)
phenyl]-2-(2-benzylamino-3,4-dioxocyclobut-1-
enylamino)propanoic acid Benzylamine gave the title compound (4 mg).

HPLC-MS (Conditions B) Retention time 2.43 min $MH^+$ 539

EXAMPLE 133

(S)-3-[4-(3,5-Dichloro-4-pyridylcarboxamido)
phenyl]-2-[2-(3-(dimethylamino)propylamino)-3,4-
dioxocyclobut-1-enylamino]propanoic acid 3-(Dimethylamino)propylamine gave the title compound (5 mg).
HPLC-MS (Conditions B) Retention time 1.92 min MH$^+$ 534

EXAMPLE 134

(S)-3-[4-(3,5-Dichloro-4-pyridylcarboxamido)
phenyl]-2-[2-(3-isopropoxyoropylamino)-3,4-
dioxocyclobut-1-enylamino]propanoic acid 3-Isopropoxypropylamine gave the title compound (5 mg).
HPLC-MS (Conditions B) Retention time 2.37 min MH$^+$ 549

EXAMPLE 135

(S)-3-[4-(3,5-Dichloro-4-pyridylcarboxamido)
phenyl]-2-[2-(3-ethoxypropylamino)-3,4-
dioxocyclobut-1-enylamino]propanoic acid 3-Ethoxypropylamine gave the title compound (5 mg).
HPLC-MS (Conditions B) Retention time 2.3 min MH$^+$ 535

EXAMPLE 136

(S)-3-[4-(3,5-Dichloro-4-pyridylcarboxamido)
phenyl]-2-[2-(2-(3-indolyl)ethylamino)-3,4-
dioxocyclobut-1-enylamino]propanoic acid 2-(3-indolyl)ethylamine gave the title compound (1 mg).
HPLC-MS (Conditions B) Retention time 2.15 min MH$^+$ 592

EXAMPLE 137

(S)-3-[4-(3,5-Dichloro-4-pyridylcarboxamido)
phenyl]-2-(2-cyclobutylamino-3,4-dioxocyclobut-1-
enylamino)propanoic acid Cyclobutylamine gave the title compound (4 mg).
HPLC-MS (Conditions B) Retention time 2.35 min MH$^+$ 503

EXAMPLE 138

(S)-3-[4-(3,5-Dichloro-4-2pyridylcarboxamido)
phenyl]-2-(2-cyclopropylamino-3,4-dioxocyclobut-
1-enylamino)propanoic acid Cyclopropylamine gave the title compound (5 mg).
HPLC-MS (Conditions B) Retention time 2.26 min MH$^+$ 489

EXAMPLE 139

(S)-3-[4-(3,5-Dichloro-4-pyridylcarboxamido)
phenyl]-2-[2-(4-(1,2,3-thiadiazol-4-yl)benzylamino)-
3,4-dioxocyclobut-1-enylamino]propanoic acid 4-(1,2,3-Thiadiazol-4-yl)benzylamine gave the title compound (5 mg).
HPLC-MS (Conditions B) Retention time 2.46 MH$^+$ 623

EXAMPLE 140

(S)-3-[4-(3,5-Dichloro-4-pyridylcarboxamido)
phenyl]-2-[2-(3-nitrobenzylamino)-3,4-
dioxocyclobut-1-enylamino]propanoic acid 3-Nitrobenzylamine hydrochloride gave the title compound (4 mg).
HPLC-MS (Conditions B) Retention time 2.46 min MH$^+$ 584

EXAMPLE 141

(S)-3-[4-(3,5-Dichloro-4-pyridylcarboxamido)
phenyl]-2-[2-(4-(methylsulfonyl)benzylamino)-3,4-
dioxocyclobut-1-enylamino]propanoic acid 4-(Methylsulfonyl)benzylamine hydrochloride gave the title compound (1 mg).
HPLC-MS (Conditions B) Retention time 2.31 min MH$^+$ 617

EXAMPLE 142

(S)-3-[4-(3,5-Dichloro-4-pyridylcarboxamido)phenyl]-2-
[2-(2-(benzylthio)ethylamino)-3,4-dioxocyclobut-1-
enylamino]propanoic acid 2-(Benzylthio)ethylamine hydrochloride gave the title compound (7 mg).
HPLC-MS (Conditions B) Retention time 2.56 min MH$^+$ 599

EXAMPLE 143

(S)-3-[4-(3,5-Dichloro-4-pyridylcarboxamido)
phenyl]-2-[2-(2-(4-nitrophenyl)ethylamino)-3,4-
dioxocyclobut-1-enylamino]propanoic acid 2-(4-Nitrophenyl)ethylamine hydrochloride gave the title compound (1 mg).
HPLC-MS (Conditions B) Retention time 2.47 min MH$^+$ 598

EXAMPLE 144

(S)-3-[4-(3,5-Dichloro-4-pyridylcarboxamido)
phenyl]-2-[2-(1-piperidinyl-3,4-dioxocyclobut-1-
enylamino]propanoic acid Piperidine gave the title compound (5 mg).
HPLC-MS (Conditions B) Retention time 2.36 min MH$^+$ 517

EXAMPLE 145

(S)-3-[4-(3,5-Dichloro-4-pyridylcarboxamido)
phenyl]-2-(2-morpholino-3,4-dioxocyclobut-1-
enylamino)propanoic acid Morpholine gave the title compound (7 mg).
HPLC-MS (Conditions B) Retention time 2.24 min MH$^+$ 519

EXAMPLE 146

(S)-3-[4-(3,5-Dichloro-4-pyridylcarboxamido)
phenyl]-2-(2-thiomorpholino-3,4-dioxocyclobut-1-
enylamino)propanoic acid Thiomorpholine gave the title compound (1 mg).
HPLC-MS (Conditions B) Retention time 2.36 min MH$^+$ 535

EXAMPLE 147

(S)-3-[4-(3,5-Dichloro-4-pyridylcarboxamido)
phenyl]-2-(2-diethylamino-3,4-dioxocyclobut-1-
enylamino)propanoic acid Diethylamine gave the title compound (4 mg).
HPLC-MS (Conditions B) Retention time 2.34 min MH$^+$ 505

EXAMPLE 148

(S)-3-[4-(3,5-Dichloro-4-pyridylcarboxamido)
phenyl]-2-[2-(1-pyrrolidinyl)-3,4-dioxocyclobut-1-
enylamino]propanoic acid Pyrrolidine gave the title compound (2 mg).
HPLC-MS (Conditions B) Retention time 2.29 min MH$^+$ 503

EXAMPLE 149

(S)-3-[4-(3,5-Dichloro-4-pyridylcarboxamido)
phenyl]-2-[2-(4-ethyl-1-piperazinyl)-3,4-
dioxocyclobut-1-enylamino]propanoic acid 1-Ethylpiperazine gave the title compound (6 mg).
HPLC-MS (Conditions B) Retention time 1.96 min MH$^+$ 546

EXAMPLE 150

(S)-3-[4-(3,5-Dichloro-4-pyridylcarboxamido)
phenyl]-2-[2-(4-(hydroxypropyl)-1-piperazinyl)-3,4-
dioxocyclobut-1-enylamino]propanoic acid 1-Piperazinepropanol gave the title compound (6 mg).
HPLC-MS (Conditions B) Retention time 1.94 min MH$^+$ 576

EXAMPLE 151

(S)-3-[4-(3,5-Dichloro-4-pyridylcarboxamido)
phenyl]-2-[2-((S)-3-dimethylamino-1-pyrrolidinyl)-
3,4-dioxocyclobut-1-enylamino]propanoic acid (S)-3-(Dimethylamino)pyrrolidine gave the title compound (8 mg).
HPLC-MS (Conditions B) Retention time 1.94 min MH$^+$ 546

EXAMPLE 152

(S)-3-[4-(3,5-Dichloro-4-pyridylcarboxamido)
phenyl]-2-[2-((S)-2-(methoxymethyl)-1-
pyrrolidinyl]-3,4-dioxocyclobut-1-enylamino]
propanoic acid (S)-2-(Methoxymethyl)pyrrolidine gave the title compound (2 mg).
HPLC-MS (Conditions B) Retention time 2.37 min MH$^+$ 547

EXAMPLE 153

(S)-3-[4-(3,5-Dichloro-4-2-pyridylcarboxamido)
phenyl]-2-[2-(1-piperazinyl)-3,4-dioxocyclobut-1-
enylamino]propanoic acid Piperazine gave the title compound (1 mg).
HPLC-MS (Conditions B) Retention time 1.93 min MH$^+$ 518

EXAMPLE 154

(S)-3-[4-(3,5-Dichloro-4-pyridylcarboxamido)
phenyl]-2-[2-((RS)-3-diethylamino-1-pyrrolidinyl)-
3,4-dioxocyclobut-1-enylamino]propanoic acid 3-(Diethylamino)pyrrolidine gave the title compound (6 mg).
HPLC-MS (Conditions B) Retention time 1.98 min MH$^+$ 574

EXAMPLE 155

(S)-3-[4-(3,5-Dichloro-4-pyridylcarboxamido)
phenyl]-2-[2-(4-(4-nitrophenyl)-1-piperazinyl)-3,4-
dioxocyclobut-1-enylamino]propanoic acid 1-(4-Nitrophenyl)piperazine gave the title compound (2 mg).
HPLC-MS (Conditions B) Retention time 2.54 min MH$^+$ 639

EXAMPLE 156

(S)-3-[4-(3,5-Dichloro-4-pyridylcarboxamido)
phenyl]-2-(2-butylamino-3,4-dioxocyclobut-1-
enylamino)propanoic acid Butylamine gave the title compound (3 mg).
HPLC-MS (Conditions B) Retention time 2.37 min MH$^+$ 505

EXAMPLE 157

(S)-3-[4-(3,5-Dichloro-4-pyridylcarboxamido)
phenyl]-2-(2-pentylamino-3,4-dioxocyclobut-1-
enylamino)propanoic acid Pentylamine gave the title compound (2 mg).
HPLC-MS (Conditions B) Retention time 2.44 min MH$^+$ 519

EXAMPLE 158

(S)-3-[4-(3,5-Dichloro-4-pyridylcarboxamido))
phenyl]-2-[2-((RS)-1-methylpropylamino)-3,4-
dioxocyclobut-1-enylamino]propanoic acid 1-Methylpropylamine gave the title compound (9 mg).
HPLC-MS (Conditions B) Retention time 2.34 min MH$^+$ 505

EXAMPLE 159

(S)-3-[4-(3,5-Dichloro-4-pyridylcarboxamido)
phenyl]-2-(2-isobutylamino)-3,4-dioxocyclobut-1-
enylamino]propanoic acid Isobutylamine gave the title compound (3 mg).
HPLC-MS (Conditions B) Retention time 2.35 min MH$^+$ 505

EXAMPLE 160

(S)-3-[4-(3,5-Dichloro-4-pyridylcarboxamido)
phenyl]-2-[2-(N-methyl-N-isopropylamino)-3,4-
dioxocyclobut-1-enylamino]propanoic acid Methylisopropylamine gave the title compound (4 mg).
HPLC-MS (Conditions B) Retention time 2.31 min MH$^+$ 505

EXAMPLE 161

(S)-3-[4-(3,5-Dichloro-4-pyridylcarboxamido)
phenyl]-2-[2-(N-ethyl-N-methylamino)-3,4-
dioxocyclobut-1-enylamino]propanoic acid N-Ethylmethylamine gave the title compound (6 mg).
HPLC-MS (Conditions B) Retention time 2.26 min $MH^+$ 491

EXAMPLE 162

(S)-3-[4-(3,5-Dichloro-4-pyridylcarboxamido)
phenyl]-2-[2-(N-methyl-N-propylamino)-3,4-
dioxocyclobut-1-enylamino]propanoic acid N-Methylpropylamine gave the title compound (3 mg).
HPLC-MS (Conditions B) Retention time 2.32 min $MH^+$ 505

EXAMPLE 163

(S)-3-[4-(3,5-Dichloro-4-pyridylcarboxamido)
phenyl]-2-(2-cyclopropanemethylamino-3,4-
dioxocyclobut-1-enylamino)propanoic acid Cyclopropanemethylamine gave the title compound (4 mg).
HPLC-MS (Conditions B) Retention time 2.32 min $MH^+$ 503

EXAMPLE 164

(S)-3-[4-(3,5-Dichloro-4-pyridylcarboxamido)
phenyl]-2-[2-(propynylamino)-3,4-dioxocyclobut-1-
enylamino]propanoic acid 2-Propynylamine gave the title compound (5 mg).
HPLC-MS (Conditions B) Retention time 2.26 min $MH^+$ 487

EXAMPLE 165

(S)-3-[4-(3,5-Dichloro-4-pyridylcarboxamido)
phenyl]-2-(2-isopentylamino-3,4-dioxocyclobut-1-
enylamino)propanoic acid 2-Isopentylamine gave the title compound (1 mg).
HPLC-MS (Conditions B) Retention time 2.44 min $MH^+$ 519

EXAMPLE 166

(S)-3-[4-(3,5-Dichloro-4-pyridylcarboxamido)
phenyl]-2-[2-((RS)-2-methylbutylamino)-3,4-
dioxocyclobut-1-enylamino]propanoic acid 2-Methylbutylamine gave the title compound (2 mg).
HPLC-MS (Conditions B) Retention time 2.42 min $MH^+$ 519

EXAMPLE 167

(S)-3-[4-(3,5-Dichloro-4-pyridylcarboxamido)
phenyl]-2-[2-((RS)-1,3-dimethylbutylamino)-3,4-
dioxocyclobut-1-enylamino]propanoic acid 1,3-Dimethylbutylamine gave the title compound (3 mg).
HPLC-MS (Conditions B) Retention time 2.49 min $MH^+$ 533

EXAMPLE 168

(S)-3-[4-(3,5-Dichloro-4-pyridylcarboxamido)
phenyl]-2-[2-(N-methyl-N-butylamino-3,4-
dioxocyclobut-1-enylamino]propanoic acid N-Methylbutylamine gave the title compound (3 mg).
HPLC-MS (Conditions B) Retention time 2.39 min $MH^+$ 519

EXAMPLE 169

(S)-3-[4-(3,5-Dichloro-4-2-pyridylcarboxamido)
phenyl]-2-[2-((RS)-1-methylbutylamino)-3,4-
dioxocyclobut-1-enylamino]propanic acid 1-Methylbutylamine gave the title compound (3 mg).
HPLC-MS (Conditions B) Retention time 2.41 min $MH^+$ 519

EXAMPLE 170

(S)-3-[4-(3,5-Dichloro-4-pyridylcarboxamido)
phenyl]-2-(2-allylamino-3,4-dioxocyclobut-1-
enylamino)propanoic acid Allylamine gave the title compound (3 mg).
HPLC-MS (Conditions B) Retention time 2.27 min $MH^+$ 489

EXAMPLE 171

(S)-3-[4-(3,5-Dichloro-4-pyridylcarboxamido)
phenyl]-2-[2-(2-(methylthio)ethylamino)-3,4-
dioxocyclobut-1-enylamino]propanoic acid 2-(Methylthio)ethylamine gave the title compound (3 mg).
HPLC-MS (Conditions B) Retention time 2.30 min $MH^+$ 523

EXAMPLE 172

(S)-3-[4-(3,5-Dichloro-4-pyridylcarboxamido)
phenyl]-2-(2-carboxyethylamino-3,4-dioxocyclobut-
1-enylamino)propanoic acid β-Alanine hydrochloride gave the title compound (4 mg).
HPLC-MS (Conditions B) Retention time 2.19 min $MH^+$ 521

EXAMPLE 173

(S)-3-[4-(3,5-Dichloro-4-pyridylcarboxamido)
phenyl]-2-[2-((S)-1-carboxy-3-methylbutylamino)-3,
4-dioxocyclobut-1-enylamino)propanoic acid L-Leucine hydrochloride gave the title compound 0.5 mg
HPLC-MS (Conditions B) Retention time 2.35 min $MH^+$ 563

EXAMPLE 174

(S)-3-[4-(3,5-Dichloro-4-pyridylcarboxamido)
phenyl]-2-(carboxymethylamino)-3,4-
dioxocyclobut-1-enylamino]propanoic acid Glycine hydrochloride gave the title compound (2 mg).
HPLC-MS (Conditions B) Retention time 2.19 min $MH^+$ 507

EXAMPLE 175

(S)-3-[4-(3,5-Dichloro-4-pyridylcarboxamido)phenyl]-2-[2-((S)-1-carboxy-2-methylpropylamino)-3,4-dioxocyclobut-1-enylamino]propanoic acid L-Valine hydrochloride gave the title compound (3 mg).
HPLC-MS (Conditions B) Retention time 2.28 min MH$^+$ 549

EXAMPLE 176

(S)-3-[4-(3,5-Dichloro-4-pyridylcarboxamido)phenyl]-2-[2-((S)-1-carboxy-2-phenylethylamino)-3,4-dioxocyclobut-1-enylamino]propanoic acid L-Phenylalanine gave the title compound (0.5 mg).
HPLC-MS (Conditions B) Retention time 2.38 min MH$^+$ 597

EXAMPLE 177

(S)-3-[4-(3,5-Dichloro-4-pyridylcarboxamido)phenyl]-2-(2-ethylamino-3,4-dioxocyclobut-1-enylamino)propanoic acid Ethylamine hydrochloride gave the title compound (3 mg).
HPLC-MS (Conditions B) Retention time 2.22 min MH$^+$ 477

EXAMPLE 178

(S)-3-[4-(3,5-Dichloro-4-pyridylcarboxamido)phenyl]-2-[2-methylamino-3,4-doxocyclobut-1-enylamino]propanoic acid Methylamine hydrochloride gave the title compound (2 mg).
HPLC-MS (Conditions B) Retention time 2.17 MH$^+$ 463

EXAMPLE 179

(S)-3-[4-(3,5-Dichloro-4-pyridylcarboxamido)phenyl]-2-(2-dimethylamino-3,4-dioxocyclobut-1-enylamino)propanoic acid Dimethylamine hydrochloride gave the title compound (6 mg).
HPLC-MS (Conditions B) Retention time 2.20 min MH$^+$ 477

EXAMPLE 180

(S)-3-[4-(3,5-Dichloro-4-pyridylcarboxamido)phenyl]-2-(2-anilino-3,4-dioxocyclobut-1-enylamino)propanoic acid Derivatised resin (2), (320 mg) in DMF (10 ml), was treated with 4-anilino-3-ethoxy-3-cyclobutene-1,2-dione (400 mg, 1.86 mmol) for 12 h at 70° then filtered and washed with DMF and DCM. The resin was treated with 60% trifluoroacetic acid in DCM (1.5 ml) for 3 h with agitation then filtered. The filtrate was evaporated in vacuo to give the crude product which was purified by preparative HPLC to afford the title compound (2 mg).
HPLC-MS (Conditions B) Retention time 2.46 min MH$^+$ 525

EXAMPLE 181

(S)-3-[4-(3,5-Dichloro-4-pyridylcarboxamido)phenyl]-2-(2-phenyl-3,4-dioxocyclobut-1-enylamino)propanoic acid By the same method as the compound of Example 180, 3-methoxy-4-phenyl-3-cyclobutene-1,2-dione was used to give the title compound (13 mg).
HPLC-MS (Conditions B) Retention time 2.53 min MH$^+$ 510

EXAMPLE 182

(S)-3-[4-(3,5-Dichloro-4-pyridylcarboxamido)phenyl]-2-(2-methoxy-3,4-dioxocyclobut-1-enylamino)propanoic acid Derivatised resin (3), (120 mg) was treated with 60% trifluoroacetic acid in DCM (1.5 ml) for 3 h with agitation then filtered. The filtrate was evaporated in vacuo to give the crude product which was purified by preparative HPLC to afford the title compound (2 mg).
HPLC-MS (Conditions B) Retention time 2.26 min MH$^+$ 465

EXAMPLE 183

(S)-3-[4-(3,5-Dichloro-4-pyridylcarboxamido)phenyl]-2-(2-(1-decahydroquinolyl)-3,4-dioxocyclobut-1-enylamino)propanoic acid Decahydroquinoline gave the title compound (1 mg).
HPLC-MS (Conditions B) Retention time 2.53 min MH$^+$ 571

EXAMPLE 184

(S)-3-[4-(3,5-Dichloro-4-pyridylcarboxamido)phenyl]-2-[2-(N-benzyl-N-butylamino)-3,4-dioxocyclobut-1-enylamino]propanoic acid N-Benzylbutylamine gave the title compound (5 mg).
HPLC-MS (Conditions B) Retention time 2.60 min MH$^+$ 595

EXAMPLE 185

(S)-3-[4-(3,5-Dichloro-4-pyridylcarboxamido)phenyl]-2-[2-(N-(2-cyanoethyl)-N-methylamino)-3,4-dioxocyclobut-1-enylamino]propanoic acid N-Methyl-beta-alanine nitrile gave the title compound (3 mg).
HPLC-MS (Conditions B) Retention time 2.22 min MH$^+$ 516

EXAMPLE 186

(S)-3-[4-(3,5-Dichloro-4-pyridylcarboxamido)phenyl]-2-[2-(N-(2-(2-pyridyl))ethyl)-N-methylamino)-3,4-dioxocyclobut-1-enylamino]propanoic acid 2-(2-Methylaminoethyl)pyridine gave the title compound (6 mg).
HPLC-MS (Conditions B) Retention time 2.03 min MH$^+$ 568.

EXAMPLE 187

(S)-3-[4-(3,5-Dichloro-4-pyridylcarboxamido)phenyl]-2-[2-(1,2,3,6-tetrahydro-1-pyridyl)-3,4-dioxocyclobut-1-enylamino]propanoic acid 1,2,3,6-Tetrahydropyridine gave the title compound (3 mg).
HPLC-MS (Conditions B) Retention time 2.32 min MH$^+$ 515

EXAMPLE 188

(S)-3-[4-(3,5-Dichloro-4-pyridylcarboxamido)phenyl]-2-[2-(N-methyl-N-(phenylethyl)amino)-3,4-dioxocyclobut-1-enylamino]propanoic acid N-Methylphenylethylamine gave the title compound (6 mg).
HPLC-MS (Conditions B) Retention time 2.45 min MH$^+$ 567

EXAMPLE 189

(S)-3-[4-(3,5-Dichloro-4-pyridylcarboxamido)phenyl]-2(2-(N,N-dibutylamino-3,4-dioxocyclobut-1-enylamino)propanoic acid Dibutylamine gave the title compound (5 mg).
HPLC-MS (Conditions B) Retention time 2.58 min MH$^+$ 561

EXAMPLE 190

(S)-3-[4-(3,5-Dichloro-4-pyridylcarboxamido)phenyl]-2-[2-(3,3,3-trifluoropropylamino)-3,4-dioxocyclobut-1-enylamino]propanoic acid 3,3,3-Trifluoropropylamine gave the title compound (7 mg).
HPLC-MS (Conditions B) Retention time 2.35 min MH$^+$ 545

EXAMPLE 191

(S)-3-[4-(3,5-Dichloro-4-pyridylcarboxamido)phenyl]-2-[2-(N-ethyl-N-(4-pyridylmethylamino)-3,4-dioxocyclobut-1-enylamino]propanoic acid 4-(Ethylaminomethyl)pyridine gave the title compound (4 mg).
HPLC-MS (Conditions B) Retention time 2.01 min MH$^+$ 568

EXAMPLE 192

(S)-3-[4-(3,5-Dichloro-4-pyridylcarboxamido)phenyl]-2-[2-(3-thiazolidinyl)-3,4-dioxocyclobut-1-enylamino]propanoic acid Thiazolidine gave the title compound (2 mg).
HPLC-MS (Conditions B) Retention time 2.29 min MH$^+$ 521

EXAMPLE 193

(S)-3-[4-(3,5-Dichloro-4-pyridylcarboxamido)phenyl]-2-[2-(N-allyl-N-methylamino)-3,4-dioxocyclobut-1-enylamino]propanoic acid N-Methylallylamine gave the title compound (4 mg).
HPLC-MS (Conditions B) Retention time 2.29 min MH$^+$ 503

EXAMPLE 194

(S)-3-[4-(3,5-Dichloro-4-pyridylcarboxamido)phenyl]-2-[2(N-benzyl-N-methylamino)-3,4-dioxocyclobut-1-enylamino]propanoic acid N-Benzylmethylamine gave the title compound (2 mg).
HPLC-MS (Conditions B) Retention time 2.42 min MH$^+$ 553

EXAMPLE 195

(S)-3-[4-(3,5-Dichloro-4-pyridylcarboxamido)phenyl]-2-(2-N,N-iallylamino-3,4-dioxocyclobut-1-enylamino)propanoic acid Diallylamine gave the title compound (5 mg).
HPLC-MS (Conditions B) Retention time 2.39 min MH$^+$ 529.

EXAMPLE 196

(S)-3-[4-(1-Isoquinolylamino)phenyl]-2-(2-N,N-diethylamino-3,4dioxocyclobut-1-enylamino)propanoic acid To the derivatised resin (8), (100 mg) was added ethanol (10 ml) and a 1M solution of diethylamine in DCM (0.7 ml). The solution was agitated for 18 h at RT then filtered and washed thoroughly with DCM. The resin was treated with 95% trifluoroacetic acid in DCM (2.0 ml) for 3 h with agitation and then filtered. The filtrate was evaporated in vacuo to give the crude product which was purified by preparative HPLC to afford the title compound (2 mg).
HPLC-MS (Conditions B) Retention time 2.0 min MH$^+$ 459.

The following compounds of Examples 197 to 237 were prepared in a similar manner to the compound of Example 196, each using the starting material shown. For examples where the amine was added as a salt, 1 mol equivalent of DIPEA was also added.

EXAMPLE 197

(S)-3-[4-(1-Isoquinolylamino)phenyl]-2-(2-(3-methoxypropylamino)-3,4-dioxocyclobut-1-enylamino)propanoic acid 3-Methoxypropylamine gave the title compound (4 mg).
HPLC-MS (Conditions B) Retention time 2.0 min MH$^+$ 475

EXAMPLE 198

(S)-3-[4-(1-Isoquinolylamino)phenyl]-2-[2-(1-piperidinyl)-3,4-dioxocyclobut-1-enylamino]propanoic acid Piperidine gave the title compound (2 mg).
HPLC-MS (Conditions B) Retention time 2.1 min MH$^+$ 471

EXAMPLE 199

(S)-3-[4-(1-Isoquinolylamino)phenyl]-2-[2-(1-piperazinyl)-3,4-dioxocyclobut-1-enylamino]propanoic acid Piperazine gave the title compound (2 mg).
HPLC-MS (Conditions B) Retention time 1.7 min MH$^+$ 472

EXAMPLE 200

(S)-3-[4-(1-Isoquinolylamino)phenyl]-2-(2-pentylamino-3,4-dioxocyclobut-1-enylamino)propanoic acid Pentylamine gave the title compound (3 mg).
HPLC-MS (Conditions B) Retention time 2.2 min MH$^+$ 473

EXAMPLE 201

(S)-3-[4-(1-Isoquinolylamino)phenyl]-2-(2-propylamino-3,4-dioxocyclobut-1-enylamino)propanoic acid Propylamine gave the title compound (1 mg).
HPLC-MS (Conditions B) Retention time 2.0 min MH$^+$ 445

EXAMPLE 202

(S)-3-[4-(1-Isoquinolylamino)phenyl]-2-(2-(1-decahydroquinolinyl)-3,4-dioxocyclobut-1-enylamino)propanoic acid Decahydroquinoline gave the title compound (5 mg).
HPLC-MS (Conditions B) Retention time 2.2 min MH$^+$ 525

EXAMPLE 203

(S)-3-[4-(1-Isoquinolylamino)phenyl]-2-{2-[N-ethyl-N-(4-pyridylmethyl)amino]-3,4-dioxocyclobut-1-enylamino}propanoic acid 4-(Ethylaminomethyl)pyridine gave the title compound (2 mg).
HPLC-MS (Conditions B) Retention time 1.8 min MH$^+$ 522

EXAMPLE 204

(S)-3-[4-(1-Isoquinolylamino)phenyl]-2-(2-tert-butylamino-3,4-dioxocyclobut-1-enylamino)propanoic acid Tert-Butylamine gave the title compound (1 mg).
HPLC-MS (Conditions B) Retention time 2.1 min MH$^+$ 459

EXAMPLE 205

(S)-3-[4-(1-Isoquinolylamino)phenyl]-2-(2-cyclobutylamino-3,4-dioxocyclobut-1-enylamino)propanoic acid Cyclobutylamine gave the title compound (1 mg).
HPLC-MS (Conditions B) Retention time 2.1 min MH$^+$ 457

EXAMPLE 206

(S)-3-[4-(1-Isoquinolylaminophenyl]-2-(2-thiomorpholino-3,4-dioxocyclobut-1-enylamino)propanoic acid Thiomorpholine gave the title compound (2 mg).
HPLC-MS (Conditions B) Retention time 2.1 min MH$^+$ 489

EXAMPLE 207

(S)-3-[4-(1-Isoquinolylamino)phenyl]-2-(2-allylamino-3,4-dioxocyclobut-1-enylamino)propanoic acid Allylamine gave the title compound (0.3 mg).
HPLC-MS (Conditions B) Retention time 2.0 min MH$^+$ 443

EXAMPLE 208

(S)-3-[4-(1-Isoquinolylamino)phenyl]-2-[2-(N-benzyl-N-methylamino)-3,4-dioxocyclobut-1-enylamino]propanoic acid N-Benzylmethylamine gave the title compound (5 mg).
HPLC-MS (Conditions B) Retention time 2.2 min MH$^+$ 507

EXAMPLE 209

(S)-3-[4-(1-Isoquinolylamino)phenyl]-2-(2-cyclohexylamino-3,4-dioxocyclobut-1-enylamino)propanoic acid Cyclohexylamine gave the title compound (3 mg).
HPLC-MS (Conditions B) Retention time 2.2 min MH$^+$ 485

EXAMPLE 210

(S)-3-[4-(1-Isoquinolylamino)phenyl]-2-(2-benzylamino-3,4-dioxocyclobut-1-enylamino)propanoic acid Benzylamine gave the title compound (2 mg).
HPLC-MS (Conditions B) Retention time 2.1 min MH$^+$ 493

EXAMPLE 211

(S)-3-[4-(1-Isoquinolylamino)phenyl]-2-{2-[3-(dimethylamino)propyl]amino-3,4-dioxocyclobut-1-enylamino}propanoic acid 3-(Dimethylamino)propylamine gave the title compound (2 mg).
HPLC-MS (Conditions B) Retention time 1.7 min MH$^+$ 488

EXAMPLE 212

(S)-3-[4-(1-Isoquinolylamino)phenyl]-2-[2-(2-pyridylmethyl)amino-3,4-dioxocyclobut-1-enylamino]propanoic acid 2-(Aminomethyl)pyridine gave the title compound (4 mg).
HPLC-MS (Conditions B) Retention time 1.9 min MH$^+$ 494

EXAMPLE 213

(S)-3-[4-(1-Isoquinolylamino)phenyl]-2-[2-(3-pyridylmethyl)amino-3,4-dioxocyclobut-1-enylamino]propanoic acid 3-(Aminomethyl)pyridine gave the title compound (1 mg).
HPLC-MS (Conditions B) Retention time 1.8 min MH$^+$ 494

EXAMPLE 214

(S)-3-[4-(1-Isoquinolylamino)phenyl]-2-[2-(4-pyridylmethyl)amino-3,4-dioxocyclobut-1-enylamino]propanoic acid 4-(Aminomethyl)pyridine gave the title compound (5 mg).
HPLC-MS (Conditions B) Retention time 1.8 min MH$^+$ 494

EXAMPLE 215

(S)-3-[4-(1-Isoquinolylamino)phenyl]-2-[2-(2-(benzylthio)ethylamino)-3,4-dioxocyclobut-1-enylamino]propanoic acid 2-(Benzylthio)ethylamine hydrochloride gave the title compound (4 mg).
HPLC-MS (Conditions B) Retention time 2.2 min MH$^+$ 553

EXAMPLE 216

(S)-3-[4-(1-Isoquinolylamino)phenyl]-2-(2-dimethylamino-3,4-dioxocyclobut-1-enylamino) propanoic acid Dimethylamine gave the title compound (24 mg).
HPLC-MS (Conditions B) Retention time 1.9 min $MH^+$ 431

EXAMPLE 217

(S)-3-[4-(1-Isoquinolylamino)phenyl]-2-(2-morpholino-3,4-dioxocyclobut-1-enylamino) propanoic acid Morpholine gave the title compound (3 mg).
HPLC-MS (Conditions B) Retention time 2.0 min $MH^+$ 473

EXAMPLE 218

(S)-3-[4-(1-Isoquinolylamino)phenyl]-2-[2-(N-methyl-N-butylamino)-3,4-dioxocyclobut-1-enylamino]propanoic acid N-Methylbutylamine gave the title compound (5 mg).
HPLC-MS (Conditions B) Retention time 2.2 min $MH^+$ 473

EXAMPLE 219

(S)-3-[4-(1-Isoquinolylamino)phenyl]-2-{2-[(RS)-2-methylbutylamino]-3,4-dioxocyclobut-1-enylamino}propanoic acid 2-Methylbutylamine gave the title compound (4 mg).
HPLC-MS (Conditions B) Retention time 2.2 min $MH^+$ 473

EXAMPLE 220

(S)-3-[4-(1-Isoquinolylamino)phenyl]-2-(2-butylamino-3,4-dioxocyclobut-1-enylamino) propanoic acid Butylamine gave the title compound (4 mg).
HPLC-MS (Conditions B) Retention time 2.2 min $MH^+$ 459

EXAMPLE 221

(S)-3-[4-(1-Isoquinolylamino)phenyl]-2-{2-[(RS)-1,3-dimethylbutylamino]-3,4-dioxocyclobut-1-enylamino}propanoic acid 1,3-Dimethylbutylamine gave the title compound (5 mg).
HPLC-MS (Conditions B) Retention time 2.3 min $MH^+$ 487

EXAMPLE 222

(S)-3-[4-(1-Isoquinolylamino)phenyl]-2-[2-(N-methyl-N-isopropylamino)-3,4-dioxocyclobut-1-enylamino]propanoic acid Methylisopropylamine gave the title compound (3 mg).
HPLC-MS (Conditions B) Retention time 2.1 min $MH^+$ 459

EXAMPLE 223

(S)-3-[4-(1-Isoquinolylamino)phenyl]-2-{2-[(RS)-1-methylbutylamino]-3,4-dioxocyclobut-1-enylamino}propanoic acid 1-Methylbutylamine gave the title compound (6 mg).
HPLC-MS (Conditions B) Retention time 2.2 min $MH^+$ 473

EXAMPLE 224

(S)-3-[4-(1-Isoquinolylamino)phenyl]-2-(2-isobutylamino-3,4-dioxocyclobut-1-enylamino) propanoic acid Isobutylamine gave the title compound (4 mg).
HPLC-MS (Conditions B) Retention time 2.1 min $MH^+$ 459

EXAMPLE 225

(S)-3-[4-(1-Isoquinolylamino)phenyl]-2-(2-dipropylamino-3,4-dioxocyclobut-1-enylamino) propanoic acid Dipropylamine gave the title compound (4 mg).
HPLC-MS (Conditions B) Retention time 2.2 min $MH^+$ 487

EXAMPLE 226

(S)-3-[4-(1-Isoquinolylamino)phenyl]-2-{2-[(RS)-2-methylpropylamino]-3,4-dioxocyclobut-1-enylamino}propanoic acid 1-Methylpropylamine gave the title compound (4 mg).
HPLC-MS (Conditions B) Retention time 2.1 min $MH^+$ 459

EXAMPLE 227

(S)-3-[4-(1-Isoquinolylaminophenyl]-2-[2-(N-ethyl-N-methylamino)--3,4-dioxocyclobut-1-enylamino] propanoic acid N-Ethylmethylamine gave the title compound (1 mg).
HPLC-MS (Conditions B) Retention time 2.0 min $MH^+$ 445

EXAMPLE 228

(S)-3-[4-(2,3,4-Trimethoxybenzylamino)phenyl]-2-(2-propylamino-3,4-dioxocyclobut-1-enylamino) propanoic acid To the derivatised resin (5), (120 mg) was added DCM (5 ml), DIPEA (0.1 ml, 0.6 mmol) and 2,3,4-trimethoxybenzoyl chloride (138 mg, 0.6 mmol). The solution was agitated for 12 h at RT then filtered and washed thoroughly with DCM. The resin was treated with 60% trifluoroacetic acid in DCM (1.5 ml) for 3 h with agitation and then filtered. The filtrate was evaporated in vacuo to give the crude product which was purified by preparative HPLC to afford the title compound (0.5 mg).
HPLC-MS (Conditions B) Retention time 2.34 min $MH^+$ 512

The following compounds of Examples 229 to 241 were prepared in a similar manner to the compound of Example 228, each using the starting material shown.

EXAMPLE 229

(S)-3-[4-(2,4-Dimethoxybenzoylamino)phenyl]-2-(2-propylamino-3,4-dioxocyclobut-1-enylamino) propanoic acid 2,4-Dimethoxybenzoylchloride gave the title compound (2 mg).
HPLC-MS (Conditions B) Retention time 2.41 min $MH^+$ 482

EXAMPLE 230

(S)-3-[4-(4-Bromobenzoylamino)phenyl]-2-(2-propylamino-3,4-dioxocyclobut-1-enylamino) propanoic acid 4-Bromobenzoylchloride gave the title compound (3 mg).
HPLC-MS (Conditions B) Retention time 2.49 min MH$^+$ 500

EXAMPLE 231

(S)-3-[4-(2-Thienylcarbonylamino)phenyl]-2-(2-propylamino-3,4-dioxocyclobut-1-enylamino) propanoic acid Thiophene-2-carbonylchloride gave the title compound (0.5 mg).
HPLC-MS (Conditions B) Retention time 2.31 min MH$^+$ 428

EXAMPLE 232

(S)-3-[4-(trans-Cinnamoylamino)phenyl]-2-(2-propylamino-3,4-dioxocyclobut-1-enylamino) propanoic acid trans-Cinnamoylchloride gave the title compound (1 mg).
HPLC-MS (Conditions B) Retention time 2.44 min MH$^+$ 448

EXAMPLE 233

(S)-3-[4-(Phenylacetylamino)phenyl]-2-(2-propylamino-3,4-dioxocyclobut-1-enylamino) propanoic acid Phenacetylchloride gave the title compound (0.5 mg).
HPLC-MS (Conditions B) Retention time 2.34 min MH$^+$ 436

EXAMPLE 234

(S)-3-[4-(2,6-Dichlorobenzoylamino)phenyl]-2-(2-propylamino-3,4-dioxocyclobut-1-enylamino) propanoic acid 2,6-Dichlorobenzoylchloride gave the title compound (3 mg).
HPLC-MS (Conditions B) Retention time 2.39 min MH$^+$ 490

EXAMPLE 235

(S)-3-[4-(2,6-Dimethylbenzoylamino)phenyl]-2-(2-propylamino-3,4-dioxocyclobut-1-enylamino) propanoic acid 2,6-Dimethylbenzoylchloride gave the title compound (1 mg).
HPLC-MS (Conditions B) Retention time 2.38 min MH$^+$ 450

EXAMPLE 236

(S)-3-[4-(Benzyloxyacetylamino)phenyl]-2-(2-propylamino-3,4-dioxocyclobut-1-enylamino) propanoic acid Benzyloxyacetylchloride gave the title compound (1 mg).
HPLC-MS (Conditions B) Retention time 2.41 min MH$^+$ 466

EXAMPLE 237

(S)-3-[4-(4-Cyanobenzoylamino)phenyl]-2-(2-propylamino-3,4-dioxocyclobut-1-enylamino) propanoic acid 4-Cyanobenzoylchloride gave the title compound (1 mg).
HPLC-MS (Conditions B) Retention time 2.33 min MH$^+$ 447

EXAMPLE 238

(S)-3-[4-(6-Chloro-3-pyridylcarboxamido)phenyl]-2-(2-propylamino-3,4-dioxocyclobut-1-enylamino) propanoic acid 6-Chloronicotinylchloride gave the title compound (1 mg).
HPLC-MS (Conditions B) Retention time 2.3 min MH$^+$ 457

EXAMPLE 239

(S)-3-[4-(2-Chloro-3-pyridylcarboxamido)phenyl]-2-(2-propylamino-3,4-dioxocyclobut-1-enylamino) propanoic acid 2-Chloronicotinylchloride gave the title compound (0.5 mg).
HPLC-MS (Conditions B) Retention time 2.18 min MH$^+$ 457

EXAMPLE 240

(S)-3-[4-(2-Fluorobenzoylamino)phenyl]-2-(2-propylamino-3,4-dioxocyclobut-1-enylamino) propanoic acid 2-Fluorobenzoylchloride gave the title compound (1 mg).
HPLC-MS (Conditions B) Retention time 2.33 min MH$^+$ 440

EXAMPLE 241

(S)-3-[4-(3,4-Dimethoxybenzoylamino)phenyl]-2-(2-propylamino-3,4-dioxocyclobut-1-enylamino) propanoic acid 3,4-Dimethoxybenzoylchloride gave the title compound (2 mg).
HPLC-MS (Conditions B) Retention time 2.28 min MH$^+$ 482

EXAMPLE 242

(S)-3-[4-(4-Methoxyphenoxycarbonylamino) phenyl]-2-(2-propylamino-3,4-dioxocyclobut-1-enylamino]propanoic acid To the derivatised resin (5), (120 mg) was added 1,4-dioxan (4.5 ml), DIPEA (0.2 ml, 1.2 mmol), water (0.5 ml) and 4-methoxyphenylchloroformate (0.2 ml, 0.6 mmol). The solution was agitated for 12 h at RT then filtered and washed thoroughly with DCM. The resin was treated with 60% trifluoroacetic acid in DCM (1.5 ml) for 3 h with agitation and then filtered. The filtrate was evaporated in vacuo to give the crude product which was purified by preparative HPLC to afford the title compound (2 mg).
HPLC-MS (Conditions B) Retention time 2.42 min MH$^+$ 468

The following compounds of Examples 243 to 246 were prepared in a similar manner to the compound of Example 242, each using the starting material shown.

EXAMPLE 243

(S)-3-[4-(4-Methylphenoxycarbonylamino)phenyl]-
2-(2-propylamino-3,4-dioxocyclobut-1-enylamino)
propanoic acid p-Tolylchloroformate gave the title compound (0.5 mg).

HPLC-MS (Conditions B) Retention time 2.50 min MH$^+$ 452

EXAMPLE 244

(S)-3-[4-(4-Fluorophenoxycarbonylamino)phenyl]-
2-(2-propylamino-3,4-dioxocyclobut-1-enylamino)
propanoic acid 4-Fluorophenylchloroformate gave the title compound (2 mg).

HPLC-MS (Conditions B) Retention time 2.45 min MH$^+$ 456

EXAMPLE 245

(S)-3-[4-(Phenoxycarbonylamino)phenyl]-2-(2-(2-propylamino-3,4-dioxocyclobut-1-enylamino)
propanoic acid Phenylchloroformate gave the title compound (2 mg).

HPLC-MS (Conditions B) Retention time 2.42 min MH$^+$ 438

EXAMPLE 246

(S)-3-[4-(4-Nitrobenzyloxycarbonylamino)phenyl]-
2-(2-propylamino-3,4-dioxocyclobut-1-enylamino)
propanoic acid 4-Nitrobenzylchloroformate gave the title compound (1 mg).

HPLC-MS (Conditions B) Retention time 2.47 min MH$^+$ 497

EXAMPLE 247

(S)-3-(4-Benzoylphenyl)-2-(2-propylamino-3,4-dioxocyclobut-1-enylamino)propanoic acid To the derivatised resin (9), (200 mg) was added ethanol (1.6 ml), DCM (0.4 ml) and propylamine (0.08 ml, 1 mmol). The solution was agitated for 12 h at RT then filtered and washed thoroughly with DCM. The resin was treated with 95% trifluoroacetic acid in DCM (2.0 ml) for 3 h with agitation and then filtered. The filtrate was evaporated in vacuo to give the crude product which was purified by preparative HPLC to afford the title compound (4 mg).

HPLC-MS (Conditions B) Retention time 2.4 min MH$^+$ 407.

The following compound of Example 248 was prepared in a similar manner to the compound of Example 247 using the starting material shown.

EXAMPLE 248

(S)-3-(4-Benzoylphenyl)-2(2-morpholino-3,4-dioxocyclobut-1-enylamino)propanoic acid Morpholine gave the title compound (5 mg).

HPLC-MS (Conditions B) Retention time 2.3 min MH$^+$ 435

EXAMPLE 249

(S)-3-[4-(1-Isoquinolylcarboxamido)phenyl]-2-(2-propylamino-3,4dioxocyclobut-1-enylamino)
propanoic acid A slurry of derivatised resin (5) (prepared from Wang resin (0.7 mmol/g), 100 mg) in DCM (5 ml) was treated with 1-isoquinoline carboxylic acid (56 mg, 0.30 mmol), DIEA (45 µl, 0.25 mmol) and [O-(7-azabenzotriazol-1-yl)-1,1,3,3-Tetramethyluronium-hexafluorophosphate] (HATU) (95 mg, 0.25 mmol). The mixture was agitated for 16 h at RT then filtered and washed thoroughly with DCM, DMF, MeOH, DMF then DCM. The resin was treated with 50% trifluoroacetic acid in DCM (5 ml) for 3 h with aggitation and then filtered. The resin was washed with a further portion of DCM (5 ml). The combined filtrate was evaporated in vacuo to give the crude product which was purified by preparative HPLC to afford the title compound (7.3 mg).

HPLC-MS (Conditions B). Retention time 2.47 min, MH$^+$ 473

The following compounds of Examples 250 to 281 were prepared in a similar manner to the compound of Example 249, each using the starting material shown.

EXAMPLE 250

(S)-3-{4-[2-Benzo(b)furanylcarboxamido]phenyl}-
2-(2-propylamino-3,4-dioxocyclobut-1-enylamino)
propanoic acid 2-Benzo(b)furancarboxylic acid gave the title compound (4.0 mg).

HPLC-MS (Conditions B). Retention time 2.45 min, MH$^+$ 462

EXAMPLE 251

(S)-3-[4-(4-Methoxy-2-quinolylcarboxamido)
phenyl]-2-(2-propylamino-3,4-dioxo cyclobut-1-enylamino)propanoic acid 4-Methoxy-2-quinolinecarboxylic acid gave the title compound (5.3 mg).

HPLC-MS (Conditions B). Retention time 2.59 min, MH$^+$ 503

EXAMPLE 252

(S)-3-{4-[4-Oxo-4,5,6,7,-tetrahydrobenzo(b)furan-3-ylcarboxamido]phenyl}-2-(2-propylamino-3,4-dioxocyclobut-1-enylamino)propanoic acid 4-Oxo-4,5,6,7-tetrahydrobenzo(b)furan-3-carboxylic acid gave the title compound (8.2 mg).

HPLC-MS (Conditions B). Retention time 2.37 min, MH$^+$ 480

EXAMPLE 253

(S)-3-[4-(2-(1-Pyrrolyl)-5-pyridylcarboxamido)
phenyl]-2-(2-propylamino-3,4-dioxocyclobut-1-enylamino)propanoic acid 2-(1-Pyrrolyl)-5-pyridinecarboxylic acid gave the title compound (1.7 mg).

HPLC-MS (Conditions B). Retention time 2.45 min, MH$^+$ 488

EXAMPLE 254

(S)-3-[4-(3-indazolylcarboxamido)phenyl]-2-(2-2-propylamino-3,4-dioxocyclobut-1-enyl amino)
propanoic acid 3-Indazolecarboxylic acid gave the title compound (5.0 mg).

HPLC-MS (Conditions B). Retention time 2.34 min, MH$^+$ 462

EXAMPLE 255

(S)-3-[4-(4-Fluorobenzoylamino)phenyl]-2-(2-propylamino-3,4-dioxocyclobut-1-enyl amino)propanoic acid 4-Fluorobenzoic acid gave the title compound (3.7 mg).
HPLC-MS (Conditions B). Retention time 2.37 min, MH$^+$ 440

EXAMPLE 256

(S)-3-[4-(4-Methoxybenzoylamino)phenyl]-2-(2-propylamino-3,4-dioxocyclobut-1-enylamino)propanoic acid 4-Methoxybenzoic acid gave the title compound (0.3 mg).
HPLC-MS (Conditions B). Retention time 2.34 min, MH$^+$ 452

EXAMPLE 257

(S)-3-[4-(4-Acetamidobenzoylamino)phenyl]-2-(2-propylamino-3,4-dioxocyclobut-1-enylamino)propanoic acid 4-Acetamidobenzoic acid gave the title compound (3.7 mg).
HPLC-MS (Conditions B). Retention time 2.16 min, MH$^+$ 479

EXAMPLE 258

(S)-3-[4-(4-Acetylbenzoylamino)phenyl]-2-(2-propylamino-3,4-dioxocyclobut-1-enyl amino)propanoic acid 4-Acetylbenzoic acid gave the title compound (2.0 mg).
HPLC-MS (Conditions B). Retention time 2.28 min, MH$^+$ 461

EXAMPLE 259

(S)-3-[4-(4-Nitrobenzoylamino)phenyl]-2-(2-propylamino-3,4-dioxocyclobut-1-enyl amino)propanoic acid 4-Nitrobenzoic acid gave the title compound (4.3 mg).
HPLC-MS (Conditions B). Retention time 2.39 min, MH$^+$ 467

EXAMPLE 260

(S)-3-{4-[4-(4-Hydroxyphenyl)benzoylamino]phenyl}-2-(2-propylamino-3,4-dioxocyclo but-1-enylamino)propanoic acid 4-Hydroxybiphenyl carboxylic acid gave the title compound (0.8 mg).
HPLC-MS (Conditions B). Retention time 2.36min, MH$^+$ 514

EXAMPLE 261

(S)-3-[4-(4-Cyanobenzoylamino)phenyl]-2-(2-propylamino-3,4-dioxocyclobut-1-enyl amino)propanoic acid 4-Cyanobenzoic acid gave the title compound (6.5 mg).
HPLC-MS (Conditions B). Retention time 2.32 min, MH$^+$ 447

EXAMPLE 262

(S)-3-[4-(4-Trifluoromethylbenzoylamino)phenyl]-2-(2-propylamino-3,4-dioxocyclobut-1-enylamino)propanoic acid 4-Trifluoromethylbenzoic acid gave the title compound (5.4 mg).
HPLC-MS (Conditions B). Retention time 2.55 min, MH$^+$ 560

EXAMPLE 263

(S)-3-[4-(N-Oxo-4-pyridylcarboxamido)phenyl]-2-propylamino-3,4-dioxocyclobut-1-enyl amino)propanoic acid 4-Pyridyl-N-oxide carboxylic acid gave the title compound (4.7 mg).
HPLC-MS (Conditions B). Retention time 1.97 min, MH$^+$ 439

EXAMPLE 264

(S)-3-[4-(2,6-Dichloro-3-pyridylcarboxamido)phenyl]-2-(2-propylamino-3,4-dioxocyclobut-1-enylamino)propanoic acid 2,6,-Dichloronicotinic acid gave the title compound (4.7 mg).
HPLC-MS (Conditions B). Retention time 2.31 min, MH$^+$ 493

EXAMPLE 265

(S)-3-[4-(2-(Methoxycarbonyl)benzoylamino)phenyl]-2-(2-propylamino-3,4-dioxocyclobut-1-enyl amino)propanoic acid 2-Methoxycarbonylbenzoic acid gave the title compound (3,4 mg).
HPLC-MS (Conditions B). Retention time 2.28 min, MH$^+$ 480

EXAMPLE 266

(S)-3-{4-[5-Methyl-2-(trifluoromethyl)-3-furanylcarboxamido]phenyl}-2-(2-propylamino-3,4-dioxocyclobut-1-enylamino)propanoic acid 5-Methyl-2-(trifluoromethyl)-3-furancarboxylic acid gave the title compound (5.6 mg).
HPLC-MS (Conditions B). Retention time 2.48 min, MH$^+$ 494

EXAMPLE 267

(S)-3-[4-(2-Acetyl-3-thienylcarboxamido)phenyl]-2-(2-propylamino-3,4-dioxocyclobut-1-enylamino)propanoic acid 2-Acetyl-3-thiophenecarboxylic acid gave the title compound (5.2 mg).
HPLC-MS (Conditions B). Retention time 2.28 min, MH$^+$ 470

EXAMPLE 268

(S)-3-{4-[(R)-2-Oxothiazolidin-4-ylcarboxamido]phenyl}-2-(2-propylamino-3,4-dioxo cyclobut-1-enylamino)propanoic acid (R)-2-Oxothiazolidine-4-carboxylic acid gave the title compound (5.4 mg).
HPLC-MS (Conditions B). Retention time 2.07 min, MH$^+$ 447

EXAMPLE 269

(S)-3-[4-(4-Nitro-3-pyrazolylcarboxamido)phenyl]-2-(2-propylamino--3,4-dioxocyclobut-1-enylamino) propanoic acid 4-Nitro-3-pyrazolecarboxylic acid gave the title compound (3.0 mg).
HPLC-MS (Conditions B). Retention time 2.14 min, MH$^+$ 457

EXAMPLE 270

(S)-3-[4-(5-Chloro-2-thienylcarboxamido)phenyl]-2-(2-propylamino-3,4-dioxocyclobut-1-enylamino) propanoic acid 5-Chloro-2-thiophenecarboxylic acid gave the title compound (5.3 mg).
HPLC-MS (Conditions B). Retention time 2.48 min, MH$^+$ 462

EXAMPLE 271

(S)-3-[4-(1-Methyl-5-nitro-4-pyrazolylcarboxamido)phenyl]-2-(2-propylamino-3,4-dioxocyclobut-1-enylamino)propanoic acid 1-Methyl-5-nitro-4-pyrazolecarboxylic acid gave the title compound (6.1 mg).
HPLC-MS (Conditions B). Retention time 2.23 min, MH$^+$ 471

EXAMPLE 272

(S)-3-[4-(2-Furoylamino)phenyl]-2-(2-propylamino-3,4-dioxocyclobut-1-enylamino) propanoic acid 2-Furoic acid gave the title compound (3.7 mg).
HPLC-MS (Conditions B). Retention time 2.23 min, MH$^+$ 412

EXAMPLE 273

(S)-3-[4-(2,4-Dimethyl-5-thiazolylcarboxamido)phenyl]-2-(2-propylamino-3,4-dioxo cyclobut-1-enylamino)propanoic acid 2,4-Dimethyl-5-thiazolecarboxylic acid gave the title compound (4.2 mg).
HPLC-MS (Conditions B). Retention time 2.18 min, MH$^+$ 457

EXAMPLE 274

(S)-3-[4-(1,2,3-thiadiazol-4-ylcarboxamido)phenyl]-2-(2-propylamino-3,4-dioxo cyclobut-1-enylamino) propanoic acid 1,2,3, Thiadiazole-5-carboxylic acid gave the title compound (4.9 mg).
HPLC-MS (Conditions B). Retention time 2.20 min, MH$^+$ 430

EXAMPLE 275

(S)-3-[4-(2-Thienylcarboxamido)phenyl]-2-(2-propylamino-3,4-dioxocyclobut-1-enylamino) propanoic acid 2-Thiophenecarboxylic acid gave the title compound (5.0 mg).
HPLC-MS (Conditions B). Retention time 2.31 min, MH$^+$ 428

EXAMPLE 276

(S)-3-[4-(2-Pyrazinylcarboxamido)phenyl]-2-(2-propylamino-3,4-dioxocyclobut-1-enyl amino) propanoic acid 2-Pyrazinecarboxylic acid gave the title compound (4.2 mg). HPLC-MS (Conditions B). Retention time 2.16 min, MH$^+$ 424

EXAMPLE 277

(S-3-{4-(2-Furyl)oxalylamino]phenyl}-2-(2-propylamino-3,4-dioxocyclobut-1-enylamino) propanoic acid α-Oxo-2-furanacetic acid gave the title compound (4.8 mg).
HPLC-MS (Conditions B). Retention time 2.3 min, MH$^+$ 440.

EXAMPLE 278

(S)-3-[4-(3-Methyl-2-thienylcarboxamido)phenyl]-2-(2-propylamino-3,4-dioxocyclo but-1-en ylamino) propanoic acid 3-Methyl-2-(2-thiophenecarboxylic acid gave the title compound (2.0 mg).
HPLC-MS (Conditions B). Retention time 2.37 min, MH$^+$ 442

EXAMPLE 279

(S)-3-[4-(4-Methyl-1,2,3-thiadiazol-5-ylcarboxamido)phenyl]-2-(2-propylamino-3,4-dioxocyclobut-1-enylamino)propanoic acid 4-Methyl-1,2,3-thiazole-5-carboxylic acid gave the title compound (4.0 mg).
HPLC-MS (Conditions B). Retention time 2.24 min, MH$^+$ 444

EXAMPLE 280

(S)-3-[4-(5-Phenyl-4-oxazolylcarboxamido)phenyl]-2-(2-propylamino-3,4-dioxocyclo but-1-enylamino) propanoic acid 5-Phenyl-4-oxazolecarboxylic acid gave the title compound (5.9 mg).
HPLC-MS (Conditions B). Retention time 2.51 min, MH$^+$ 489

EXAMPLE 281

(S)-3-[4-(3-Methyl-5-trifluoromethyl-4-isoxazolylcarboxamido)phenyl]-2-(2-propyl amino-3,4-dioxocyclobut-1-enylamino)propanoic acid 3-Methyl-5-trifluoromethyl-4-isoxazolecarboxylic acid gave the title compound (5.8 mg).
HPLC-MS (Conditions B). Retention time 2.43 min, MH$^+$ 495.

The following compounds of Examples 282 to 323 were prepared in a similar manner to the compound of Example 105, using derivatised resin (4) and the starting material shown. For examples where the amine was added as a salt 1 mol equivalent of DIPEA was also added.

EXAMPLE 282

(RS)-3-[4-(3,5-Dichloro-4-pyridylcarboxamido)
phenyl]-3-[2-(2-morpholinoethylamino)-3,4-
dioxocyclobut-1-enylamino]propanoic acid N-(2-Aminoethyl)morpholine gave the title compound (2 mg).
HPLC-MS (Conditions B) Retention time 1.98 min MH$^+$ 562

EXAMPLE 283

(RS)-3-[4-(3,5-Dichloro-4-pyridylcarboxamido)
phenyl]-3-[2-(2-piperidinoethylamino)-3,4-
dioxocyclobut-1-enylamino]propanoic acid 1-(2-Aminoethyl)piperidine gave the title compound (2 mg).
HPLC-MS (Conditions B) Retention time 2.02 min MH$^+$ 560

EXAMPLE 284

(RS)-3-[4-(3,5-Dichloro-4-pyridylcarboxamido)
phenyl]-3-[2-(3-(2-oxopyrrolidin-1-yl)propylamino)-
3,4-dioxocyclobut-1-enylamino]propanoic acid 1-(3-Aminopropyl)-2-pyrrolidinone gave the title compound (1 mg).
HPLC-MS (Conditions B) Retention time 2.14 min MH$^+$ 574

EXAMPLE 285

(RS)-3-[4-(3,5-Dichloro-4-pyridylcarboxamido)
phenyl]-3-[2-(3-(1-imidazolyl)propylamino)-3,4-
dioxocyclobut-1-enylamino]propanoic acid N-(3-Aminopropyl)imidazole gave the title compound (3 mg).
HPLC-MS (Conditions B) Retention time 1 98 min MH$^+$ 557

EXAMPLE 286

(RS)-3-[4-(3,5-Dichloro-4-pyridylcarboxamido)
phenyl]-3-[2-(1-benzyl4-piperidinylamino)-3,4-
dioxocyclobut-1-enylamino]propanoic acid 4-Amino-1-benzylpiperidine gave the title compound (6 mg).
HPLC-MS (Conditions B) Retention time 2.13 min MH$^+$ 622

EXAMPLE 287

(RS)-3-[4-(3,5-Dichloro-4-pyridylcarboxamido)
phenyyl]-3-[2-(2-pyridylmethylamino)-3,4-
enylamino]propanoic acid 2-(Aminomethyl)pyridine gave the title compound (6 mg).
HPLC-MS (Conditions B) Retention time 2.17 min MH$^+$ 540

EXAMPLE 288

(RS)-3-[4-(3,5-Dichloro-4-pyridylcarboxamido)
phenyl]-3-[2-(3-pyridylmethylamino)-3,4-
dioxocyclobut-1-enylamino]propanoic acid 3-(Aminomethyl)pyridine gave the title compound (3 mg).
HPLC-MS (Conditions B) Retention time 2.07 min MH$^+$ 540

EXAMPLE 289

(RS)-3-[4-(3,5-Dichloro-4-pyridylcarboxamido)
phenyl]-3-[2-(3,3-dimethylbutylamino)-3,4-
dioxocyclobut-1-enylamino]propanoic acid 3,3-Dimethylbutylamine gave the title compound (3 mg).
HPLC-MS (Conditions B) Retention time 2.45 min MH$^+$ 533

EXAMPLE 290

(RS)-3-[4-(3,5-Dichloro-4-pyridylcarboxamido)
phenyl]-3-[2-(3,4-dichlorobenzylamino)-3,4-
dioxocyclobut-1-enylamino]propanoic acid 3,4-Dichlorobenzylamine gave the title compound (4 mg).
HPLC-MS (Conditions B) Retention time 2.51 min MH$^+$ 607

EXAMPLE 291

(RS)-3-[4-(3,5-Dichloro-4-pyridylcarboxamido)
phenyl]-3-[2-(2-(1-piperazinyl)ethylamino)-3,4-
dioxocyclobut-1-enylamino]propanoic acid N-(2-Aminoethyl)piperazine gave the title compound (1 mg).
HPLC-MS (Conditions B) Retention time 1.97 min MH$^+$ 561

EXAMPLE 292

(RS)-3-[4-(3,5-Dichloro-4-pyridylcarboxamido)
phenyl]-3-[(2-isopropylamino-3,4-dioxocyclobut-1-
enylamino)propanoic acid Isopropylamine gave the title compound (1 mg).
HPLC-MS (Conditions B) Retention time 2.25 min MH$^+$ 491

EXAMPLE 293

(RS)-3-[4-(3,5-Dichloro-4-pyridylcarboxamido)
phenyl]-3-(2-propylamino-3,4-dioxocyclobut-1-
enylamino)propanoic acid Propylamine gave the title compound (2 mg).
HPLC-MS (Conditions B) Retention time 2.25 min MH$^+$ 491

EXAMPLE 294

(RS)-3-[4-(3,5-Dichloro-4-pyridylcarboxamido)
phenyl]-3-(2-tertbutylamino-3,4-dioxocyclobut-1-
enylamino)propanoic acid Tert-Butylamine gave the title compound (0.5 mg).
HPLC-MS (Conditions B) Retention time 2.33 min MH$^+$ 505

EXAMPLE 295

(RS)-3-[4-(3,5-Dichloro-4-pyridylcarboxamido)
phenyl]-3-(2-benzylamino-3,4-dioxocyclobut-1-
enylamino)propanoic acid Benzylamine gave the title compound (1 mg).
HPLC-MS (Conditions B) Retention time 2.37 min MH$^+$ 539

EXAMPLE 296

(RS)-3-[4-(3,5Dichloro-4-pyridylcarboxamido)
phenyl]-3-[2-(3-(dimethylamino)propylamino)-3,4-
dioxocyclobut-1-enylamino]propanoic acid 3-(Dimethylamino)propylamine gave the title compound (0.5 mg).
HPLC-MS (Conditions B) Retention time 1.89 min MH$^+$ 534

EXAMPLE 297

(RS)-3-[4-(3,5-Dichloro-4-pyridylcarboxamido)
phenyl]-3-[2-(3-isopropoxypropylamino)-3,4-
dioxocyclobut-1-enylamino]propanoic acid 3-Isopropoxypropylamine gave the title compound (1 mg).
HPLC-MS (Conditions B) Retention time 2.3 min MH$^+$ 549

EXAMPLE 298

(RS)-3-[4-(3,5-Dichloro-4-pyridylcarboxamido)
phenyl]-3-[2-(3-ethoxypropylamino)-3,4-
dioxocyclobut-1-enylamino]propanoic acid 3-Ethoxypropylamine gave the title compound (2 mg).
HPLC-MS (Conditions B) Retention time 2.23 min MH$^+$ 535

EXAMPLE 299

(RS)-3-[4-(3,5-Dichloro-4-pyridylcarboxamido)
phenyl]-3-[2-(2-methoxyethylamino)-3,4-
dioxocyclobut-1-enylamino]propanoic acid 2-Methoxyethylamine gave the title compound (0.5 mg).
HPLC-MS (Conditions B) Retention time 2.16 min MH$^+$ 507

EXAMPLE 300

(RS)-3-[4-3,5-Dichloro-4-pyridylcarboxamido)
phenyl]-3-[2-(3-methoxypropylamino)-3,4-
dioxocyclobut-1-enylamino]propanoic acid 3-Methoxypropylamine gave the title compound (0.5 mg).
HPLC-MS (Conditions B) Retention time 2.18 min MH$^+$ 521

EXAMPLE 301

(RS)-3-[4-(3,5-Dichloro-4-pyridylcarboxamido)
phenyl]-3-(2-cyclobutylamino-3,4-dioxocyclobut-1-
enylamino)propanoic acid Cyclobutylamine gave the title compound (2 mg).
HPLC-MS (Conditions B) Retention time 2.28 min MH$^+$ 503

EXAMPLE 302

(RS)-3-[4-(3,5-Dichloro-4-pyridylcarboxamido)
phenyl]-3-(2-cyclopropylamino-3,4-dioxocyclobut-
1-enylamino)propanoic acid Cyclopropylamine gave the title compound (2 mg).
HPLC-MS (Conditions B) Retention time 2.19 min MH$^+$ 489

EXAMPLE 303

(RS)-3-[4-(3,5-Dichloro-4-pyridylcarboxamido)
phenyl]-3-[2-(2-(benzylthio)ethylamino)-3,4-
dioxocyclobut-1-enylamino]propanoic acid 2-(Benzylthio)ethylamine hydrochloride gave the title compound (0.5 mg).
HPLC-MS (Conditions B) Retention time 2.46 min MH$^+$ 599

EXAMPLE 304

(RS)-3-[4-(3,5-Dichloro-4-pyridylcarboxamido)
phenyl]-3-[2-(4-(1,2,3-thiadiazol-4-yl)benzylamino)-
3,4-dioxocyclobut-1-enylamino]propanoic acid 4-(1,2,3-Thiadiazol-4-yl)benzylamine gave the title compound (2 mg).
HPLC-MS (Conditions B) Retention time 2.38 min MH$^+$ 623

EXAMPLE 305

(RS)-3-[4-(3,5-Dichloro-4-pyridylcarboxamido)
phenyl]-3-(2-cyclohexylamino-3,4-dioxocyclobut-1-
enylamino)propanoic acid Cyclohexylamine gave the title compound (0.5 mg).
HPLC-MS (Conditions B) Retention time 2.39 min MH$^+$ 531

EXAMPLE 306

(RS)-3-[4-(3,5-Dichloro-4-pyridylcarboxamido)
phenyl]-3-[2-piperidinyl-3,4-dioxocyclobut-1-
enylamino]propanoic acid Piperidine gave the title compound (2 mg).
HPLC-MS (Conditions A) Retention time 2.32 min MH$^+$ 517

EXAMPLE 307

(RS)-3-[4-(3,5-Dichloro-4-pyridylcarboxamido)
phenyl]-3-(2-thiomorpholino-3,4-dioxocyclobut-1-
enylamino)propanoic acid Thiomorpholine gave the title compound (1 mg).
HPLC-MS (Conditions A) Retention time 2.32 min MH$^+$ 535

EXAMPLE 308

(RS)-3-[4-(3,5-Dichloro-4-pyridylcarboxamido)
phenyl]-3-[2-(4-methyl-1-piperazinyl)-3,4-
dioxocyclobut-1-enylamino]propanoic acid 1-Methylpiperazine gave the title compound (3 mg).
HPLC-MS (Conditions A) Retention time 1.93 min MH$^+$ 532

EXAMPLE 309

(RS)-3-[4-(3,5-Dichloro-4-pyridylcarboxamido)
phenyl]-3-(2-diethylamino-3,4-dioxocyclobut-1-
enylamino)propanoic acid Diethylamine gave the title compound (2 mg).
HPLC-MS (Conditions A) Retention time 2.29 min MH$^+$ 505

EXAMPLE 310

(RS)-3-[4-(3,5-Dichloro-4-pyridylcarboxamido)phenyl]-3-[2-(1-pyrrolidinyl)-3,4-dioxocyclobut-1-enylamino]propanoic acid Pyrrolidine gave the title compound (1 mg).
HPLC-MS (Conditions A) Retention time 2.24 min MH$^+$ 503

EXAMPLE 311

(RS)-3-[4-(3,5-Dichloro-4-pyridylcarboxamido)phenyl]-3-[2-(4-ethyl-1-piperazinyl)-3,4-dioxocyclobut-1-enylamino]propanoic acid 1-Ethylpiperazine gave the title compound (1 mg).
HPLC-MS (Conditions A) Retention time 1.94 min MH$^+$ 546

EXAMPLE 312

(RS)-3-[4-(3,5-Dichloro-4-pyridylcarboxamido)phenyl]-3-[2-(4-(hydroxypropyl)-1-piperazinyl)-3,4-dioxocyclobut-1-enylamino]propanoic acid 1-Piperazinepropanol gave the title compound (3 mg).
HPLC-MS (Conditions A) Retention time 1.93 min MH$^+$ 576

EXAMPLE 313

(RS)-3-[4-(3,5-Dichloro-4-pyridylcarboxamido)phenyl]-3-[2-(1-piperazinyl)-3,4-dioxocyclobut-1-enylamino]propanoic acid Piperazine gave the title compound (4 mg).
HPLC-MS (Conditions A) Retention time 1.92 min MH$^+$ 518

EXAMPLE 314

(RS)-3-[4-(3,5-Dichloro-4-pyridylcarboxamido)phenyl]-3-[2-((S-3-dimethylamino-1-pyrrolidinyl)-3,4-dioxocyclobut-1-enylamino]propanoic acid (S)-3-(Dimethylamino)pyrrolidine gave the title compound (3 mg).
HPLC-MS (Conditions A) Retention time 1.92 min MH$^+$ 546

EXAMPLE 315

(RS)-3-[4-(3,5-Dichloro-4-pyridylcarboxamido)phenyl]-3-[2-((RS)-3-diethylamino-1-pyrrolidinyl)-3,4dioxocyclobut-1-enylamino]propanoic acid 3-(Diethylamino)pyrrolidine gave the title compound (3 mg).
HPLC-MS (Conditions A) Retention time 1.95 min MH$^+$ 574

EXAMPLE 316

(RS)-3-[4-(3,5-Dichloro-4-pyridylcarboxamido)phenyl]-3-(2-butylamino-3,4-dioxocyclobut-1-enylamino)propanoic acid Butylamine gave the title compound (0.1 mg).
HPLC-MS (Conditions A) Retention time 2.33 min MH$^+$ 505

EXAMPLE 317

(RS)-3-[4-(3,5-Dichloro-4-pyridylcarboxamido)phenyl]-3-(2-pentylamino-3,4-dioxocyclobut-1-enylamino]propanoic acid Pentylamine gave the title compound (1 mg).
HPLC-MS (Conditions A) Retention time 2.40 min MH$^+$ 519

EXAMPLE 3198

(RS)-3-[4-(3,5-Dichloro-4-pyridylcarboxamido)phenyl]-3-[2-((RS)-2-butylamino)-3,4-dioxocyclobut-1-enylamino]propanoic acid 1-Methylpropylamine gave the title compound (2 mg).
HPLC-MS (Conditions A) Retention time 2.31 min MH$^+$ 505

EXAMPLE 319

(RS)-3-[4-(3,5-Dichloro-4-pyridylcarboxamido)phenyl]-3-(2-isobutylamino-3,4-dioxocyclobut-1-enylamino)propanoic acid Isobutylamine gave the title compound (2 mg).
HPLC-MS (Conditions A) Retention time 2.31 min MH$^+$ 505

EXAMPLE 320

(RS)-3-[4-(3,5-Dichloro-4-pyridylcarboxamido)phenyl]-3-[2-(N-methyl-N-isopropylamino)-3,4-dioxocyclobut-1-enylamino]propanoic acid Methylisopropylamine gave the title compound (2 mg).
HPLC-MS (Conditions A) Retention time 2.3 min MH$^+$ 505

EXAMPLE 321

(RS)-3-[4-(3,5-Dichloro-4-pyridylcarboxamido)phenyl]-3-[2-(N-ethyl-N-methylamino)-3,4-dioxocyclobut-1-enylamino]propanoic acid N-Ethylmethylamine gave the title compound (0.2 mg).
HPLC-MS (Conditions A) Retention time 2.24 min MH$^+$ 491

EXAMPLE 322

(RS)-3-[4-(3,5-Dichloro-4-pyridylcarboxamido)phenyl]-3-[2-(N-methyl-N-butylamino)-3,4-dioxocyclobut-1-enylamino]propanoic acid N-Methylbutylamine gave the title compound (0.3 mg).
HPLC-MS (Conditions A) Retention time 2.38 min MH$^+$ 519

EXAMPLE 323

(RS)-3-[4-(3,5-Dichloro-4-pyridylcarboxamido)phenyl]-3-[2-(N-ethyl-N-(pyridylmethyl)amino]-3,4-dioxocyclobut-1-enylamino]propanoic acid 4-(Ethylaminomethyl)pyridine gave the title compound (1 mg).
HPLC-MS (Conditions A) Retention time 2.01 min MH$^+$ 568

EXAMPLE 324

3-[4-(3,5-Dichloro-4-pyridylcarboxamido)phenyl]-2-(2-isopropylamino-3,4-dioxocyclobut-1-enylamino)prop-2-enoic acid Derivatised resin 6 (1.0 g) was treated with the Intermediate 44 (0.4 g, 3.0 mmol) and a catalytic amount of dirhodiumtetraacetate in toluene (10 ml) at 1200 for 2.5 h. The resin was then filtered and washed with DMF and DCM to give resin bound α-(2-methoxy-3,4-dioxocyclo-but-1-enylamino)diethylphosphonoacetate. This resin was then treated with 4-(3,5-dichloro-4-pyridylcarboxamido)benzaldehyde (0.53 g, 1.8 mmol) and diazabicycloundec-7-ene (DBU) (0.1 g, 1.2 mmol) in DCM (5.0 ml). The mixture was agitated at ambient temperature for 72 h then filtered and the resin washed thoroughly with DCM. A 90 mg portion of this resin was treated with 2-propylamine (0.045 mL, 0.6 mmol), in DCM (0.2 mL) and MeOH (0.8 mL). The mixture was agitated at ambient temperature for 16 h then filtered and washed thoroughly with DCM, MeOH, DMF, MeOH and DCM. The resin was treated with 50% trifluoroacetic acid in DCM (2 ml) for 3 h with agitation and then filtered. The resin was washed with a further portion of DCM (2 ml) and the combined filtrate was evaporated in vacuo to give the crude product which was purified by preparative HPLC to afford the title compound (0.9 mg).

HPLC-MS (Conditions B). Retention time 2.29 min, MH$^+$ 489

The following compound of Example 325 was prepared in an identical manner to the compound of Example 324, using the starting material shown.

EXAMPLE 325

3-[4-(3,5-Dichloro-4-pyridylcarboxamido)phenyl]-2-(2-cyclobutylamino-3,4-dioxocyclobut-1-enylamino)prop-2-enoic acid Cyclobutylamine gave the title compound (0.4 mg).

HPLC-MS (Conditions B). Retention time 2.33 min, MH$^+$ 501.

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-dependent Jurkat Cell Adhesion to VCAM-Ig 96 well NUNC plates were coated with F(ab)$_2$ fragment goat anti-human IgG Fcγ-specific antibody [Jackson Immuno Research 109-006-098: 100 μl at 2 μg/ml in 0.1M NaHCO$_3$, pH 8.4], overnight at 4°. The plates were washed (3×) in phosphate-buffered saline (PBS) and then blocked for 1 h in PBS/1% BSA at RT on a rocking platform. After washing (3× in PBS) 9 ng/ml of purified 2d VCAM-Ig diluted in PBS/1% BSA was added and the plates left for 60 minutes at RT on a rocking platform. The plates were washed (3× in PBS) and the assay then performed at 37° for 30 min in a total volume of 200 μl containing 2.5×10$^5$ Jurkat cells in the presence or absence of titrated test compounds.

Each plate was washed (2×) with medium and the adherent cells were fixed with 100 μl MeOH for 10 minutes followed by another wash. 100 μl 0.25% Rose Bengal (Sigma R4507) in PBS was added for 5 minutes at RT and the plates washed (3×) in PBS. 100 μl 50% (v/v) ethanol in PBS was added and the plates left for 60 min after which the absorbance (570 nm) was measured.

$\alpha_4\beta_7$ Integrin-dependent JY Cell Adhesion to MAdCAM-Ig

This assay was performed in the same manner as the $\alpha_4\beta_1$ assay except that MAdCAM-Ig (150 ng/ml) was used in place of 2d VCAM-Ig and a subline of the β-lymphoblastoid cell-line JY was used in place of Jurkat cells. The IC$_{50}$ value for each test compound was determined as described in the $\alpha_4\beta_1$ integrin assay.

$\alpha_5\beta_1$ Integrin-dependent K562 Cell Adhesion to Fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at RT on a rocking platform. The blocked plates were washed (3× in PBS) and the assay then performed at 37° C. in a total volume of 200 μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-Dependent Human Polymorphonuclear Neutrophils Adhesion to Plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at RT. The plates were washed in medium and 100μl 0.1% (w/v) HMB (hexadecyl trimethyl ammonium bromide, Sigma H5882) in 0.05M potassium phosphate buffer, pH 6.0 added to each well. The plates were then left on a rocker at RT for 60 min. Endogenous peroxidase activity was then assessed using tetramethyl benzidine (TMB) as follows: PMN lysate samples mixed with 0.22% H$_2$O$_2$ (Sigma) and 50 μg/ml TMB (Boehringer Mannheim) in 0.1M sodium acetate/citrate buffer, pH 6.0 and absorbance measured at 630 nm.

αIIb/β$_3$-Dependent Human Platelet Aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220×g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays the preferred compounds of the invention in which R$^1$ is an $\alpha_4$ integrin binding group, such as the compounds of the Examples generally have IC$_{50}$ values in the $\alpha_4\beta_1$ and $\alpha_4\beta_7$ assays of 1 μM and below. In the other assays featuring α integrins of other subgroups the same compounds had IC$_{50}$ values of 50 μM and above thus demonstrating the potency and selectivity of their action against $\alpha_4$ integrins.

The following assays may be used to determine the ability of compounds according to the invention to inhibit $\alpha_v\beta_3$ and $\alpha_v\beta_5$ function.

$\alpha_v\beta_3$-Dependent Direct Binding Assay

96 Well NUNC immunoplates were coated overnight with a non-blocking anti-β3 monoclonal antibody at 2 μg/ml in Dulbecco's phosphate buffered saline (PBS) and subsequently blocked with 5% 9 w/v)BSA in PBS (Sigma, fraction V) for 60 min. at RT. After washing in Tris-buffered saline (TBS: 20 mM Tris/150 mM NaCl, pH 7.5), plates then received 100 μl of a lysate prepared from JY cells and were incubated for 3 h at RT. The lysate was made by lysing JY B-lymphoblastoid cells at 5×10$^7$ cells were ml in TBS containing 1 mM MnCl$_2$, 1% (v/v) BSA/0.1% (vb/v) Tween 20 and were incubated for a further 2 hours at RT. Inhibitors were titrated into the fibronectin prior to addition to plates. After washing, streptavidin-peroxidase (Amersham) at 1:500 in TBS/1% (w/v) BSA/0.1% (v/v)Tween 20 was added and plates incubated for 1 h at RT. Finally 100 μl TMB substrate was added and Absorbance (630 nm) measured after 10–15 minutes. IC$_{50}$ values for inhibition of adhesion were calculated on the Activity Base curve fitting programme.

α$_v$β$_3$-Dependent Cell Adhesion Assay

This was a modification of a published method [Stupack et al., Exp,. Cell. Tes. 203, 443–448 (1992)] and employed the JY cell line. These cells are maintained in RPMI 1640+10% FCS+2 mM L-glutamine and, when used for assay, were washed in assat medium (RPMI 1640+10% FCS), suspended at 4×10$^6$/ml in the same medium and pretreated with a blocking monoclonal antibody to CD18 (6.5E, F(ab')$_2$ fragment) for 10 min at RT. 96 Well NUNC immunoplates were coated with 100 μl 2.5 uk/μl human vitronectin in PBS per well for 2 h at 37° C.; they were then washed 2× in PBS and blocked with 1% (w/v) BSA in PBS for 60 min at RT and washed 2× more in PBS. 2×1-$^5$ JY per well were added to wells containing compounds serially titrated across the plate and, finally, phorbol-12-myristate-13-acetate at 10 ng/ml was added in a final volume of 200 μl. After incubation at 37° C. for 30 min, non-adherent cells were removed by washing 3× in assay medium, adherent cells were fixed in MeOH and stained with 0.25% (w/v) Rose Bengal in PBS for 5 min, unbound dye was removed by 3 further washes in PBS and cell-bound dye was released with 1:1 PBS:ethanol. Absorbance at 570 nm was then measured. IC$_{50}$ values for inhibition of adhesion were calculated as described above for the direct binding assay.

α$_v$β$_5$-Dependent Cell Adhesion Assay

This assay was based on a published method [Koivunen et al, J. Bio. Chem. 268, 20205–20210 (1993)] and employed the human colon adenocarcinoma cell line HT-29. HT-29 Cells were routinely maintained in DMEM+10% FCS+2 mM L-glutamine and were removed from flasks using trypsin/EDTA, washed 2× in assay medium and suspended at 4×10$^6$/ml in the same medium. The cells were allowed to 'rest' for 15 min. at RT before being added (2×10$^5$/well) to wells containing compounds serially titrated across the plate in a final volume of 200 μl. The 96 well NUNC immunoplates had been coated with human vitronectin as described above for the α$_v$β$_3$ assay. After incubation at 37° C. for 60 min, adhesion was assessed as described above for the α$_v$β$_3$ assay.

In the above assays the preferred compounds of the invention generally have IC$_{50}$ values of 1 μM and below.

The advantageous clearance properties of compounds according to the invention may be demonstrated as follows:

Hepatic clearance, whether metabolic or biliary, can make a substantial contribution to the total plasma clearance of a drug. The total plasma clearance is a principal parameter of the pharmacokinetic properties of a medicine. It has a direct impact on the dose required to achieve effective plama concentrations and has a major impact on the elimination half-life and therefore the dose-interval. Furthermore, high hepatic clearance is an indicator of high first-pass hepatic clearance after oral administration and therefore low oral bioavailability.

Many peptidic and non-peptidic carboxylic acids of therapeutic interest are subject to high hepatic clearance from plasma. Except for drugs which function in the liver, hepatic uptake from blood or plasma is undesirable because it leads to high hepatic clearance if the compound is excreted in bile or metabolised, or if the substance is not cleared from the liver, it may accumulate in the liver and interfere with the normal function of the liver.

The total plasma clearance of a compound according to the invention can be determined as follows:

a small dose of the compound in solution is injected into a vein of a test animal. Blood samples are withdrawn from a blood vessel of the animal at several times after the injection, and the concentration of compound in the bleed or plasma is measured using a suitable assay. The area under the curve (AUCiv) is calculated by non-compartmental methods (for example, the trapezium method) or by pharmacokinetic modelling. The total plasma clearance (CL$_p$) is calculated by dividing the intravenous dose(D$_{iv}$) by the AUC$_{iv}$ for the blood plasma concentration–time course of a drug administered by the intravenous route: CL$_p$=D$_{iv}$÷AUC$_{iv}$.

When tested in this manner, compounds according to the invention are not rapidly or extensively extracted by the liver and have low total plasma clearance where low is defined as less than 10 ml/min/kg in the laboratory rat (Sprague Dawley CD). This compares favourably with functionally equivalent integrin binding compounds in which the squaric acid framework of compounds of formla (1) is not present.

What is claimed is:

1. A compound of formula (1):

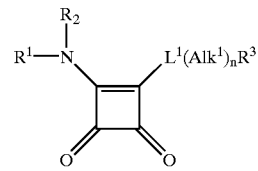

wherein

R$^1$ is an integrin binding group of formula Ar$^1$L$^2$Ar$^2$Alk—, where Ar$^1$ is an optionally substituted naphthyridinyl group;

L$^2$ is a linker atom or group selected from the group consisting of L$^{2a}$ and —Alk$^a$(L$^{2a}$)$_y$—;

wherein L$^{2a}$ is —O—, —S—, —C(O)—, —C(O)O—, —OC(O)—, —C(S)—, —S(O)—, —S(O)$_2$—, —N(R$^8$)—, —N(R$^8$)O—, —N(R$^8$)N—, —CON(R$^8$)—, —OC(O)N(R$^8$)—, —CSN(R$^8$)—, —N(R$^8$)CO—, —N(R$^8$)C(O)O—, —N(R$^8$)CS—, —S(O)$_2$N(R$^8$)—, —N(R$^8$)S(O)$_2$—, —N(R$^8$)CON(R$^8$)—, —N(R$^8$)CSN(R$^8$)—, or —N(R$^8$)SO$_2$N(R$^8$)—;

R$^8$ is a hydrogen atom or an optionally substituted C$_{1-6}$alkyl group;

Alk$^a$ is an optionally substituted aliphatic or heteroaliphatic chain; and y is zero or the integer 1;

Ar$^2$ is an optionally substituted phenylene or nitrogen-containing six-membered heteroarylene group;

Alk is a chain selected from the group consisting of:

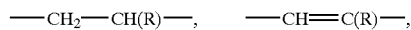

 and where R is a carboxylic acid (—CO$_2$H) or a derivative thereof, or R is a biostere of a carboxylic acid selected from the group consisting of tetrazole, phosphonic acid, phosphinic acid, sulphonic acid, sulphinic acid, boronic acid and an acylsulphonamide group;

$R^2$ is a hydrogen atom or a $C_{1-6}$ alkyl group;

$L^1$ is a covalent bond or a linker atom or group selected from the group consisting of —O—, —S—, —C(O)—, —C(O)O—, —OC(O)—, —C(S)—, —S(O)—, —S(O)$_2$—, —N($R^8$)—, —N($R^8$)O—, —N($R^8$)N—, —CON($R^8$)—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)CON($R^8$)—, —N($R^8$)CSN($R^8$)—, and —N($R^8$)SO$_2$N($R^8$)—;

n is zero or the integer 1;

$Alk^1$ is an optionally substituted aliphatic chain;

$R^3$ is a hydrogen atom or an optionally substituted heteroaliphatic, cycloaliphatic, heterocycloaliphatic, polycycloaliphatic, polyheterocycloaliphatic, aromatic or heteroaromatic group;

and the salts, solvates, hydrates and N-oxides thereof.

2. A compound according to claim 1 in which Alk is a chain selected from

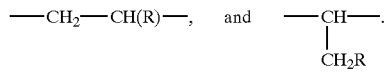

3. A compound according to claim 2, in which R is a carboxylic acid (—CO$_2$H) group.

4. A compound according to claim 1 in which $Ar^2$ is an optionally substituted 1,4-phenylene group.

5. A compound according to claim 1 in which $L^2$ is a —CON($R^8$)— group where $R^8$ is a hydrogen atom or an optionally substituted $C_{1-6}$alkyl group.

6. A compound according to claim 5 in which $R^8$ is a hydrogen atom.

7. A compound according to claim 1 in which $Ar^1$ is an optionally substituted 2,6-napthyridinyl group.

8. A compound according to claim 7 in which $L^2$ is an —O— or —N($R^8$)— group where $R^8$ is a hydrogen atom or an optionally substituted $C_{1-6}$alkyl group.

9. A compound according to claim 8 in which $R^8$ is a hydrogen atom.

10. A compound according to claim 1 in which $L^1$ is a —N($R^8$)— group where $R^8$ is a hydrogen atom or an optionally substituted $C_{1-6}$alkyl group.

11. A compound according to claim 10 which $R^8$ is a hydrogen atom or methyl, ethyl or n-propyl group.

12. A compound according to claim 1 in which $L^1$ is a covalent bond.

13. A compound according to claim 1 in which n is the integer 1 and $Alk^1$ is an optionally substituted straight or branched $C_{1-6}$alkylene chain.

14. A compound according to claim 13 in which $Alk^1$ is a —CH$_2$—, —CH$_2$CH$_2$—, —CH$_2$CH$_2$CH$_2$—, —CH(CH$_3$)CH$_2$— or —C(CH$_3$)$_2$CH$_2$— chain.

15. A compound according to claim 4 in which $R^3$ is a hydrogen atom.

16. A compound according to claim 1 of formula (2b)

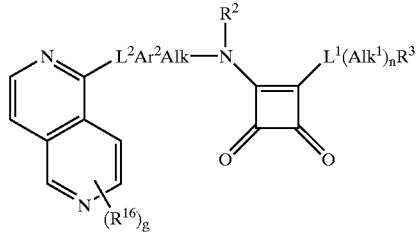

wherein $R^{16}$ is a hydrogen atom or a group —$L^3$(Alk$^2$)$_t$L$^4$(R$^4$)$_u$ in which $L^3$ is a covalent bond or a linker atom or group selected from the group consisting of —O—, —S—, —C(O)—, —C(O)O—, OC(O)—, —C(S)—, —S(O)—, —S(O)$_2$—, —N($R^8$)—, —N($R^8$)O—, —N($R^8$)N—, —CON($R^8$)—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)CON($R^8$)—, —N($R^8$)CSN($R^8$)—, and —N($R^8$)SO$_2$N($R^8$)—;

$R^8$ is a hydrogen atom or an optionally substituted $C_{1-6}$alkyl group;

$Alk^2$ is an aliphatic or heteroaliphatic chain;

t is zero or the integer 1;

$L^4$ is a covalent bond or a linker atom or group selected from the group consisting of —O—, —S—, —C(O)—, —C(O)O—, —OC(O)—, —C(S)—, —S(O)—, —S(O)$_2$—, —N($R^8$)—, —N($R^8$)O—, —N($R^8$)N—, —CON($R^8$)—, —OC(O)N($R^8$)—, —CSN($R^8$)—, —N($R^8$)CO—, —N($R^8$)C(O)O—, —N($R^8$)CS—, —S(O)$_2$N($R^8$)—, —N($R^8$)S(O)$_2$—, —N($R^8$)CON($R^8$)—, —N($R^8$)CSN($R^8$)—, and —N($R^8$)SO$_2$N($R^8$)—;

$R^4$ is a hydrogen or halogen atom or a group selected from optionally substituted $C_{1-6}$alkyl or $C_{3-8}$cycloalkyl, —OR$^5$ (where $R^5$ is a hydrogen atom, an optionally substituted $C_{1-6}$alkyl or $C_{3-8}$cycloalkyl group), —SR$^5$, —NR$^5$R$^6$ (where $R^6$ is as just defined for $R^5$ and may be the same or different), —NO$_2$, —CN, —CO$_2$R$^5$, —SO$_3$H, —SOR$^5$, —SO$_2$R$^5$, —SO$_3$R$^5$, —OCO$_2$R$^5$, —CONR$^5$R$^6$, —OCONR$^5$R$^6$, —CSNR$^5$R$^6$, —COR$^5$, —OCOR$^5$, —N(R$^5$)COR$^6$, —N(R$^5$)CSR$^6$, —SO$_2$N(R$^5$)(R$^6$), —N(R$^5$)SO$_2$R$^6$, N(R$^5$)CON(R$^6$)(R$^7$)(where $R^7$ is a hydrogen atom substituted $C_{1-6}$alkyl or $C_{3-8}$cycloalkyl group), —N(R$^5$)CSN(R$^6$)(R$^7$) or —N(R$^5$)SO$_2$N(R$^6$)(R$^7$), provided that when t is zero and each of $L^3$ and $L^4$ is a covalent bond then u is the integer 1 and $R^4$ is other than a hydrogen atom;

g is zero or the integer 1, 2, 3, or 4;

and the salts, solvates, hydrates and N-oxides thereof.

17. A compound which is:

(S)-3-[4-([2,6-Naphthyridin-1-yl]amino)phenyl]-2-[(2-N,N-diethylamino-3,4-dioxocyclobut-1-enyl)amino]propanoic acid;

(S)-3-[4-([2,6-Naphthyridin-1-yl]amino)phenyl]-2-[(2-N,N-dipropylamino-3,4-dioxocyclobut-1-enyl)amino]propanoic acid;

(S)-3-[4-([2,6-Naphthyridin-1-yl]oxy)phenyl]-2-[(2-N,N-diethyllamino-3,4-dioxocyclobut-1-enyl)amino]propanoic acid;

(S)-3-[4-([2,6-Naphthyridin-1-yl]amino)phenyl]-2-[(2-piperidin-1-yl-3,4-dioxocyclobut-1-enyl)amino]propanoic acid;

(S)-3-[4-([2,6-Naphthyridin-1-yl]oxy)phenyl]-2-[(2-N,N-dipropylamino-3,4-dioxocyclobut-1-enyl)amino]propanoic acid;

(S)-3-[4-([2,6-Naphthyridin-1-yl]amino)phenyl]-2-[(2-N,-ethyl-N-isopropylamino-3,4-dioxocyclobut-1-enyl)amino]propanoic acid; and the salts, solvates, hydrates and N-oxides thereof.

18. A pharmaceutical composition comprising a compound according to claim 1 together with one or more pharmaceutically acceptable carriers, excipients or diluents.

19. A method for the treatment of a disease or disorder in a mammal in which the extravasation of leukocytes plays a role, comprising administering to a mammal suffering from such a disease or disorder a therapeutically effective amount of a compound according to claim 1.

20. A method according to claim 19 wherein said disease or disorder is selected from the group consisting of inflammatory arthritis, multiple sclerosis, allograft rejection, diabetes, inflammatory dermatoses, asthma and inflammatory bowel disease.

21. A method for inhibiting, in a mammal, the binding of α4 integrins to the ligands thereof, comprising administering to the mammal an effective amount of a compound according to claim 1.

22. A method according to claim 21 wherein the α4 integrins are selected from the group consisting of α4β1 and α4β7 integrins.

* * * * *